(12) United States Patent
Nell et al.

(10) Patent No.: US 8,304,412 B2
(45) Date of Patent: Nov. 6, 2012

(54) CYCLICALLY SUBSTITUTED 3,5-DICYANO-2-THIOPYRIDINES AND USE THEREOF

(75) Inventors: Peter Nell, Wuppertal (DE); Walter Hübsch, Wuppertal (DE); Barbara Albrecht-Küpper, Wülfrath (DE); Alexandros Vakalopoulos, Hilden (DE); Frank Süssmeier, Wuppertal (DE); Jörg Keldenich, Wuppertal (DE); Joachim Telser, Wuppertal (DE)

(73) Assignee: Bayer Intellectual Property GmbH, Monheim (DE)

( * ) Notice: Subject to any disclaimer, the term of this patent is extended or adjusted under 35 U.S.C. 154(b) by 191 days.

(21) Appl. No.: 12/516,917

(22) PCT Filed: Nov. 17, 2007

(86) PCT No.: PCT/EP2007/009962
§ 371 (c)(1),
(2), (4) Date: May 29, 2009

(87) PCT Pub. No.: WO2008/064788
PCT Pub. Date: Jun. 5, 2008

(65) Prior Publication Data
US 2010/0022544 A1  Jan. 28, 2010

(30) Foreign Application Priority Data
Dec. 1, 2006 (DE) .................. 10 2006 056 740

(51) Int. Cl.
A61K 31/5377 (2006.01)
A61K 31/44 (2006.01)
A61K 31/497 (2006.01)
A61P 3/10 (2006.01)
C07D 417/12 (2006.01)
C07D 409/14 (2006.01)
C07D 413/14 (2006.01)

(52) U.S. Cl. .................. 514/236.8; 514/342; 514/253.1; 544/124; 544/364; 546/270.7

(58) Field of Classification Search .................. None
See application file for complete search history.

(56) References Cited

U.S. PATENT DOCUMENTS

| 4,052,510 | A | 10/1977 | Simpson et al. |
| 5,670,525 | A | 9/1997 | Urbahns et al. |
| 5,889,002 | A | 3/1999 | Nielsen et al. |
| 6,191,280 | B1 | 2/2001 | Hamprecht et al. |
| 6,693,102 | B2 | 2/2004 | Stasch et al. |
| 6,706,717 | B2 | 3/2004 | Barrish et al. |
| 6,743,798 | B1 | 6/2004 | Straub et al. |
| 6,833,364 | B1 | 12/2004 | Straub et al. |
| 6,864,287 | B1 | 3/2005 | Alonso-Alija et al. |
| 7,045,631 | B2 | 5/2006 | Rosentreter et al. |
| 7,078,417 | B2 | 7/2006 | Rosentreter et al. |
| 7,129,255 | B2 | 10/2006 | Rosentreter et al. |
| 7,173,036 | B2 | 2/2007 | Sircar et al. |
| 7,173,037 | B2 | 2/2007 | Alonso-Alija et al. |
| 7,186,716 | B2 | 3/2007 | Wei et al. |
| 7,674,825 | B2 | 3/2010 | Alonso-Alija et al. |
| 7,692,017 | B2 | 4/2010 | Dinsmore et al. |
| 7,705,043 | B2 | 4/2010 | Alonso-Alija et al. |
| 7,709,504 | B2 | 5/2010 | Krahn et al. |
| 7,781,470 | B2 | 8/2010 | Alonso-Alija et al. |
| 7,855,219 | B2 | 12/2010 | Rosentreter et al. |
| 7,932,259 | B2 | 4/2011 | Nakazato et al. |
| 7,951,811 | B2 | 5/2011 | Nakazato et al. |
| 2004/0162427 | A1 | 8/2004 | Rosentreter et al. |
| 2004/0176446 | A1 | 9/2004 | Alonso-Alija et al. |
| 2005/0182105 | A1 | 8/2005 | Nirschi et al. |
| 2005/0227972 | A1 | 10/2005 | Rosentreter et al. |
| 2006/0264432 | A1 | 11/2006 | Rosentreter et al. |
| 2007/0066630 | A1 | 3/2007 | Palani et al. |
| 2007/0213372 | A1 | 9/2007 | Rosentreter et al. |
| 2007/0293670 | A1 | 12/2007 | Nakazato et al. |
| 2008/0269300 | A1 | 10/2008 | Erguden et al. |
| 2009/0221649 | A1 | 9/2009 | Krahn et al. |
| 2010/0009973 | A1 | 1/2010 | Rhodes et al. |
| 2010/0048641 | A1 | 2/2010 | Nell et al. |
| 2010/0069363 | A1 | 3/2010 | Nell et al. |
| 2010/0093728 | A1 | 4/2010 | Nell et al. |
| 2010/0197609 | A1 | 8/2010 | Vakalopoulos et al. |
| 2011/0130377 | A1 | 6/2011 | Nell et al. |
| 2011/0207698 | A1 | 8/2011 | Meibom et al. |
| 2011/0294718 | A1 | 12/2011 | Lerchen et al. |
| 2011/0294719 | A1 | 12/2011 | Lerchen et al. |

FOREIGN PATENT DOCUMENTS

| EP | 0 608 565 A1 | 12/1993 |
| EP | 1302463 | 4/2003 |
| JP | 09-132529 | 5/1997 |
| JP | 10-324687 | 12/1998 |
| JP | 2003-183254 | 7/2003 |
| WO | 95/34563 | 12/1995 |

(Continued)

OTHER PUBLICATIONS

Vippagunta et al., Advanced Drug Delivery Reviews, vol. 48, p. 3-26 (on p. 3), 2001.*
V. D. Dyachenko, Russian Journal of General Chemistry (2006), vol. 76(2), p. 282-291, (cited in IDS by Applicants).*
Patani et al., Chem. Rev., 1996, vol. 96, p. 3147-3176.*
Dyachenko, Russian Journal of General Chemistry, 2006, vol. 76 (2), p. 282-291 (previously cited).*
Beukers, M.W. et al., "New, Non-Adenosine, High-Potency Agonists for the Human Adenosine $A_{2B}$ Receptor with an Improved Selectivity Profile Compared to the Reference Agonist N-Ethylcarboxamidoadenosine", Journal of Medicinal Chemistry, Jul. 15, 2004; vol. 47, No. 15, pp. 3707-3709.

(Continued)

Primary Examiner — Yong Chu
(74) Attorney, Agent, or Firm — Thomas C. Blankinship; Karen B. King

(57) ABSTRACT

The present application relates to novel 4-cycloalkyl- and 4-heterocycloalkyl-3,5-dicyano-2-thio-pyridine derivatives, to processes for their preparation, to their use for the treatment and/or prophylaxis of diseases and to their use for preparing medicaments for the treatment and/or prophylaxis of diseases, preferably for the treatment and/or prevention of hypertension and other cardiovascular disorders.

10 Claims, No Drawings

FOREIGN PATENT DOCUMENTS

| WO | 97/27177 A2 | 7/1997 |
|---|---|---|
| WO | 99/03861 A1 | 1/1999 |
| WO | WO-99/32117 A1 | 7/1999 |
| WO | WO-01/25210 A2 | 4/2001 |
| WO | WO 01/62233 | 8/2001 |
| WO | WO 0206237 A1 * | 1/2002 |
| WO | 02/48115 A2 | 6/2002 |
| WO | WO-02/50071 A1 | 6/2002 |
| WO | WO 02/070485 | 9/2002 |
| WO | WO-03/053441 A1 | 7/2003 |
| WO | 03/091246 | 11/2003 |
| WO | 2004/014372 A1 | 2/2004 |
| WO | WO-2004/054505 A2 | 7/2004 |
| WO | WO-2005/007647 A1 | 1/2005 |
| WO | WO-2005/046603 A2 | 5/2005 |
| WO | WO-2006/027142 A1 | 3/2006 |
| WO | WO-2006/034446 A2 | 3/2006 |
| WO | 2007/073855 | 7/2007 |

OTHER PUBLICATIONS

Dyachenko, V.D., "Cyclohexanecarbaldehyde in Multicomponent Syntheses of Funtionalized Cyclohexyl-Substituted Acrylonitriles, 4H-Chalcogenopyrans, 1, 4-Dihydropyridines, and Pyridines", Russian Journal of General Chemistry, 76(2), 282-291, Feb. 2006.

M. E. Olah et al.: "Cloning, Expression, and Characterization of the Unique Bovine $A_1$ Adenosine Receptor," The Journal of Biological Chemistry, vol. 367, No. 15, May 25, 1991, pp. 10764-10770.

K-N. Klotz et al.: "Comparartive Pharmacology of Human Adenosine Receptor Subtypes—Characterization of Stably Transfected Receptors in CHO Cells," Naunyn-Schmiedeberg's Arch Pharmacol, 357, 1998, pp. 1-9.

S-A Poulsen et al.: "Adenosine Receptors: New Opportunities for Future Drugs," Bioorganic & Medicinal Chemistry, 6, 1998, pp. 619-641.

Anand, et al.:"Novel Dipeptide Prodrugs of Acyclovir for Ocular Herpes Infections: Bioreversion, Antiviral Activity and Transport Across Rabbit Cornea," Current Eye Research, Mar. 2003, 26 (3-4):151-163.

Avila, et al: A1-, A2A- and A3-subtype adenosine receptors modulate intraocular pressure in the mouse, British Journal of Pharmacology, 2001, 134:241-245.

Barton et al.,:"Homologation of Acids via Carbon Radicals Generated from the Acyl Derivatives of N-Hydroxy-2-Thiopyrodine. (The Two-Carbon Problem)," Tetrahedron Letters, 1991, 32(28): 3309-3312.

Bauman:"Updating the Evidence that Physical Activity is Good for Health: An Epidemiological Review 2000-2003," J. Sci. Med. Sport, Apr. 2004, 7(1): Suppl:6-19.

Beaumont, et al.:"Design of Ester Prodrugs to Enhance Oral Absorption of Poorly Permeable Compounds: Challenges to the Discovery Scientist," Current Drug Metabolism, 2003, 4(6):461-485.

Bundgaard:"Design of Prodrugs: Bioreversible Derivatives for Various Functional Groups and Chemical Entities," Elsevier Science Publishers B.V., 1985, pp. 1092.

Castedo, et al.:"Synthesis and Pharmacological Activity of Some Nitrofuraldehyde Cyanopyridine Derivatives," Eur. J. Med. Chem., 1984, 19(6):555-557, abstract retrieved from CAPLUS Accession No. 1985:437337, EPO Document XP002202946.

Cesar, et al.:"Trimethylsilyldiazomethane in the Preparation of Diazoketonesvia Mixed Anhydride and Coupling Reagent Methods:A New Approach to the Arndt—Eistert Synthesis," Tetrahedron Letters, 2001, 42: 7099-7102.

Crosson: "Intraoccular Pressure Responses to the Adenosine Agonist Cyclohexyladenosine: Evidence for a Dual Mechanism of Action," IOVS, Jul. 2001, 42(8): 1837-1840.

Dhalla, et al.:"Pharmacology and Theraputic Applications of A1 Adenosine Receptor Ligands," Current Topics in Medicinal Chemisty, 2003, 3:369-385.

Dyachenko, et al.:"Single Stage Synthesis of 2-Alkylthio(seleno)-4-Hetaryl-3-cyano-5,6,7,8-Tetrahydroquinolines," Chemistry of Heterocyclic Compounds, 1997, 33(10): 1203-1208.

Dyachenko, et al.:"New Route to 6-Amino-4-aryl-3,5-dicyano-pyridine-2(1H)-thiones," Russian Journal of Organic Chemistry,1997, 33(7):1014-1017.

Dyachenko, et al.:"Michael Reaction in SyntheSis of 6-Amino-4-(4-Butoxyphenyl)-3,5- Dicyanopyridine-2(1H)-thionene," Chemistry of Heterocyclic Compounds, 1998, 34(2):188-194.

Dyachenko, et al.,:"Synthesis and Recyclization of 4-Aryl-2,6-diamino-3,5-dicyano-4H-thiopyrans," Russian Journal of Organic Chemistry, 1998, 34(4): 557-563.

Eissa, et al.:"Synthesis and Biological Evaluation of Pyrido[2,3-d]pyrimidine as Antitumor Effect," Egypt. J. Chem., 2006, 49(6):761-774.

Elnagdi, et al.:"Studies with Polyfunctionally Substituted Heterocycles: Synthesis of New Pyridines, Naphtho[1,2-b] pyrans, Pyrazolo[3,4]pyridines and Pyrazolo[1,5-a]pyrimidines," Z. Naturforsch, 1992, 47b:572-578.

El-Torgoman, et al.:"Nitriles in Heterocyclic Synthesis: The reaction of 2-Thiocarbamoyl Cinnamonitriles with Active Methylene Reagents," Z. Naturforsch., 1987, 42b:107-111.

Ettmayer, et al.:"Lessons Learned from Marketed and Investigational Prodrugs," J. Med. Chem., May 6, 2004, 47(10) 2393-2404.

Fuentes, et al.:"Heterocycle Synthesis. XVI. Reaction of Malononitrile with Benzylidenemalononitriles in Presence of Amines." An. Quim., Ser. C., 1980, 76(1): 68-69, English language abstract retrieved from CAPLUS Accession No. 1981:139574, EPO Document No. XP002202947.

Goto, et al.:"Studies on Azole Compounds.III.1 Reactions of Oxazole N-Oxides with Phosphoryl Chloride and Acetic Anhydride 2", Chem. Pharm. Bull. 1971, 19: 2050-2057.

Ibrahim, et al.:"Synthesis and Biological Activity of Some New Heterocyclic Quinoline Derivatives," Phosphorus, Sulfer, and Silicon, 1991, 57: 293-301.

Jacobson, et al,:"Adenosine Receptors as Theraputic Targets," Nat. Rev. Drug Discover.,2005, 5:247-264.

Jacobson, et al.:"Adenosine Receptor Ligands: Differences with Acute Versus Chronic Treatment," Trends in Pharmacological Sciences, Mar. 1996, 17(3):108-113.

Kambe, et al.:"Synthetic Studies Using $\alpha,\beta$-Unsaturated Nitriles: Facile Synthesis of Pyridine Derivatives," Synthesis Communications, Jul. 1981, pp. 531-533.

Klotz:"Adenosine Receptors and their Ligands," Naunyn-Schmiedeberg's Arch. Pharmacol., 2000, 362: 382-391.

Müller, et al.:"Adenosine Receptor Antagonists: Structures and Potential Therapeutic Applications," Current Pharmaceutical Design, 1996, 2:501-530.

Müller:"Adenosine Receptor Ligands-Recent Developments Part I. Agonists," Current Medicinal Chemistry, 2000, 7:1269-1288.

Müller:"Review. Cardiovascular & Renal. A1-Adenosine Receptor Antagonists," Exp. Opin. Ther. Patents, 1997, 7 (5):419-440.

Inotek Pharmaceuticals Press Release, "Inotek Pharmaceuticals Initiates Multiple-Dose Phase 2 Clinical Trial of INO-8875 in Patients with Glaucoma," Jun. 17, 2010.

Patani, et al.: "Bioisosterism: A Rational Approach in Drug Design," Chem. Rev., 1996, 96:3147-3176.

Pflueger, et al.:"Role of Adenosine in Contrast Media-Induced Acute Renal Failure in Diabetes Mellitus," Mayo Clin Proc., Dec. 2000, 75(12):1275-1283.

Quintela, et al.:"Reactivity of Heterocyclic Compounds. V. Behavior of 6-alkoxy-2-amino-(or chloro)-4-aryl-3,5-dicyanopyridines in the Presence of Nucleophiles," Anales de Quimica, Serie C: Quimica Organica y Bioquimica, 1984, 80(3):268-72, English language abstract retrieved from CAPLUS Accession No. 1985:437345, CAPLUS Document No. 103:37345, EPO Document No. XP002202945.

Quintela, et al.:"Synthesis, Antihistaminic and Cytotoxic Activity of Pyridothieno- and Pyridodithienotriazines", Eur. J. Med. Chem, 1998, 33:887-897.

Rodinovskaya, et al.:"Substituted 4-(3-Cyanopyridin-2-ylthio)acetoacetates: New Convenient Reagents for the Synthesis of Heterocycles," Synthesis, 2006, (14): 2357-2370.

Rosenman:"Do Environmental Effects on Human Emotions Cause Cardiovascular Disorders?," Acta Physiologica Scandinavica, Supplement, 1997, 161/640 (133-136), abstract retrieved from EMBASE Accession No. 97358868.

Ruhe, et al.: "Use of Antioxidant Nutrients in the Prevention and Treatment of Type 2 Diabetes," Journal of the American College of Nutrition, 2001, 20(5): 363S-369S.

Shams, et al.: "Nitriles in Organic Synthesis. New Routes for Synthesis of Pyridines and Azinothiopyrans," Journal fuer Praktische Chemie (Leipzig), 1988, 330(5):817-13, abstract retrieved from CAPLUS Accession No. 1989:497050.

Sheridan: "The Most Common Chemical Replacements in Drug-Like Compounds," J Chem. Inf. Comput. Sci., 2002, 42:103-108.

Suttner, et al.: "The Heart in the Elderly Critically Ill Patient," Curr. Opin. Crit. Care, Oct. 2002, 8(5):389-94, abstract retrieved from MEDLINE Accession No. 2002495386, PubMed ID: 12357105.

Szydlowski, et al.: "Biological Role of Chromium," Diabetologia Polska, 2003, 10(3):365-370, English language abstract retrieved from EMBASE Accession No. 2004016455.

Vasudevan A. et al., "Aminopiperidine indazoles as orally efficacious melanin concentrating hormone receptoer-1 antagonists," Bioorg. Med. Chem. Lett. 2005, 15 (23), 5293-5297.

Vippagunta, et al.: "Dystalline Solids," Advanced Drug Delivery Reviews, May 16, 2001, 48(1):3-26.

West: "Solid State Chemistry and its Applications," Wiley, New York, 1988, pp. 358 & 365.

Ye, et al.: Organic Synthesis with α-Diazocarbonyl Compounds, Chem. Rev. 1994, 94:1091-1160.

Yu, et al.: "Physical Characterization of Polymorphic Drugs: An Integrated Characterization Strategy," Pharmaceutical Science & Technology Today, Jun. 1998, 1(3):118-127.

Zhu, G. et al., "Design and synthesis of pyridine-pyrazolopyridine-based inhibitors of protein kinase B/Akt," Bioorg. Med. Chem. 2007, 15 (6), 2441-2452.

U.S. Appl. No. 13/210,889, filed Aug. 16, 2011.

* cited by examiner

CYCLICALLY SUBSTITUTED 3,5-DICYANO-2-THIOPYRIDINES AND USE THEREOF

RELATED APPLICATIONS/PATENTS AND INCORPORATION BY REFERENCE

This application is a National Stage Application filed under 35 U.S.C. §371 based on International Application No. PCT/EP2007/009962, filed Nov. 17, 2007, which claims priority to German Patent Application Number 102006056740.4, filed Dec. 1, 2006, the entire contents each of which are incorporated herein by reference.

The foregoing applications, and all documents cited therein and all documents cited or referenced therein, and all documents cited or referenced herein, including any U.S. or foreign patents or published patent applications, International patent applications, as well as, any non-patent literature references and any manufacturer's instructions, are hereby expressly incorporated herein by reference.

The present application relates to novel 4-cycloalkyl- and 4-heterocycloalkyl-3,5-dicyano-2-thio-pyridine derivatives, to processes for their preparation, to their use for the treatment and/or prophylaxis of diseases and to their use for preparing medicaments for the treatment and/or prophylaxis of diseases, preferably for the treatment and/or prevention of hypertension and other cardiovascular disorders.

Adenosine, a purine nucleoside, is present in all cells and is released by a large number of physiological and pathophysiological stimuli. Adenosine is formed intracellularly as an intermediate during the degradation of adenosine 5'-monophosphate (AMP) and S-adenosylhomocysteine, but it can be released from the cell, in which case it acts as a hormone-like substance or neurotransmitter by binding to specific receptors.

Under normoxic conditions, the concentration of free adenosine in the extracellular space is very low. However, under ischemic or hypoxic conditions, the extracellular concentration of adenosine in the affected organs is increased dramatically. Thus, it is known, for example, that adenosine inhibits platelet aggregation and increases the blood supply to the coronary arteries. Furthermore, it acts on the blood pressure, on the heart rate, on the release of neurotransmitters and on lymphocyte differentiation. In adipocytes, adenosine is capable of inhibiting lipolysis, thus lowering the concentration of free fatty acids and triglycerides in the blood.

The aim of these actions of adenosine is to increase the oxygen supply of the affected organs and/or to reduce the metabolism of these organs in order to adjust the metabolism of the organ to the blood supply of the organ under ischemic or hypoxic conditions.

The action of adenosine is mediated via specific receptors. To date, subtypes A1, A2a, A2b and A3 are known. According to the invention, "adenosine-receptor-selective ligands" are substances which bind selectively to one or more subtypes of the adenosine receptors, thus either mimicking the action of adenosine (adenosine agonists) or blocking its action (adenosine antagonists).

The actions of these adenosine receptors are mediated intracellularly by the messenger cAMP. In the case of the binding of adenosine to the A2a or A2b receptors, the intracellular cAMP is increased via activation of the membrane-bound adenylate cyclase, whereas binding of adenosine to the A1 or A3 receptors results in a decrease of the intracellular cAMP concentration via inhibition of adenylate cyclase.

In the cardiovascular system, the main consequences of the activation of adenosine receptors are: bradycardia, negative inotropism and protection of the heart agains ischemia ("preconditioning") via A1 receptors, dilation of the blood vessels via A2a and A2b receptors and inhibition of the fibroblasts and smooth-muscle-cell proliferation via A2b receptors.

In the case of A1 agonists (coupling preferably via $G_i$ proteins), a decrease of the intracellular cAMP concentration is observed (preferably after direct prestimulation of adenylate cyclase by forskolin). Correspondingly, A2a and A2b agonists (coupling preferably via $G_s$ proteins) leads to an increase and A2a and A2b antagonists to a decrease of the cAMP concentration in the cells. In the case of A2 receptors, a direct prestimulation of adenylate cyclase by forskolin is of no benefit.

The activation of A2b receptors by adenosine or specific A2b agonists leads, via dilation of blood vessels, to lowering of the blood pressure. The lowering of the blood pressure is accompanied by a refectory increase in heart rate. The increased heart rate can be reduced by activation of A1 receptors using specific A1 agonists.

The combined action of selective A1/A2b agonists on the vascular system and heart rate thus results in a systemic lowering of the blood pressure without relevant heart-rate increase. Dual A1/A2b agonists having such a pharmacological profile could be employed, for example, for treating hypertension in humans.

In adipocytes, the activation of A1 and A2b receptors leads to an inhibition of lipolysis. Thus, the combined action of A1/A2b agonists on lipid metabolism results in a lowering of free fatty acids and triglycerides. In turn, in patients suffering from metabolic syndrome and in diabetics, reduced lipids lead to lower insulin resistance and improved symptoms.

The abovementioned receptor selectivity can be determined by the effect of the substances on cell lines which, after stable transfection with the corresponding cDNA, express the receptor subtypes in question see the publication M. E. Olah, H. Ren, J. Ostrowski, K. A. Jacobson, G. L. Stiles, "Cloning, expression, and characterization of the unique bovine A1 adenosine receptor. Studies on the ligand binding site by site-directed mutagenesis", *J. Biol. Chem.* 267 (1992), pages 10764-10770, the disclosure of which is hereby fully incorporated by way of reference].

The effect of the substances on such cell lines can be monitored by biochemical measurement of the intracellular messenger cAMP [see the publication K. N. Klotz, J. Hessling, J. Hegler, C. Owman, B. Kull, B. B. Fredholm, M. J. Lohse, "Comparative pharmacology of human adenosine receptor subtypes—characterization of stably transfected receptors in CHO cells", *Naunyn Schmiedebergs Arch. Pharmacol.* 357 (1998), pages 1-9, the disclosure of which is hereby fully incorporated by way of reference].

The "adenosine-receptor-specific" ligands known from the prior art are mainly derivatives based on natural adenosine [S.-A. Poulsen and R. J. Quinn, "Adenosine receptors: New opportunities for future drugs", *Bioorganic and Medicinal Chemistry* 6 (1998), pages 619-641]. However, most of the adenosine ligands known from the prior art have the disadvantage that their action is not really receptor-specific, that their activity is less than that of natural adenosine or that they have only very weak activity after oral administration. Thus, they are mainly used only for experimental purposes. Compounds of this type which are still in clinical development are hitherto only suitable for intravenous application.

In WO 01/25210 and WO 02/070485 describe substituted 2-thio-3,5-dicyano-4-aryl-6-amino-pyridines as adenosine receptor ligands for the treatment of disorders. WO 03/053441 discloses specifically substituted 2-thio-3,5-dicyano-4-phenyl-6-aminopyridines as selective ligands for the adenosine A1 receptor, and WO 2006/027142 claims substituted phenylaminothiazole derivatives as dual adenosine A1/A2b agonists for the treatment of hypertension and other cardiovascular disorders. However, it was found that some of these compounds have disadvantages with respect to their physicochemical and/or pharmacokinetic properties, such as, for example, their solubility in water and other physiological media or their resorption behavior in the body.

WO 01/62233 discloses various pyridine and pyrimidine derivatives and their use as adenosine receptor modulators. The use of 4-cycloalkyl- and 4-heterocycloalkyl-substituted 3,5-dicyanopyridines as calcium-dependent potassium channel openers for treating urological disorders is described in EP 1 302 463-A1. WO 2004/054505 claims the use of 2-amino-3-cyanopyridine derivatives as MK-2 inhibitors for treating various disorders. Various hetero-cyclically substituted pyridine derivatives and their use for treating diseases are described in WO 99/32117, WO 2005/046603, WO 2005/007647 and WO 2006/034446. WO 02/50071 discloses aminothiazole derivatives as tyrosine kinase inhibitors for the treatment of cancer and also immunological and allergic disorders.

It was an object of the present invention to provide novel compounds which act as selective agonists of the adenosine A1 receptor or as selective dual agonists of the adenosine A1 and A2b receptor and which, as such, are suitable for the treatment and/or prevention in particular of hypertension and other cardiovascular disorders, of metabolic syndrome, of diabetes and dyslipidemias and also for the protection of organs during transplantations and surgical interventions, and which additionally have an improved physicochemical and/or pharmacokinetic profile compared to the substances known from the prior art.

The present invention provides compounds of the formula (I)

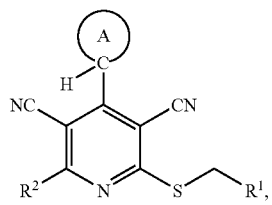

(I)

in which ring A represents a $(C_4-C_7)$-cycloalkyl or $(C_4-C_7)$-cycloalkenyl ring or represents a 4- to 7-membered heterocycle which is attached via carbon and which contains one or two ring members from the group consisting of N—$R^3$ and O, where $(C_4-C_7)$-cycloalkyl and $(C_4-C_7)$-cycloalkenyl may be mono- or disubstituted by identical or different radicals selected from the group consisting of $(C_1-C_6)$-alkyl, hydroxyl, $(C_1-C_6)$-alkoxy, amino, mono-$(C_1-C_6)$-alkylamino and di-$(C_1-C_6)$-alkylamino, where the $(C_1-C_6)$-alkyl and $(C_1-C_6)$-alkoxy radicals mentioned for their part may be mono- or disubstituted by identical or different radicals from the group consisting of hydroxyl, $(C_1-C_4)$-alkoxy and $(C_3-C_6)$-cycloalkyl, and where $R^3$ represents hydrogen, $(C_1-C_6)$-alkyl which may be mono- or disubstituted by identical or different radicals from the group consisting of hydroxyl, $(C_1-C_4)$-alkoxy, $(C_1-C_4)$-acyloxy and $(C_3-C_6)$-cycloalkyl, or $(C_1-C_6)$-acyl which may be substituted by hydroxyl or $(C_1-C_4)$-alkoxy, $R^1$ represents $(C_6-C_{10})$-aryl or 5- to 10-membered heteroaryl having up to three ring heteroatoms from the group consisting of N, O and S, each of which radicals may
(i) be mono- or disubstituted by identical or different radicals selected from the group consisting of halogen, nitro, cyano, $(C_1-C_6)$-alkyl, trifluoromethyl, hydroxyl, $(C_1-C_6)$-alkoxy, amino, mono-$(C_1-C_6)$-alkylamino, di-$(C_1-C_6)$-alkylamino, carboxyl, $(C_1-C_6)$-alkoxycarbonyl, carbamoyl, mono-$(C_1-C_6)$-alkylaminocarbonyl and di-$(C_1-C_6)$-alkylaminocarbonyl
and/or
(ii) be substituted by pyrrolidino, piperidino, morpholino, piperazino, N'—$(C_1-C_4)$-alkylpiperazino, tetrazolyl or a group of the formula -L-$R^4$ in which
L represents a bond, NH or O
and
$R^4$ represents phenyl or 5- or 6-membered heteroaryl having up to three ring heteroatoms from the group consisting of N, O and S, each of which radicals may be mono- to trisubstituted by identical or different radicals selected from the group consisting of halogen, nitro, cyano, $(C_1-C_6)$-alkyl, trifluoromethyl, hydroxyl, $(C_1-C_6)$-alkoxy, difluoromethoxy, trifluoromethoxy, amino, mono-$(C_1-C_6)$-alkylamino, di-$(C_1-C_6)$-alkylamino, $(C_1-C_6)$-alkoxycarbonyl and carboxyl,
and
$R^2$ represents hydrogen or represents $(C_1-C_6)$-alkyl or $(C_1-C_6)$-alkoxy, each of which radicals may be substituted by hydroxyl, $(C_1-C_4)$-alkoxy, carboxyl, $(C_1-C_4)$-alkoxycarbonyl or up to three times by fluorine
or
$R^2$ represents a group of the formula —$NR^5R^6$ in which
$R^5$ and $R^6$ are identical or different and independently of one another represent hydrogen or $(C_1-C_6)$-alkyl which may be mono- or disubstituted by identical or different radicals from the group consisting of hydroxyl, $(C_1-C_4)$-alkoxy, amino, mono-$(C_1-C_4)$-alkylamino, di-$(C_1-C_4)$-alkylamino, carboxyl, $(C_1-C_4)$-alkoxycarbonyl and a 4- to 7-membered heterocycle,
where the heterocycle mentioned contains one or two ring heteroatoms from the group consisting of N, O and S and for its part may be mono- or disubstituted by identical or different radicals from the group consisting of $(C_1-C_4)$-alkyl, hydroxyl, oxo and $(C_1-C_4)$-alkoxy,
or
$R^5$ and $R^6$ together with the nitrogen atom, to which they are attached, form a 4- to 7-membered heterocycle which may contain a further ring heteroatom from the group consisting of N, O or S and may be mono- or disubstituted by identical or different radicals from the group consisting of $(C_1-C_4)$-alkyl, hydroxyl, oxo, $(C_1-C_4)$-alkoxy, azetidino, pyrrolidino, piperidino and morpholino,
and N-oxides, salts, solvates, salts of the N-oxides and solvates of the N-oxides and salts thereof,
except for the compound 2-amino-6-(benzylthio)-4-(tetrahydro-2H-pyran-2-yl)-pyridine-3,5-dicarbonitrile.

Compounds according to the invention are the compounds of the formula (I) and the salts, solvates and solvates of the salts thereof, the compounds which are encompassed by the formula (I) and are mentioned in the formulae below, and the salts, solvates and solvates of the salts thereof, and the compounds which are encompassed by formula (I) and are mentioned below as exemplary embodiments, and the salts, solvates and solvates of the salts thereof, where the compounds which are encompassed by the formula (I) and are mentioned below are not already salts, solvates and solvates of the salts.

The compounds according to the invention may, depending on their structure, exist in stereoisomeric forms (enantiomers, diastereomers). The invention therefore encompasses the enantiomers or diastereomers and respective mixtures thereof. The stereoisomerically pure constituents can be isolated from such mixtures of enantiomers and/or diastereomers in a known manner.

Where the compounds according to the invention can exist in tautomeric forms, the present invention encompasses all tautomeric forms.

Salts preferred for the purposes of the present invention are physiologically acceptable salts of the compounds according to the invention. Also included are salts which are not themselves suitable for pharmaceutical applications but can be used, for example, for the isolation or purification of the compounds according to the invention.

Physiologically acceptable salts of the compounds according to the invention include acid addition salts of mineral acids, carboxylic acids and sulfonic acids, for example salts of hydrochloric acid, hydrobromic acid, sulfuric acid, phosphoric acid, methanesulfonic acid, ethanesulfonic acid, toluenesulfonic acid, benzenesulfonic acid, naphthalenedisulfonic acid, acetic acid, trifluoroacetic acid, propionic acid, lactic acid, tartaric acid, malic acid, citric acid, fumaric acid, maleic acid and benzoic acid.

Physiologically acceptable salts of the compounds according to the invention also include salts of conventional bases such as, by way of example and preferably, alkali metal salts (for example sodium and potassium salts), alkaline earth metal salts (for example calcium and magnesium salts) and ammonium salts derived from ammonia or organic amines having 1 to 16 carbon atoms, such as, by way of example and preferably, ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine and N-methylpiperidine.

Solvates refer for the purposes of the invention to those forms of the compounds according to the invention which form a complex in the solid or liquid state through coordination with solvent molecules. Hydrates are a specific form of solvates in which the coordination takes place with water. For the purposes of the present invention, preferred solvates are hydrates.

In addition, the present invention also encompasses prodrugs of the compounds according to the invention. The term "prodrugs" encompasses compounds which for their part may be biologically active or inactive but are converted (for example metabolically or hydrolytically) into compounds according to the invention during their residence time in the body.

For the purposes of the present invention, the substituents have the following meaning, unless specified otherwise:

For the purposes of the invention, $(C_{1-6})$-alkyl and $(C_{1-4})$-alkyl are straight-chain or branched alkyl radicals having 1 to 6 and 1 to 4 carbon atoms, respectively. Preference is given to a straight-chain or branched alkyl radical having 1 to 4 carbon atoms. The following radicals may be mentioned by way of example and by way of preference: methyl, ethyl, n-propyl, isopropyl, n-butyl, isobutyl, sec-butyl, tert-butyl, 1-ethylpropyl, n-pentyl and n-hexyl.

For the purposes of the invention, $(C_4-C_7)$-cycloalkyl, $(C_3-C_6)$-cycloalkyl and $(C_3-C_5)$-cycloalkyl represent a monocyclic saturated carbocycle having 4 to 7, 3 to 6 and 3 to 5 ring carbon atoms, respectively. The following radicals may be mentioned by way of example and by way of preference: cyclopropyl, cyclobutyl, cyclopentyl, cyclohexyl and cycloheptyl.

For the purposes of the invention, $(C_4-C_7)$-cycloalkenyl represents a monocyclic carbocycle having 4 to 7 ring carbon atoms and one double bond. The following radicals may be mentioned by way of example and by way of preference: cyclobut-2-en-1-yl, cyclopent-2-en-1-yl, cyclopent-3-en-1-yl, cyclohex-2-en-1-yl, cyclohex-3-en-1-yl and cyclohept-3-en-1-yl.

For the purposes of the invention, $(C_1-C_6)$-alkoxy and $(C_1-C_4)$-alkoxy represent straight-chain or branched alkoxy radicals having 1 to 6 and 1 to 4 carbon atoms, respectively. Preference is given to a straight-chain or branched alkoxy radical having 1 to 4 carbon atoms. The following radicals may be mentioned by way of example and by way of preference: methoxy, ethoxy, n-propoxy, isopropoxy, n-butoxy, tert-butoxy, n-pentoxy and n-hexoxy.

For the purposes of the invention, $(C_1-C_6)$-alkoxycarbonyl and $(C_1-C_4)$-alkoxycarbonyl represent a straight-chain or branched alkoxy radical having 1 to 6 and 1 to 4 carbon atoms, respectively, which is attached via a carbonyl group. Preference is given to a straight-chain or branched alkoxy-carbonyl radical having 1 to 4 carbon atoms in the alkoxy group. The following radicals may be mentioned by way of example and by way of preference: methoxycarbonyl, ethoxycarbonyl, n-propoxycarbonyl, isopropoxycarbonyl and tert-butoxycarbonyl.

For the purposes of the invention, $(C_1-C_6)$-acyl and $(C_1-C_4)$-acyl [$(C_1-C_6)$-alkanoyl and $(C_1-C_4)$-alkanoyl] represent a straight-chain or branched alkyl radical having 1 to 6 and 1 to 4 carbon atoms, respectively, which carries a doubly attached oxygen atom in the 1-position and is attached in the 1-position. Preference is given to an acyl radical having 1 to 4 carbon atoms. The following radicals may be mentioned by way of example and by way of preference: formyl, acetyl, propionyl, n-butyryl, isobutyryl, n-pentanoyl, pivaloyl and n-hexanoyl.

For the purposes of the invention, $(C_1-C_4)$-acyloxy represents a straight-chain or branched alkyl radical having 1 to 4 carbon atoms, which carries a doubly attached oxygen atom in the 1-position and is attached in the 1-position via a further oxygen atom. The following radicals may be mentioned by way of example and by way of preference: acetoxy, propionoxy, n-butyroxy and isobutyroxy.

For the purposes of the invention, mono-$(C_1-C_6)$-alkylamino and mono-$(C_1-C_4)$-alkylamino represent an amino group having a straight-chain or branched alkyl substituent which has 1 to 6 and 1 to 4 carbon atoms, respectively. Preference is given to a straight-chain or branched monoalkylamino radical having 1 to 4 carbon atoms. The following radicals may be mentioned by way of example and by way of preference: methylamino, ethylamino, n-propylamino, isopropylamino, n-butylamino, tert-butylamino, n-pentylamino and n-hexylamino.

For the purposes of the invention, di-$(C_1-C_6)$-alkylamino and di-$(C_1-C_4)$-alkylamino represent an amino group having two identical or different straight-chain or branched alkyl substituents having 1 to 6 and 1 to 4 carbon atoms, respectively. Preference is given to straight-chain or branched dialkylamino radicals having in each case 1 to 4 carbon atoms. The following radicals may be mentioned by way of example and by way of preference: N,N-dimethylamino, N,N-diethylamino, N-ethyl-N-methylamino, N-methyl-N-n-propylamino, N-isopropyl-N-n-propylamino, N,N-diisopropylamino, N-n-butyl-N-methylamino, N-tert-butyl-N-methylamino, N-ethyl-N-n-pentylamino and N-n-hexyl-N-methylamino.

For the purposes of the invention, mono- and di-$(C_1-C_6)$-alkylaminocarbonyl represent an amino group which is attached via a carbonyl group and which has a straight-chain or branched or two identical or different straight-chain or branched alkyl substituents having in each case 1 to 6 carbon atoms. Preference is given to a mono- or dialkylaminocarbonyl radical having 1 to 4 carbon atoms in the alkyl group. The following radicals may be mentioned by way of example and by way of preference: methylaminocarbonyl, ethylaminocarbonyl, n-propylaminocarbonyl, isopropyl-aminocarbonyl, n-butylaminocarbonyl, tert-butylaminocarbonyl, N,N-dimethylaminocarbonyl, N,N-diethylaminocarbonyl, N-ethyl-N-methylaminocarbonyl, N-methyl-N-n-propylaminocarbonyl, N-n-butyl-N-methylaminocarbonyl and N-tert-butyl-N-methylaminocarbonyl.

For the purposes of the invention, $(C_6-C_{10})$-aryl represents an aromatic carbocycle having 6 or 10 ring carbon atoms. Preferred aryl radicals are phenyl and naphthyl.

For the purposes of the invention, a 4- to 7-membered heterocycle represents a saturated heterocycle having a total of 4 to 7 ring atoms which contains one or two ring heteroatoms from the group consisting of N, O and S and which is attached via a ring carbon atom or, if appropriate, via a ring nitrogen atom. Preference is given to a 5- or 6-membered heterocycle having one or two ring heteroatoms from the group consisting of N and O. The following radicals may be mentioned by way of example: azetidinyl, oxetanyl, pyrrolidinyl, pyrazolidinyl, tetrahydrofuranyl, piperidinyl, piperazinyl, tetrahydropyranyl, morpholinyl, thiomorpholinyl, hexahydroazepinyl and hexahydro-1,4-diazepinyl. Preference is given to pyrrolidinyl, tetrahydrofuranyl, piperidinyl, piperazinyl, tetrahydropyranyl and morpholinyl.

For the purposes of the invention, 5- to 10-membered heteroaryl represents a mono- or, if appropriate, bicyclic aromatic heterocycle (heteroaromatic) having a total of 5 to 10 ring atoms which contains up to three identical or different ring heteroatoms from the group consisting of N, O and S and which is attached via a ring carbon atom, or, if appropriate, via a ring nitrogen atom. The following radicals may be mentioned by way of example: furyl, pyrrolyl, thienyl, pyrazolyl, imidazolyl, thiazolyl, oxazolyl, isoxazolyl, isothiazolyl, triazolyl, oxadiazolyl, thiadiazolyl, pyridyl, pyrimidinyl, pyridazinyl, pyrazinyl, triazinyl, benzofuranyl, benzothienyl, benzimidazolyl, benzoxazolyl, benzothiazolyl, benzotriazolyl, indolyl, indazolyl, quinolinyl, isoquinolinyl, naphthyridinyl, quinazolinyl, quinoxalinyl, phthalazinyl, pyrazolo[3,4-b]pyridinyl. Preference is given to monocyclic 5- or 6-membered heteroaryl radicals having up to three ring heteroatoms from the group consisting of N, O and S, such as, for example, furyl, thienyl, thiazolyl, oxazolyl, isothiazolyl, isoxazolyl, pyrazolyl, imidazolyl, triazolyl, oxadiazolyl, thiadiazolyl, pyridyl, pyrimidinyl, pyridazinyl, pyrazinyl, triazinyl.

For the purposes of the invention, halogen includes fluorine, chlorine, bromine and iodine. Preference is given to chlorine and fluorine.

When radicals in the compounds according to the invention are substituted, the radicals may be mono- or polysubstituted, unless specified otherwise. For the purposes of the present invention, the meanings of all radicals which occur more than once are independent of one another. Preference is given to substitution by one, two or three identical or different substituents. Very particularly preferred is substitution by one or two identical or different substituents.

For the purposes of the present invention, preference is given to compounds of the formula (I) in which
$R^1$ represents phenyl or 5- or 6-membered heteroaryl having up to three ring heteroatoms from the group consisting of N, O and S, each of which radicals is
(i) mono- or disubstituted by identical or different radicals selected from the group consisting of halogen, nitro, cyano, $(C_1-C_6)$-alkyl, trifluoromethyl, hydroxyl, $(C_1-C_6)$-alkoxy, amino, mono-$(C_1-C_6)$-alkylamino, di-$(C_1-C_6)$-alkylamino, carboxyl, $(C_1-C_6)$-alkoxycarbonyl, carbamoyl, mono-$(C_1-C_6)$-alkylaminocarbonyl and di-$(C_1-C_6)$-alkylaminocarbonyl
and/or
(ii) substituted by pyrrolidino, piperidino, morpholino, piperazino, N'—$(C_1-C_4)$-alkylpiperazino, tetrazolyl or a group of the formula -L-$R^4$ in which
L represents a bond, NH or O
and
$R^4$ represents phenyl or 5- or 6-membered heteroaryl having up to three ring heteroatoms from the group consisting of N, O and S, each of which radicals may be mono- to trisubstituted by identical or different radicals selected from the group consisting of halogen, nitro, cyano, $(C_1-C_6)$-alkyl, trifluoromethyl, hydroxyl, $(C_1-C_6)$-alkoxy, difluoromethoxy, trifluoromethoxy, amino, mono-$(C_1-C_6)$-alkylamino, di-$(C_1-C_6)$-alkylamino, $(C_1-C_6)$-alkoxycarbonyl and carboxyl,
or
$R^1$ represents N-oxidopyridyl,
and salts, solvates and solvates of the salts thereof.

In the context of the present invention, preference is given to compounds of the formula (I) in which
ring A represents cyclopentyl, cyclohexyl, cyclopent-2-en-1-yl, cyclopent-3-en-1-yl, cyclohex-2-en-1-yl or cyclohex-3-en-1-yl, represents a 5- or 6-membered heterocycle which is attached via carbon and which contains a ring member from the group consisting of N—$R^3$ and O, or represents a heterocycle of the formula

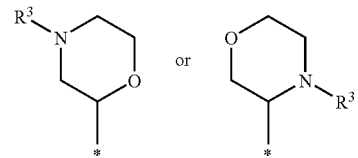

which is attached via carbon and in which
cyclopentyl, cyclohexyl, cyclopentenyl and cyclohexenyl may be mono- or disubstituted by identical or different radicals selected from the group consisting of $(C_1-C_4)$-alkyl, hydroxyl, $(C_1-C_4)$-alkoxy, amino, mono-$(C_1-C_4)$-alkylamino and di-$(C_1-C_4)$-alkylamino, where the $(C_1-C_4)$-alkyl- and $(C_1-C_4)$-alkoxy radicals mentioned for their part may be mono- or disubstituted by identical or different radicals from the group consisting of hydroxyl, $(C_1-C_4)$-alkoxy and $(C_3-C_5)$-cycloalkyl,
* denotes the point of attachment to the pyridine ring
and
$R^3$ represents hydrogen, $(C_1-C_4)$-alkyl which may be mono- or disubstituted by identical or different radicals from the group consisting of hydroxyl, $(C_1-C_4)$-alkoxy, ($C_1$-$C_4$)-acyloxy and ($C_3$-$C_5$)-cycloalkyl, or ($C_1$-$C_4$)-acyl which may be substituted by hydroxyl or ($C_1$-$C_4$)-alkoxy, $R^1$ represents phenyl or 5- or 6-membered heteroaryl having up to three ring heteroatoms from the group consisting of N, O and S, each of which radicals is
  (i) mono- or disubstituted by identical or different radicals selected from the group consisting of fluorine, chlorine, cyano, ($C_1$-$C_4$)-alkyl, amino, mono-($C_1$-$C_4$)-alkylamino, di-($C_1$-$C_4$)-alkylamino, ($C_1$-$C_4$)-alkoxycarbonyl, carboxyl and carbamoyl
  and/or
  (ii) substituted by morpholino, N'—($C_1$-$C_4$)-alkylpiperazino or a group of the formula -L-$R^4$ in which
    L represents a bond or NH
    and
    $R^4$ represents phenyl or 5- or 6-membered heteroaryl having up to three ring heteroatoms from the group consisting of N, O and S, each of which radicals may be mono- to trisubstituted by identical of different radicals selected from the group consisting of fluorine, chlorine, cyano, ($C_1$-$C_4$)-alkyl, trifluoromethyl, ($C_1$-$C_4$)-alkoxy, trifluoromethoxy, ($C_1$-$C_4$)-alkoxycarbonyl and carboxyl,
or
$R^1$ represents N-oxidopyridyl,
and
$R^2$ represents hydrogen or represents ($C_1$-$C_4$)-alkoxy which may be substituted up to three times by fluorine
or
$R^2$ represents a group of the formula —$NR^5R^6$ in which
  $R^5$ represents hydrogen or ($C_1$-$C_4$)-alkyl which may be substituted by hydroxyl, ($C_1$-$C_4$)-alkoxy, amino, mono-($C_1$-$C_4$)-alkylamino, di-($C_1$-$C_4$)-alkylamino, carboxyl, ($C_1$-$C_4$)-alkoxycarbonyl or a 5- or 6-membered heterocycle,
    where the heterocycle mentioned contains one or two ring heteroatoms from the group consisting of N and O and for its part may be mono- or disubstituted by identical or different radicals from the group consisting of methyl, ethyl, hydroxyl, methoxy and ethoxy,
  $R^6$ represents hydrogen or methyl
  or
  $R^5$ and $R^6$ together with the nitrogen atom, to which they are attached form a 5- or 6-membered heterocycle which may contain a further ring heteroatom from the group consisting of N or O and may be mono- or disubstituted by identical or different radicals from the group consisting of methyl, ethyl, hydroxyl, methoxy and ethoxy,
and salts, solvates and solvates of the salts thereof.

In the context of the present invention, particular preference is given to compounds of the formula (I) in which ring A represents a group of the formula

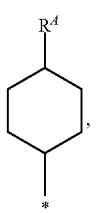 , 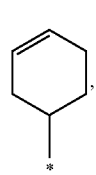 , 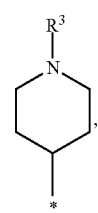 , 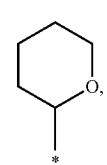 ,

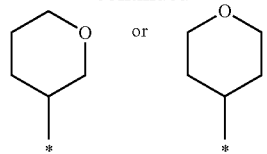

in which
* denotes the point of attachment to the pyridine ring,
$R^A$ represents hydrogen, hydroxyl, methoxy, ethoxy or 2-hydroxyethoxy
and
$R^3$ represents methyl, ethyl, 2-hydroxyethyl, 2-acetoxyethyl, 3-hydroxypropyl, 3-acetoxypropyl or hydroxyacetyl, $R^1$ represents phenyl, oxazolyl, thiazolyl or pyridyl, each of which radicals is
  (i) mono- or disubstituted by identical or different radicals selected from the group consisting of fluorine, chlorine, methyl, amino, methoxycarbonyl, ethoxycarbonyl, carboxyl and carbamoyl
  or
  (ii) substituted by a group of the formula -L-$R^4$ in which
    L represents a bond or NH
    and
    $R^4$ represents phenyl or pyridyl, each of which radicals may be mono- or disubstituted by identical or different radicals selected from the group consisting of fluorine, chlorine, cyano, methyl, methoxy and carboxyl,
and
$R^2$ represents hydrogen, methoxy or a group of the formula —$NR^5R^6$ in which
  $R^5$ represents hydrogen or ($C_1$-$C_4$)-alkyl which may be substituted by hydroxyl, amino, methylamino, ethylamino, dimethylamino, diethylamino or a heterocycle of the formula

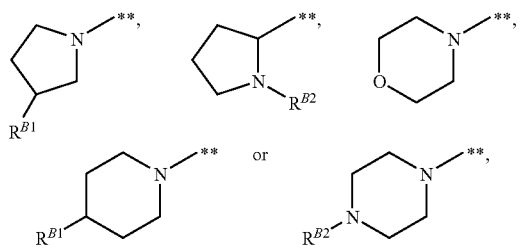

$R^6$ represents hydrogen
or
$R^5$ and $R^6$ together with the nitrogen atom to which they are attached form a group of the formula

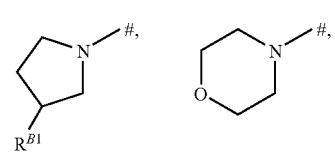

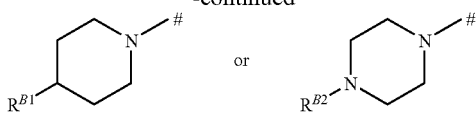

in which in each case

** denotes the point of attachment to the $(C_1-C_4)$-alkyl radical, # denotes the point of attachment to the pyridine ring, $R^{B1}$ represents hydrogen or hydroxyl and $R^{B2}$ represents hydrogen or methyl, and salts, solvates and solvates of the salts thereof.

The present invention furthermore provides a process for preparing the compounds of the formula (I) according to the invention in which $R^2$ represents $NH_2$, characterized in that a compound of the formula (II)

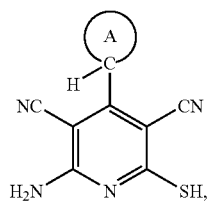

(II)

in which ring A has the meaning given above,
is reacted in an inert solvent in the presence of a base with a compound of the formula (III)

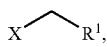

(III)

in which $R^1$ has the meaning given above and

X represents a suitable leaving group, preferably halogen, in particular chlorine, bromine or iodine, or represents mesylate, tosylate or triflate, to give a compound of the formula (I-A)

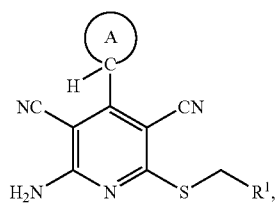

(I-A)

in which $R^1$ and ring A have the meanings given above,
and the compounds of the formula (I-A) are, if appropriate, converted with the appropriate (i) solvents and/or (ii) bases or acids into their solvates, salts and/or solvates of the salts.

The process described above can be illustrated by the reaction scheme below:

Scheme 1

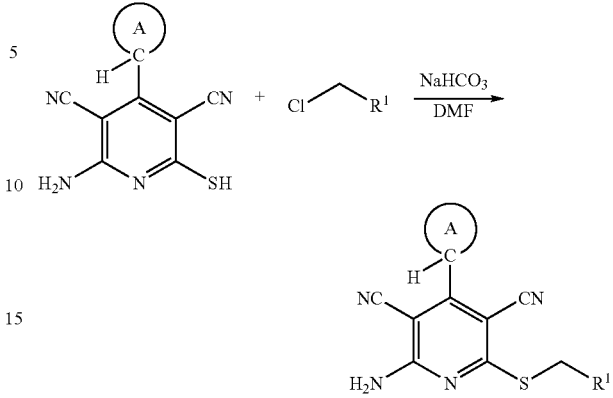

Solvents suitable for the process according to the invention are all organic solvents which are inert under the reaction conditions. These include alcohols, such as methanol, ethanol, n-propanol, isopropanol, n-butanol and tert-butanol, ketones, such as acetone and methyl ethyl ketone, acyclic and cyclic ethers, such as diethyl ether, methyl tert-butyl ether, 1,2-dimethoxyethane, tetrahydrofuran and dioxane, esters, such as ethyl acetate or butyl acetate, hydrocarbons, such as benzene, toluene, xylene, hexane and cyclohexane, chlorinated hydrocarbons, such as dichloromethane, trichloromethane and chlorobenzene, or other solvents, such as dimethyl-formamide (DMF), dimethyl sulfoxide (DMSO), N-methylpyrrolidinone (NMP), acetonitrile or pyridine. Another suitable solvent is water. It is also possible to use mixtures of the solvents mentioned above. Preferred for use as solvent is dimethylformamide.

Bases suitable for the reaction (II)+(III)→(I-A) are the customary inorganic or organic bases. These preferably include alkali metal hydroxides, such as, for example, lithium hydroxide, sodium hydroxide or potassium hydroxide, alkali metal carbonates, such as lithium carbonate, sodium carbonate, potassium carbonate or cesium carbonate, alkali metal bicarbonates, such as sodium bicarbonate or potassium bicarbonate, alkali metal alkoxides, such as sodium methoxide or potassium methoxide, sodium ethoxide or potassium ethoxide or potassium tert-butoxide, amides, such as sodium amide, lithium bis-(trimethylsilyl)amide, sodium bis-(trimethylsilyl)amide or potassium bis-(trimethylsilyl)amide or lithium diisopropylamide, organometallic compounds, such as butyllithium or phenyllithium, or organic amines, such as triethylamine, diisopropylethylamine, pyridine, 1,8-diazabicyclo[5.4.0]undec-7-ene (DBU) or 1,5-diazabicyclo[4.3.0]non-5-ene (DBN). Preference is given to alkali metal carbonates and alkali metal bicarbonates.

Here, the base can be employed in an amount of from 1 to 10 mol, preferably from 1 to 5 mol, in particular from 1 to 4 mol, per mole of the compound of the formula (II).

In general, the reaction is carried out in a temperature range of from −78° C. to +140° C., preferably in the range of from −20° C. to +80° C., in particular at from 0° C. to +50° C. The reaction can be carried out at atmospheric, elevated or reduced pressure (for example in the range of from 0.5 to 5 bar). In general, the reaction is carried out at atmospheric pressure.

The compounds of the formula (II) can be prepared analogously to methods known from the literature, for example by reacting aldehydes of the formula (IV)

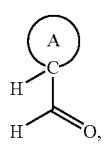
(IV)

in which ring A has the meaning given above,
in the presence of a base with two equivalents of cyanothioacetamide [see Scheme 2; cf., for example, Dyachenko et al., *Russ. J. Chem.* 33 (7), 1014-1017 (1997), 34 (4), 557-563 (1998); Dyachenko et al., *Chemistry of Heterocyclic Compounds* 34 (2), 188-194 (1998); Qintela et al., *Eur. J. Med. Chem.* 33, 887-897 (1998); Kandeel et al., *Z. Naturforsch.* 42b, 107-111 (1987); Reddy et al., *J. Med. Chem.* 49, 607-615 (2006); Evdokimov et al., *Org. Lett.* 8, 899-902 (2006)].

Scheme 2

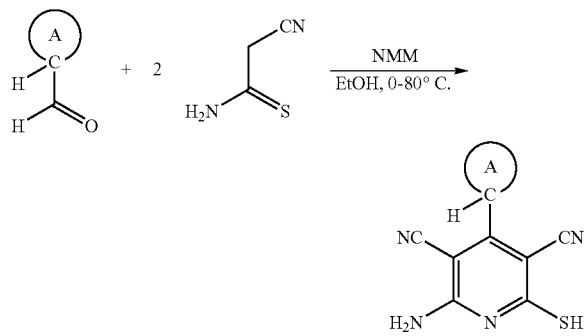

[EtOH=ethanol, NMM=N-methylmorpholine].

Alternatively, compounds of the formula (II) can also be prepared from compounds of the formula (V)

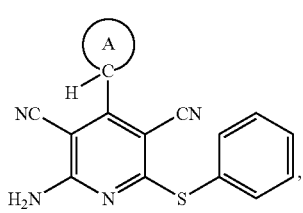
(V)

in which ring A has the meaning given above,
by reaction with an alkali metal sulfide. This preparation method can be illustrated in an exemplary manner by the formula scheme below:

Scheme 3

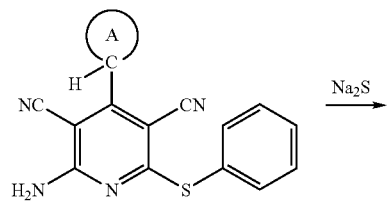

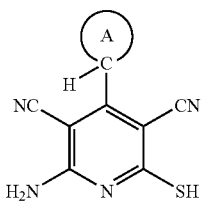

The alkali metal sulfide used is preferably sodium sulfide in an amount of from 1 to 10 mol, preferably from 1 to 5 mol, in particular from 1 to 4 mol per mole of the compound of the formula (V).

Solvents suitable for this purpose are all organic solvents which are inert under the reaction conditions. These include in particular dimethylformamide, N-methylpyrrolidinone, pyridine and acetonitrile. It is also possible to use mixtures of the solvents mentioned above. Preference is given to using dimethylformamide.

In general, the reaction is carried out in a temperature range of from +20° C. to +140° C., preferably in the range of from +20° C. to +120° C., in particular at from +60° C. to +100° C. The reaction can be carried out at atmospheric, elevated or reduced pressure (for example in the range of from 0.5 to 5 bar). In general, the reaction is carried out at atmospheric pressure.

The compounds of the formula (V) can be prepared analogously to processes described in the literature [cf., for example, Kambe et al., *Synthesis,* 531-533 (1981); Elnagdi et al., *Z. Naturforsch.* 47b, 572-578 (1991); Reddy et al., *J. Med. Chem.* 49, 607-615 (2006); Evdokimov et al., *Org. Lett.* 8, 899-902 (2006)].

The compounds of the formula (III) are commercially available, known from the literature or can be prepared by methods known from the literature. Thus, for example, substituted oxazole and thiazole derivatives of the formulae (III-A), (III-B) and (III-C) are obtained by reacting amides, thioamides and thiourea derivatives, respectively, with a 1,3-dihaloacetone (see Scheme 4):

Scheme 4

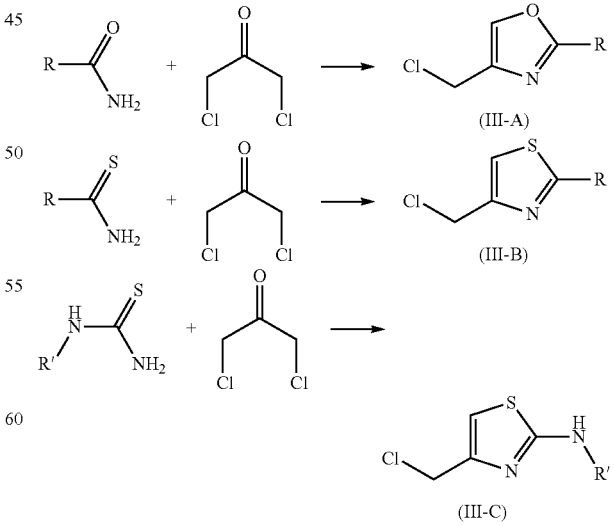

In the case of the compounds (III-C), these can either be prepared and isolated analogously to the literature [cf., for example, I. Simiti et al., *Chem. Ber.* 95, 2672-2679 (1962)], or they can be generated in situ and directly reacted further with a compound of the formula (II). Preference is given to the in situ generation using 1,3-dichloroacetone in dimethylformamide or ethanol as solvent. The preparation is generally carried out in a temperature range of from 0° C. to +140° C., preferably in the range of from +20° C. to +120° C., in particular at from +60° C. to +100° C.

The aldehydes of the formula (IV) are commercially available, have been described in the literature or can be prepared by standard methods from known starting materials.

The present invention furthermore provides a process for preparing the compounds of the formula (I) according to the invention in which $R^2$ represents the group $—NR^5R^6$ and in which at least one of the two radicals $R^5$ and $R^6$ is not hydrogen, characterized in that compounds of the formula (I-A) are initially converted with copper(II) chloride and isoamyl nitrite in a suitable solvent into compounds of the formula (VI)

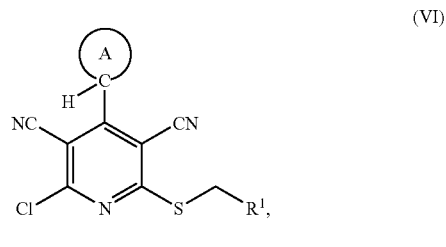

(VI)

in which $R^1$ and ring A have the meanings given above, and these are then reacted with a compound of the formula (VII)

(VII)

in which
$R^{5A}$ has the meaning of $R^5$ given above,
$R^{6A}$ has the meaning of $R^6$ given above,
but at least one of the two radicals $R^{5A}$ and $R^{6A}$ does not represent hydrogen, to give compounds of the formula (I-B)

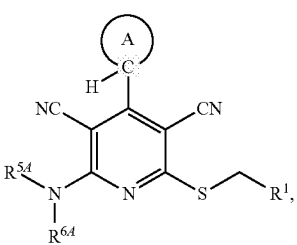

(I-B)

in which $R^1$, $R^{5A}$, $R^{6A}$ and ring A each have the meanings given above,
and the compounds of the formula (I-B) are, if appropriate, converted with the appropriate (i) solvents and/or (ii) bases or acids into their solvates, salts and/or solvates of the salts.

The process described above can be illustrated by the reaction scheme below:

Scheme 5

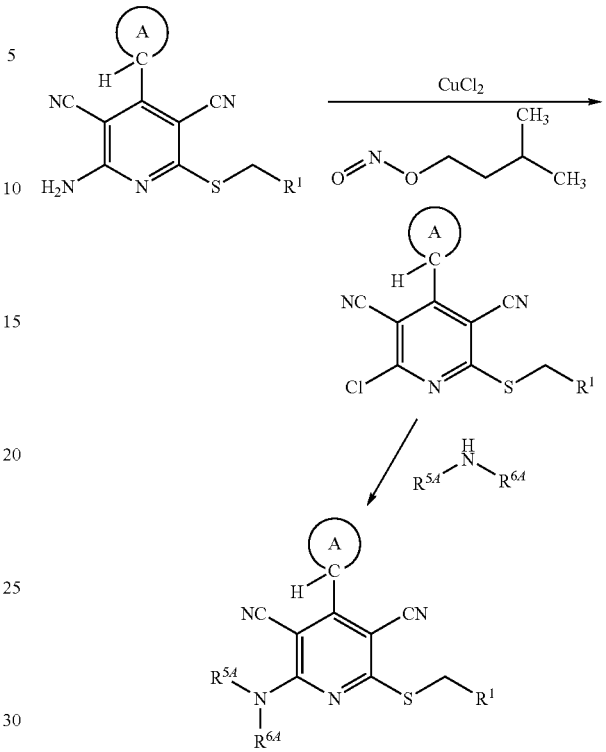

The reaction (I-A)→(VI) is generally carried out in a molar ratio of from 2 to 12 mol of copper(II) chloride and 2 to 12 mol of isoamyl nitrite per mole of the compound of the formula (I-A).

Solvents suitable for the process step (I-A)→(VI) are all organic solvents which are inert under the reaction conditions. These include acyclic and cyclic ethers, such as diethyl ether and tetrahydrofuran, esters, such as ethyl acetate or butyl acetate, hydrocarbons, such as benzene, toluene, xylene, hexane and cyclohexane, chlorinated hydrocarbons, such as dichloromethane, 1,2-dichloroethane and chlorobenzene, or other solvents, such as dimethylformamide, acetonitrile or pyridine. It is also possible to use mixtures of the solvents mentioned above. Preferred solvents are acetonitrile and dimethylformamide.

In general, the reaction is carried out in a temperature range of from −78° C. to +180° C., preferably in the range of from 0° C. to +100° C., in particular at from +20° C. to +80° C. The reaction can be carried out at atmospheric, elevated or reduced pressure (for example in the range of from 0.5 to 5 bar). In general, the reaction is carried out at atmospheric pressure.

The reaction (VI)+(VII)→(I-B) is generally carried out using a molar ratio of from 1 to 8 mol of the compound of the formula (VII) per mole of the compound of the formula (VI).

Solvents suitable for the process step (VI)+(VII)→(I-B) are all organic solvents which are inert under the reaction conditions. These include alcohols, such as methanol, ethanol, n-propanol, iso-propanol, n-butanol and tert-butanol, ketones, such as acetone and methyl ethyl ketone, acyclic and cyclic ethers, such as diethyl ether, 1,2-dimethoxyethane, tetrahydrofuran and dioxane, esters, such as ethyl acetate or butyl acetate, hydrocarbons, such as benzene, toluene, xylene, hexane and cyclohexane, chlorinated hydrocarbons, such as dichloromethane, 1,2-dichloroethane and chlorobenzene, or other solvents, such as dimethylformamide, acetonitrile, pyridine or dimethyl sulfoxide. Another suitable solvent is water. It is also possible to use mixtures of the solvents mentioned above. The preferred solvent is dimethylformamide.

In general, the reaction is carried out in a temperature range of from 0° C. to +180° C., preferably in the range of from +20° C. to +150° C., in particular at from +20° C. to +100° C. The reaction can be carried out at atmospheric, elevated or reduced pressure (for example in the range of from 0.5 to 5 bar). In general, the reaction is carried out at atmospheric pressure.

The compounds of the formula (VII) are either commercially available, known to the person skilled in the art or can be prepared by customary methods.

The compounds of the formula (I) according to the invention in which $R^2$ represents hydrogen can be prepared by reacting compounds of the formula (I-A) in a suitable solvent with isoamyl nitrite in the presence of a catalytic amount of copper(II) chloride. This method can be illustrated by the reaction scheme below:

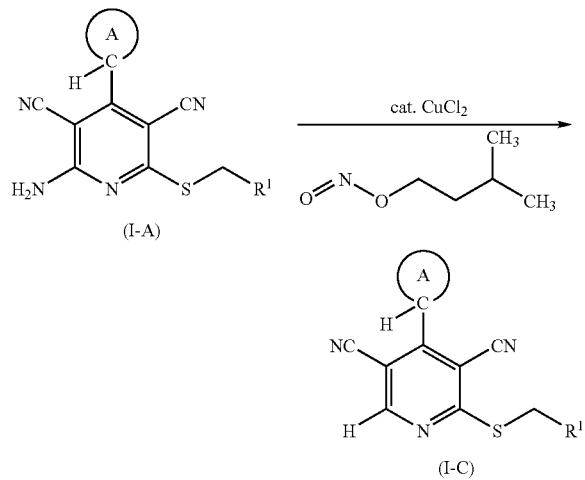

The reaction (I-A)→(I-C) is generally carried out in a molar ratio of from 0.01 to 0.2 mol of copper(II) chloride and from 2 to 12 mol of isoamyl nitrite per mole of the compound of the formula (I-A).

Solvents suitable for the reaction (I-A)→(I-C) are all organic solvents which are inert under the reaction conditions. These include acyclic and cyclic ethers, such as diethyl ether and tetrahydrofuran, esters, such as ethyl acetate or butyl acetate, hydrocarbons, such as benzene, toluene, xylene, hexane and cyclohexane, chlorinated hydrocarbons, such as dichloromethane, 1,2-dichloroethane and chlorobenzene, or other solvents, such as dimethylformamide, acetonitrile or pyridine. It is also possible to use mixtures of the solvents mentioned. Preferred solvents are tetrahydrofuran and dimethylformamide.

In general, the reaction is carried out in a temperature range of from −78° C. to +150° C., preferably in the range of from 0° C. to +80° C., in particular at from +10° C. to +40° C. The reaction can be carried out at atmospheric, elevated or reduced pressure (for example in the range of from 0.5 to 5 bar). In general, the reaction is carried out at atmospheric pressure.

The compounds of the formula (I) according to the invention in which $R^2$ represents optionally substituted $(C_1-C_6)$-alkyl or $(C_1-C_6)$-alkoxy can be prepared analogously to methods described in the literature from compounds of the formula (VI) [cf., for example, D. Mabire et al., J. Med. Chem. 48, 2134-2153 (2005)]. Alternatively, the compounds of the formula (I) in which $R^2$ represents optionally substituted $(C_1-C_6)$-alkoxy can also be obtained by alkylation of compounds of the formula (VIII) (see Scheme 7):

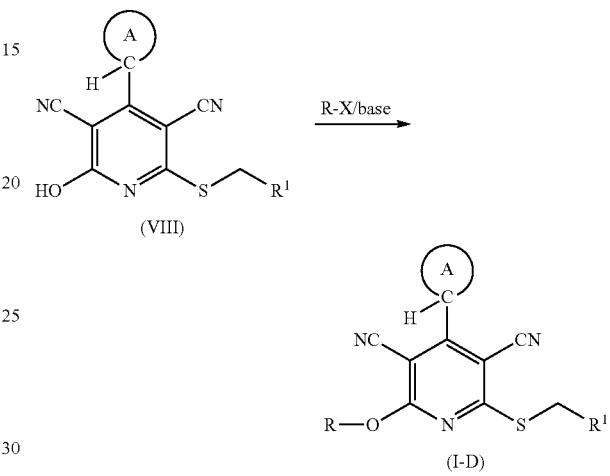

For their part, the compounds of the formula (VIII) can be obtained by methods known from the literature from compounds of the formula (VI) or (I-A) [cf., for example, G. Lavecchia et al., Tetrahedron Lett. 45, 6633-6636 (2004)].

Further compounds according to the invention can, if appropriate, also be prepared by converting functional groups of individual radicals and substituents, in particular those listed under $R^1$ and $R^2$ and for ring A, starting with compounds of the formula (I) obtained by the above processes. These conversions are carried out using customary methods known to the person skilled in the art and include, for example, reactions such as nucleophilic or electrophilic substitution, oxidation, reduction, hydrogenation, alkylation, acylation, amination, formation of carboxamides and carboxylic esters, ester hydrolysis, etherification, ether cleavage and also the introduction and removal of temporary protective groups.

Surprisingly, the compounds according to the invention have an unforeseeable useful pharmacological activity spectrum and are therefore particularly suitable for the prophylaxis and/or treatment of disorders. In addition, the substances according to the invention have, compared to the compounds of the prior art, an improved resorption behavior in the body and/or improved solubility in water and other physiological media, which is advantageous, for example, for their ease of galenic formulation and/or parenteral administration.

The pharmacological activity of the compounds according to the invention can be explained by their action as potent, selective ligands at adenosine A1 and/or A2b receptors. Here, they act as selective A1 agonists or as selective dual A1/A2b agonists.

In the context of the present invention, "selective ligands at adenosine A1 and/or A2b receptors" are adenosine receptor ligands where firstly a marked activity at A1 and/or A2b adenosine receptor subtypes and secondly no or a considerably weaker activity (by a factor of 10 or more) at A2a and A3 adenosine receptor subtypes can be observed, where with respect to the test methods for activity/selectivity, reference is made to the tests described in section B-1.

The compounds of the formula (I), on their own or in combination with one or more other active compounds, are suitable for the prophylaxis and/or treatment of various disorders such as, for example, in particular hypertension and other disorders of the cardiovascular system (cardiovascular disorders), and for cardioprotection.

In the context of the present invention, disorders of the cardiovascular system or cardiovascular disorders are to be understood as including, in addition to hypertension, for example in particular the following disorders: peripheral and cardial vascular disorders, coronary heart disease, coronary restenosis, such as, for example, restenosis after balloon dilation of peripheral blood vessels, acute coronary syndrome, stable and unstable angina pectoris, heart failure, tachycardias, arrhythmias, atrial and ventricular fibrillation and impaired peripheral circulation.

The compounds according to the invention are furthermore also particularly suitable for reducing the myocard region affected by an infarct, and also for the prophylaxis of secondary infarcts.

Furthermore, compounds according to the invention are particularly suitable for the prophylaxis and/or treatment of thromboembolic disorders and ischemias, such as myocardial infarction, stroke and transitory ischemic attacks, and also for organ protection during transplantations and surgical interventions, for example on the heart.

Further indications for which the compounds according to the invention may be used are, for example, in particular the prophylaxis and/or treatment of disorders of the urogenital system, such as, for example, in irritable bladder, erectile dysfunction and female sexual dysfunction, but in addition also the prophylaxis and/or treatment of inflammatory disorders, such as, for example, asthma and inflammatory dermatoses, of neuroinflammatory disorders of the central nervous system such as, for example, conditions following stroke, Alzheimer's disease and furthermore of neurodegenerative disorders, and also of pain, neoplastic diseases and nausea and emesis associated with cancer therapies.

A further indication is, for example, in particular the prophylaxis and/or treatment of disorders of the respiratory tract, such as, for example, asthma, chronic bronchitis, pulmonary emphysema, bronchiectasias, cystic fibrosis (mucoviscidosis) and pulmonary hypertension.

Finally, the compounds according to the invention are also suitable, for example, in particular for the prophylaxis and/or treatment of diabetes mellitus, diabetic sequelae, such as, for example, nephropathy and neuropathy, metabolic syndrome and also dyslipidemias.

The present invention furthermore provides the use of the compounds according to the invention for the treatment and/or prophylaxis of disorders, in particular the disorders mentioned above.

The present invention also provides the use of the compounds according to the invention for preparing a medicament for the treatment and/or prophylaxis of disorders, in particular the disorders mentioned above.

The present invention also provides a method for the treatment and/or prophylaxis of disorders, in particular the disorders mentioned above, using an effective amount of at least one compound according to the invention.

The compounds according to the invention can be used alone or, if required, in combination with other active compounds. The present invention furthermore provides medicaments comprising at least one compound according to the invention and one or more further active compounds, in particular for the treatment and/or of the disorders mentioned above.

Suitable active compound combinations are, by way of example and by way of preference: active compounds which modulate lipid metabolism, antidiabetics, hypotensive agents, perfusion-enhancing and/or antithrombotic agents, antioxidants, chemokine receptor antagonists, p38-kinase inhibitors, NPY agonists, orexin agonists, anorectics, PAF-AH inhibitors, antiphlogistics (COX inhibitors, $LTB_4$-receptor antagonists) and analgesics such as, for example, aspirin.

The present invention provides in particular combinations comprising at least one of the compounds according to the invention and at least one lipid metabolism-modulating active compound, an antidiabetic, a hypotensive active compound and/or an antithrombotic agent.

Preferably, the compounds according to the invention can be combined with one or more lipid metabolism-modulating active compounds, by way of example and by way of preference from the group of the HMG-CoA reductase inhibitors, inhibitors of HMG-CoA reductase expression, squalene synthesis inhibitors, ACAT inhibitors, LDL receptor inductors, cholesterol absorption inhibitors, polymeric bile acid adsorbers, bile acid reabsorption inhibitors, MTP inhibitors, lipase inhibitors, LpL activators, fibrates, niacin, CETP inhibitors, PPAR-α, PPAR-γ and/or PPAR-δ agonists, RXR modulators, FXR modulators, LXR modulators, thyroid hormones and/or thyroid mimetics, ATP citrate lyase inhibitors, Lp(a) antagonists, cannabinoid receptor 1 antagonists, leptin receptor agonists, bombesin receptor agonists, histamine receptor agonists and the antioxidants/radical scavengers;

antidiabetics mentioned in the Rote Liste 2004/II, chapter 12, and also, by way of example and by way of preference, those from the group of the sulfonylureas, biguanides, meglitinide derivatives, glucosidase inhibitors, oxadiazolidinones, thiazolidinediones, GLP 1 receptor agonists, glucagon antagonists, insulin sensitizers, CCK 1 receptor agonists, leptin receptor agonists, inhibitors of liver enzymes involved in the stimulation of gluconeogenesis and/or glycogenolysis, modulators of glucose uptake and also potassium channel openers, such as, for example, those disclosed in WO 97/26265 and WO 99/03861;

hypotensive active compounds, by way of example and by way of preference from the group of the calcium antagonists, angiotensin AII antagonists, ACE inhibitors, renin inhibitors, beta-receptor blockers, alpha-receptor blockers, diuretics, phosphodiesterase inhibitors, sGC stimulators, substances which increase the cGMP concentration, aldosterone antagonists, mineralocorticoid receptor antagonists, ECE inhibitors and the vasopeptidase inhibitors; and/or antithrombotic agents, by way of example and by way of preference from the group of the platelet aggregation inhibitors or the anticoagulants.

Lipid metabolism-modifying active compounds are to be understood as meaning, preferably, compounds from the group of the HMG-CoA reductase inhibitors, squalene synthesis inhibitors, ACAT inhibitors, cholesterol absorption inhibitors, MTP inhibitors, lipase inhibitors, thyroid hormones and/or thyroid mimetics, niacin receptor agonists, CETP inhibitors, PPAR-α agonists PPAR-γ agonists, PPAR-δ agonists, polymeric bile acid adsorbers, bile acid reabsorption inhibitors, antioxidants/radical scavengers and also the cannabinoid receptor 1 antagonists.

In a preferred embodiment of the invention, the compounds according to the invention are administered in combination with an HMG-CoA reductase inhibitor from the class of the statins, such as, by way of example and by way of preference, lovastatin, simvastatin, pravastatin, fluvastatin, atorvastatin, rosuvastatin, cerivastatin or pitavastatin.

In a preferred embodiment of the invention, the compounds according to the invention are administered in combination with a squalene synthesis inhibitor, such as, by way of example and by way of preference, BMS-188494 or TAK-475.

In a preferred embodiment of the invention, the compounds according to the invention are administered in combination with an ACAT inhibitor, such as, by way of example and by way of preference, avasimibe, melinamide, pactimibe, eflucimibe or SMP-797.

In a preferred embodiment of the invention, the compounds according to the invention are administered in combination with a cholesterol absorption inhibitor, such as, by way of example and by way of preference, ezetimibe, tiqueside or pamaqueside.

In a preferred embodiment of the invention, the compounds according to the invention are administered in combination with an MTP inhibitor, such as, by way of example and by way of preference, implitapide, BMS-201038, R-103757 or JTT-130.

In a preferred embodiment of the invention, the compounds according to the invention are administered in combination with a lipase inhibitor, such as, by way of example and by way of preference, orlistat.

In a preferred embodiment of the invention, the compounds according to the invention are administered in combination with a thyroid hormone and/or thyroid mimetic, such as, by way of example and by way of preference, D-thyroxine or 3,5,3'-triiodothyronine (T3).

In a preferred embodiment of the invention, the compounds according to the invention are administered in combination with an agonist of the niacin receptor, such as, by way of example and by way of preference, niacin, acipimox, acifran or radecol.

In a preferred embodiment of the invention, the compounds according to the invention are administered in combination with a CETP inhibitor, such as, by way of example and by way of preference, torcetrapib, JTT-705, BAY 60-5521, BAY 78-7499 or CETP vaccine (Avant).

In a preferred embodiment of the invention, the compounds according to the invention are administered in combination with a PPAR-γ agonist, such as, by way of example and by way of preference, pioglitazone or rosiglitazone.

In a preferred embodiment of the invention, the compounds according to the invention are administered in combination with a PPAR-δ agonist, such as, by way of example and by way of preference, GW-501516 or BAY 68-5042.

In a preferred embodiment of the invention, the compounds according to the invention are administered in combination with a polymeric bile acid adsorber, such as, by way of example and by way of preference, cholestyramine, colestipol, colesolvam, CholestaGel or colestimide.

In a preferred embodiment of the invention, the compounds according to the invention are administered in combination with a bile acid reabsorption inhibitor, such as, by way of example and by way of preference, ASBT (=IBAT) inhibitors, such as, for example, AZD-7806, S-8921, AK-105, BARI-1741, SC-435 or SC-635.

In a preferred embodiment of the invention, the compounds according to the invention are administered in combination with an antioxidant/radical scavenger, such as, by way of example and by way of preference, probucol, AGI-1067, BO-653 or AEOL-10150.

In a preferred embodiment of the invention, the compounds according to the invention are administered in combination with a cannabinoid receptor 1 antagonist, such as, by way of example and by way of preference, rimonabant or SR-147778.

Antidiabetics are to be understood as meaning, preferably, insulin and insulin derivatives, and also orally effective hypoglycemic active compounds. Here, insulin and insulin derivatives include both insulins of animal, human or biotechnological origin and also mixtures thereof. The orally effective hypoglycemic active compounds preferably include sulfonylureas, biguanides, meglitinide derivatives, glucosidase inhibitors and PPAR-γ agonists.

In a preferred embodiment of the invention, the compounds according to the invention are administered in combination with insulin.

In a preferred embodiment of the invention, the compounds according to the invention are administered in combination with a sulfonylurea, such as, by way of example and by way of preference, tolbutamide, glibenclamide, glimepiride, glipizide or gliclazide.

In a preferred embodiment of the invention, the compounds according to the invention are administered in combination with a biguanide, such as, by way of example and by way of preference, metformin.

In a preferred embodiment of the invention, the compounds according to the invention are administered in combination with a meglitinide derivative, such as, by way of example and by way of preference, repaglinide or nateglinide.

In a preferred embodiment of the invention, the compounds according to the invention are administered in combination with a glucosidase inhibitor, such as, by way of example and by way of preference, miglitol or acarbose.

In a preferred embodiment of the invention, the compounds according to the invention are administered in combination with a PPAR-γ agonist, for example from the class of the thiazolidinediones, such as, by way of example and by way of preference, pioglitazone or rosiglitazone.

The hypotensive agents are preferably understood as meaning compounds from the group of the calcium antagonists, angiotensin AII antagonists, ACE inhibitors, beta-receptor blockers, alpha-receptor blockers and diuretics.

In a preferred embodiment of the invention, the compounds according to the invention are administered in combination with a calcium antagonist, such as, by way of example and by way of preference, nifedipine, amlodipine, verapamil or diltiazem.

In a preferred embodiment of the invention, the compounds according to the invention are administered in combination with an angiotensin AII atagonist, such as, by way of example and by way of preference, losartan, valsartan, candesartan, embusartan, almesartan or telmisartan.

In a preferred embodiment of the invention, the compounds according to the invention are administered in combination with an ACE inhibitor, such as, by way of example and by way of preference, enalapril, captopril, lisinopril, ramipril, delapril, fosinopril, quinopril, perindopril or trandopril.

In a preferred embodiment of the invention, the compounds according to the invention are administered in combination with a beta-receptor blocker, such as, by way of example and by way of preference, propranolol, atenolol, timolol, pindolol, alprenolol, oxprenolol, penbutolol, bupranolol, metipranolol, nadolol, mepindolol, carazalol, sotalol, metoprolol, betaxolol, celiprolol, bisoprolol, carteolol, esmolol, labetalol, carvedilol, adaprolol, landiolol, nebivolol, epanolol or bucindolol.

In a preferred embodiment of the invention, the compounds according to the invention are administered in combination with an alpha-receptor blocker, such as, by way of example and by way of preference, prazosin.

In a preferred embodiment of the invention, the compounds according to the invention are administered in combination with a diuretic, such as, by way of example and by way of preference, furosemide, bumetanide, torsemide, bendroflumethiazide, chlorothiazide, hydrochlorothiazide, hydroflumethiazide, methyclothiazide, polythiazide, trichloromethiazide, chlorothalidone, indapamide, metolazone, quinethazone, acetazolamide, dichlorophenamide, methazolamide, glycerol, isosorbide, mannitol, amiloride or triamteren.

In a preferred embodiment of the invention, the compounds according to the invention are administered in combination with antisympathotonics, such as reserpine, clonidine or alpha-methyldopa, or in combination with potassium channel agonists, such as minoxidil, diazoxide, dihydralazine or hydralazine, or with substances which release nitrogen oxide, such as glycerol nitrate or sodium nitroprusside.

Antithrombotics are to be understood as meaning, preferably, compounds from the group of the platelet aggregation inhibitors or the anticoagulants.

In a preferred embodiment of the invention, the compounds according to the invention are administered in combination with a platelet aggregation inhibitor, such as, by way of example and by way of preference, aspirin, clopidogrel, ticlopidine or dipyridamol.

In a preferred embodiment of the invention, the compounds according to the invention are administered in combination with a thrombin inhibitor, such as, by way of example and by way of preference, ximelagatran, melagatran, bivalirudin or clexane.

In a preferred embodiment of the invention, the compounds according to the invention are administered in combination with a GPIIb/IIIa antagonist, such as, by way of example and by way of preference, tirofiban or abciximab.

In a preferred embodiment of the invention, the compounds according to the invention are administered in combination with a factor Xa inhibitor, such as, by way of example and by way of preference, rivaroxaban (BAY 59-7939), DU-176b, apixaban, otamixaban, fidexaban, razaxaban, fondaparinux, idraparinux, PMD-3112, YM-150, KFA-1982, EMD-503982, MCM-17, MLN-1021, DX 9065a, DPC 906, JTV 803, SSR-126512 or SSR-128428.

In a preferred embodiment of the invention, the compounds according to the invention are administered in combination with heparin or a low molecular weight (LMW) heparin derivative.

In a preferred embodiment of the invention, the compounds according to the invention are administered in combination with a vitamin K antagonist, such as, by way of example and by way of preference, coumarin.

The present invention furthermore provides medicaments comprising at least one compound according to the invention, usually together with one or more inert nontoxic pharmaceutically suitable auxiliaries, and also their use for the purposes mentioned above.

The compounds according to the invention can act systemically and/or locally. For this purpose, they can be administered in a suitable manner, such as, for example, orally, parenterally, pulmonally, nasally, sublingually, lingually, buccally, rectally, dermally, transdermally, conjunctivally, optically or as an implant or stent.

For these administration routes, the compounds according to the invention can be administered in suitable administration forms.

Suitable for oral administration are administration forms which work in accordance with the prior art and release the compounds according to the invention rapidly and/or in modified form and which comprise the compounds according to the invention in crystalline and/or amorphicized and/or dissolved form, such as, for example, tablets (uncoated or coated tablets, for example with enteric coats or coats which dissolve in a delayed manner or are insoluble and which control the release of the compound according to the invention), films/wafers or tablets which dissolve rapidly in the oral cavity, films/lyophilizates, capsules (for example hard or soft gelatin capsules), sugar-coated tablets, granules, pellets, powders, emulsions, suspensions, aerosols or solutions.

Parenteral administration may take place by circumventing a bioabsorption step (for example intravenously, intraarterially, intracardially, intraspinally or intralumbarly), or with bioabsorption (for example intramuscularly, subcutaneously, intracutaneously, percutaneously or intraperitoneally). Administration forms suitable for parenteral administration are inter alia preparations for injection or infusion in the form of solutions, suspensions, emulsions, lyophilizates or sterile powders.

Suitable for other administration routes are, for example, medicaments suitable for inhalation (inter alia powder inhalers, nebulizers), nose drops, solutions or sprays, tablets to be administered lingually, sublingually or buccally, films/wafers or capsules, suppositories, preparations to be administered to ears or eyes, vaginal capsules, aqueous suspensions (lotions, shaking mixtures), lipophilic suspensions, ointments, creams, transdermal therapeutic systems (for example plasters), milk, pastes, foams, powders for pouring, implants or stents.

Preference is given to oral or parenteral administration, in particular to oral and intravenous administration.

The compounds according to the invention can be converted into the administration forms mentioned. This can be carried out in a manner known per se by mixing with inert non-toxic pharmaceutically suitable auxiliaries. These auxiliaries include inter alia carriers (for example microcrystalline cellulose, lactose, mannitol), solvents (for example liquid polyethylene glycols), emulsifiers and dispersants or wetting agents (for example sodium dodecyl sulfate, polyoxysorbitan oleate), binders (for example polyvinylpyrrolidone), synthetic and natural polymers (for example albumin), stabilizers (for example antioxidants, such as, for example, ascorbic acid), colorants (for example inorganic pigments, such as, for example, iron oxides), and flavor and/or odor corrigents.

In general, it has been found to be advantageous in the case of parenteral administration to administer amounts of about 0.001 to 1 mg/kg, preferably about 0.01 to 0.5 mg/kg of body weight to obtain effective results. In the case of oral administration, the dosage is from about 0.01 to 100 mg/kg, preferably from about 0.01 to 20 mg/kg and very particularly preferably from 0.1 to 10 mg/kg of body weight.

In spite of this, it may be necessary to deviate from the amounts mentioned, namely depending on body weight, administration route, individual response to the active compound, the type of preparation and the time or the interval at which administration takes place. Thus, in some cases it may be sufficient to administer less than the abovementioned minimum amount, whereas in other cases the upper limit mentioned has to be exceeded. In the case of the administration of relatively large amounts, it may be expedient to divide these into a plurality of individual doses which are administered over the course of the day.

The working examples below illustrate the invention. The invention is not limited to the examples.

The percentages in the tests and examples below are, unless indicated otherwise, percentages by weight; parts are parts by weight. Solvent ratios, dilution ratios and concentrations of liquid/liquid solutions are in each case based on volume.

A. EXAMPLES

| Abbreviations used: | |
|---|---|
| Ex. | example |
| c | concentration |
| TLC | thin-layer chromatography |
| DCI | direct chemical ionization (in MS) |
| DMF | N,N-dimethylformamide |
| DMSO | dimethyl sulfoxide |
| ee | enantiomeric excess |
| EI | electron impact ionization (in MS) |
| ent | enantiomer/enantiomerically pure |
| ESI | electrospray ionization (in MS) |
| Et | ethyl |
| m.p. | melting point |
| GC-MS | gas chromatography-coupled mass spectrometry |
| h | hour(s) |
| HPLC | high-pressure, high-performance liquid chromatography |
| cat. | catalytic |
| conc. | concentrated |
| LC-MS | liquid chromatography-coupled mass spectrometry |
| lit. | literature (reference) |
| min | minute(s) |
| MS | mass spectrometry |
| NMR | nuclear magnetic resonance spectrometry |
| rac. | racemic |
| RP-HPLC | reversed-phase HPLC |
| RT | room temperature |
| $R_t$ | retention time (in HPLC) |
| TBME | tert-butyl methyl ether |
| TFA | trifluoroacetic acid |
| THF | tetrahydrofuran |
| dil. | dilute |
| aq. | aqueous |

HPLC, LC-MS and GC-MS methods:

Method 1 (HPLC):

Instrument: Hewlett Packard Series 1050; column: Symmetry™ C18 3.9×150 mm; flow rate: 1.5 ml/min; mobile phase A: water, mobile phase B: acetonitrile; gradient: →0.6 min 10% B→3.8 min 100% B→5.0 min 100% B→5.5 min 10% B; stop time: 6.0 min; injection volume: 10 µl; diode array detector signal: 214 and 254 nm.

Method 2 (LC-MS):

MS instrument type: Micromass ZQ; HPLC instrument type: Waters Alliance 2795; column: Merck Chromolith SpeedROD RP-18e 100 mm×4.6 mm; mobile phase A: water+500 µl of 50% strength formic acid/l, mobile phase B: acetonitrile+500 µl of 50% strength formic acid/l; gradient: 0.0 min 10% B→7.0 min 95% B→9.0 min 95% B; oven: 35° C.; flow rate: 0.0 min 1.0 ml/min→7.0 min 2.0 ml/min→9.0 min 2.0 ml/min; UV detection: 210 nm.

Method 3 (LC-MS):

Instrument: Micromass Quattro LCZ with HPLC Agilent Serie 1100; column: Phenomenex Gemini 3µ 30 mm×3.00 mm; mobile phase A: 1 l of water+0.5 ml of 50% strength formic acid, mobile phase B: 1 l of acetonitrile+0.5 ml of 50% strength formic acid; gradient: 0.0 min 90% A→2.5 min 30% A→3.0 min 5% A→4.5 min 5% A; flow rate: 0.0 min 1 ml/min→2.5 min/3.0 min/4.5 min 2 ml/min; oven: 50° C.; UV detection: 208-400 nm.

Method 4 (LC-MS):

MS instrument type: Micromass ZQ; HPLC instrument type: HP 1100 Series; UV DAD; column: Phenomenex Gemini 3µ 30 mm×3.00 mm; mobile phase A: 1 l of water+0.5 ml of 50% strength formic acid, mobile phase B: 1 l of acetonitrile+0.5 ml of 50% strength formic acid; gradient: 0.0 min 90% A→2.5 min 30% A→3.0 min 5% A→4.5 min 5% A; flow rate: 0.0 min ml/min→2.5 min/3.0 min/4.5 min 2 ml/min; oven: 50° C.; UV detection: 210 nm.

Method 5 (LC-MS):

Instrument: Micromass Quattro LCZ with HPLC Agilent Serie 1100; column: Phenomenex Onyx Monolithic C18, 100 mm×3 mm; mobile phase A: 1 l of water+0.5 ml of 50% strength formic acid, mobile phase B: 1 l of acetonitrile+0.5 ml of 50% strength formic acid; gradient: 0.0 min 90% A→2 min 65% A→4.5 min 5% A→6 min 5% A; flow rate: 2 ml/min; oven: 40° C.; UV detection: 208-400 nm.

Method 6 (Preparative HPLC):

HPLC instrument type: Abimed/Gilson Pump 305/306; Manometric Module 806; UV Knauer Variable Wavelength Monitor; column: Gromsil C18, 10 nm, 250 mm×30 mm; mobile phase A: 1 l of water+0.5 ml 99% TFA, mobile phase B: 1 l of acetonitrile; gradient: 0.0 min 2% B→10 min 2% B→50 min 90% B; flow rate: 20 ml/min; volume: 628 ml A and 372 ml B.

Method 7 (LC-MS):

MS instrument type: Waters ZQ; HPLC instrument type: Waters Alliance 2795; column: Merck Chromolith RP18e, 100 mm×3 mm; mobile phase A: 1 l of water+0.5 ml of 50% strength formic acid, mobile phase B: 1 l of acetonitrile+0.5 ml of 50% strength formic acid; gradient: 0.0 min 90% A→2 min 65% A→4.5 min 5% A→6 min 5% A; flow rate: 2 ml/min; oven: 40° C.; UV detection: 210 nm.

Method 8 (GC-MS):

Instrument: Micromass GCT, GC6890; column: Restek RTX-35, 15 m×200 µm×0.33 µm; constant helium flow: 0.88 ml/min; oven: 70° C.; inlet: 250° C.; gradient: 70° C., 30° C./min→310° C. (maintained for 3 min).

Method 9 (GC-MS):

Instrument: Micromass GCT, GC6890; column: Restek RTX-35MS, 30 m×250 µm×0.25 µm; constant helium flow: 0.88 ml/min; oven: 60° C.; inlet: 250° C.; gradient: 60° C. (maintained for 0.30 min), 50° C./min→120° C., 16° C./min→250° C., 30° C./min→300° C. (maintained for 1.7 min).

Method 10 (Chiral HPLC):

HPLC instrument type: HP 1100 with DAD detection; column: Daicel Chiralpak IA, 5 µm, 250 mm×4.6 mm; mobile phase: 50% isohexane, 5% methanol, 45% tert-butyl methyl ether; flow rate: 15 ml/min.

Method 11 (Chiral HPLC):

HPLC instrument type: HP 1100 with DAD detection; column: Daicel Chiralpak AD-H, 5 µm, 250 mm×20 mm; mobile phase: 50% isohexane, 50% 2-propanol; flow rate: 15 ml/min.

Method 12 (LC-MS):

MS instrument type: Micromass ZQ; HPLC instrument type: Waters Alliance 2795; column: Phenomenex Synergi 2µ Hydro-RP Mercury 20 mm×4 mm; mobile phase A: 1 l of water+0.5 ml of 50% strength formic acid, mobile phase B: 1 l of acetonitrile+0.5 ml of 50% strength formic acid; gradient: 0.0 min 90% A→2.5 min 30% A→3.0 min 5% A→4.5 min 5% A; flow rate: 0.0 min 1 ml/min→2.5 min/3.0 min/4.5 min 2 ml/min; oven: 50° C.; UV detection: 210 nm.

Method 13 (LC-MS):

Instrument: Micromass Quattro LCZ with HPLC Agilent Serie 1100; column: Phenomenex Synergi 2μ Hydro-RP Mercury 20 mm×4 mm; mobile phase A: 1 l of water+0.5 ml of 50% strength formic acid, mobile phase B: 1 l of acetonitrile+ 0.5 ml of 50% strength formic acid; gradient: 0.0 min 90% A→2.5 min 30% A→3.0 min 5% A→4.5 min 5% A; flow rate: 0.0 min 1 ml/min→2.5 min/3.0 min/4.5 min 2 ml/min; oven: 50° C.; UV detection: 208-400 nm.

Method 14 (LC-MS):

Instrument: Micromass Platform LCZ with HPLC Agilent Serie 1100; column: Thermo Hypersil GOLD 3μ 20 mm×4 mm; mobile phase A: 1 l of water+0.5 ml of 50% strength formic acid, mobile phase B: 1 l of acetonitrile+0.5 ml of 50% strength formic acid; gradient: 0.0 min 100% A→0.2 min 100% A→2.9 min 30% A→3.1 min 10% A→5.5 min 10% A; flow rate: 0.8 ml/min; oven: 50° C.; UV detection: 210 nm.

Method 15 (LC-MS):

MS instrument type: Micromass ZQ; HPLC instrument type: HP 1100 Series; UV DAD; column: Phenomenex Synergi 2μ Hydro-RP Mercury 20 mm×4 mm; mobile phase A: 1 l of water+0.5 ml of 50% strength formic acid, mobile phase B: 1 l of acetonitrile+0.5 ml of 50% strength formic acid; gradient: 0.0 min 90% A→2.5 min 30% A→3.0 min 5% A→4.5 min 5% A; flow rate: min 1 ml/min→2.5 min/3.0 min/4.5 min 2 ml/min; oven: 50° C.; UV detection: 210 nm.

Method 16 (Chiral HPLC):

HPLC instrument type: HP 1100 with DAD detection; column: Daicel Chiralpak IA-H, 5 μm, 250 mm×20 mm; mobile phase: 80% TBME, 20% methanol; flow rate: 15 ml/min.

Method 17 (Chiral HPLC):

HPLC instrument type: HP 1100 with DAD detection; column: Daicel Chiralpak IA, 5 μm, 250 mm×4.6 mm; mobile phase: 80% TBME, 20% methanol; flow rate: 1.0 ml/min.

Method 18 (Chiral HPLC):

HPLC instrument type: HP 1100 with DAD detection; column: Daicel Chiralpak IA-H, 5 μm, 250 mm×20 mm; mobile phase: 50% isohexane, 45% TBME, 5% methanol; flow rate: 15 ml/min.

Method 19 (Chiral HPLC):

HPLC instrument type: HP 1100 with DAD detection; column: Daicel Chiralpak IA, 5 μm, 250 mm×4.6 mm; mobile phase: 40% isohexane, 54% TBME, 6% methanol; flow rate: 1.0 ml/min.

Method 20 (HPLC):

HPLC instrument type: HP 1100 with DAD detection; column: Kromasil 100 C 18, 5 μm, 250 mm×20 mm; mobile phase: 25% 0.2% strength acetic acid, 75% acetonitrile; flow rate: 25 ml/min.

Method 21 (LC-MS):

Instrument: Micromass QuattroPremier with Waters UPLC Acquity; column: Thermo Hypersil GOLD 1.9μ 50 mm×1 mm; mobile phase A: 1 l of water+0.5 ml of 50% strength formic acid, mobile phase B: 1 l of acetonitrile+0.5 ml of 50% strength formic acid; gradient: 0.0 min 90% A→0.1 min 90% A→1.5 min 10% A→2.2 min 10% A; flow rate: 0.33 ml/min; oven: 50° C.; UV detection: 210 nm.

Method 22 (LC-MS):

Instrument: Micromass Quattro LCZ with HPLC Agilent Serie 1100; column: Phenomenex Synergi 2.5μ MAX-RP 100A Mercury 20 mm×4 mm; mobile phase A: 1 l of water+ 0.5 ml of 50% strength formic acid, mobile phase B: 1 l of acetonitrile+0.5 ml of 50% strength formic acid; gradient: 0.0 min 90% A→0.1 min 90% A→3.0 min 5% A→4.0 min 5% A→4.1 min 90% A; flow rate: 2 ml/min; oven: 50° C.; UV detection: 208-400 nm.

Starting Materials and Intermediates:

Example 1A 4-(2-Hydroxyethoxy)cyclohexanecarboxylic acid

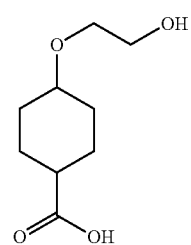

1.00 g (5.49 mmol) of 4-(2-hydroxyethoxy)benzoic acid is dissolved in 30 ml of dry THF and 30 ml of dry ethanol, and 1.13 mg (0.55 mmol) of rhodium on alumina are added. The reaction mixture is hydrogenated at +50° C. at a hydrogen pressure of 50 bar for 12 h. The mixture is then hydrogenated at +60° C. at a hydrogen pressure of 80 bar for a further 48 h. After filtration, the filtrate is concentrated on a rotary evaporator. The residue is directly used in the next reaction without further purification.

Yield: 1.00 g (84% of theory, 87% pure)

$^1$H-NMR (400 MHz, DMSO-$d_6$): δ=12.3 (br. s, 1H), 4.52 (br. s, 1H), 3.49-3.34 (m, 4H), 3.25-3.14 (m, 1H), 2.32-2.22 (m, 1H), 2.20-0.90 (m, 8H).

GC-MS (Method 8): $R_t$=1.43 min; MS (ESIpos): m/z=222 [M+H]$^+$.

Example 2A

Methyl 4-(2-hydroxyethoxy)cyclohexanecarboxylate

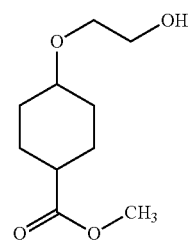

The crude product from Example 1A is dissolved in 40 ml of methanol, and 200 mg of Dowex 50 WX8-100 ion exchanger (washed beforehand 7× with in each case 20 ml of 2 M hydrochloric acid and then 7× with in each case 20 ml of methanol) are added. The mixture is stirred at +64° C. for 20 h. After cooling to RT, the ion exchanger is filtered off and the filtrate is concentrated on a rotary evaporator. The crude product is directly used in the next reaction without further purification.

Yield: 1.00 g (79% of theory, 76% pure)

GC-MS (Method 8): $R_t$=5.26 min; MS (ESIpos): m/z=183 [M+H]$^+$.

Example 3A

Methyl 4-(2-{[tert-butyl(diphenyl)silyl]oxy}ethoxy)cyclohexanecarboxylate

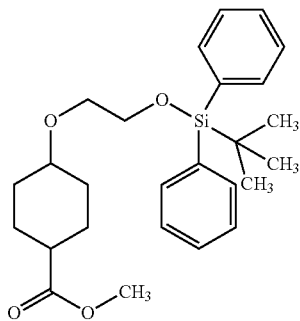

The crude product from Example 2A is dissolved in 20 ml of dichloromethane, and 0.83 ml (5.93 mmol) of triethylamine and 1.54 ml (5.93 mmol) of tert-butyldiphenylchlorosilane are added. After addition of 24.2 mg (0.20 mmol) of 4-N,N-dimethylaminopyridine the mixture is stirred at RT for 20 h. In each case 10 ml of ethyl acetate and of saturated aqueous sodium bicarbonate solution are then added. The phases are separated, and the combined organic phases are then dried over magnesium sulfate. The solvent is removed on a rotary evaporator and the residue is purified chromatographically on silica gel 60 (mobile phase: gradient cyclohexane/ethyl acetate 100:1→20:1).

Yield: 1.90 g (87% of theory, cis/trans mixture, 87% pure)

GC-MS (Method 8): $R_t$=10.36 min and 10.44 min; MS (ESIpos): m/z=458 [M+NH$_4$]$^+$.

Example 4A

[4-(2-{[tert-Butyl(diphenyl)silyl]oxy}ethoxy)cyclohexyl]methanol

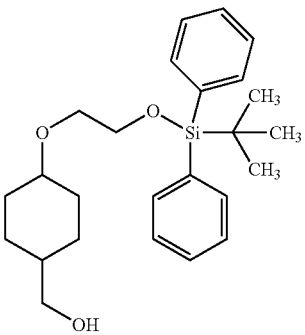

1.90 g (3.75 mmol, 87% pure) of the compound from Example 3A are dissolved in 15 ml of diethyl ether and added dropwise to a suspension of 170.9 mg (4.50 mmol) of lithium aluminum hydride in 15 ml of diethyl ether. The mixture is then stirred at RT for 20 h. A further 136.7 mg (3.60 mmol) of lithium aluminum hydride are then added, and the mixture is stirred at RT for another 20 h. The mixture is then triturated with 257 μl of water and 257 μl of 15% strength aqueous potassium hydroxide solution. A further 10 ml of water are added, and the phases are separated. The organic phase is dried over magnesium sulfate. The solvent is removed on a rotary evaporator and the residue is purified chromatographically on silica gel 60 (mobile phase: gradient cyclohexane/ethyl acetate 50:1→10:1).

Yield: 1.20 g (72% of theory, 93% pure, cis/trans mixture)

$^1$H-NMR (400 MHz, DMSO-d$_6$): δ=7.71-7.63 (m, 4H), 7.49-7.39 (m, 6H), 4.43-4.30 (m, 1H), 3.79-3.70 (m, 2H), 3.54-3.46 (m, 2H), 3.21-3.14 (m, 2H), 2.00-1.56 (m, 3H), 1.48-0.78 (m, 6H), 0.98 (s, 9H).

LC-MS (Method 12): $R_t$=3.10 min and 3.16 min; MS (ESIpos): m/z=435 [M+Na]$^+$.

Example 5A 4-(2-{[tert-Butyl(diphenyl)silyl]oxy}ethoxy)cyclohexanecarbaldehyde

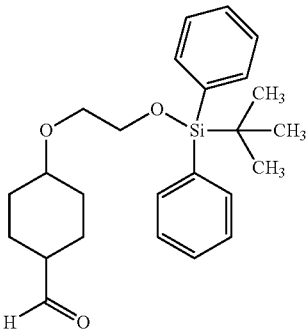

553.7 mg (4.36 mmol) of oxalyl chloride are dissolved in 25 ml of dichloromethane and cooled to −78° C. 681.6 mg (8.72 mmol) of dimethyl sulfoxide are added slowly. A solution of 1.20 g (2.91 mmol) of the compound from Example 4A in 10 ml of dichloromethane is then added dropwise. The mixture is stirred at −78° C. for 1 h. 2.0 ml (14.54 mmol) of triethylamine are then added, and the mixture is allowed to warm to RT over a period of 1 h. The mixture is then added to 20 ml of a 1:1 mixture of saturated aqueous sodium bicarbonate solution and ethyl acetate. After separation of the phases the aqueous phase is extracted two more times with in each case 10 ml of ethyl acetate. The combined organic phases are freed from the solvent on a rotary evaporator. The residue is purified chromatographically on silica gel 60 (mobile phase: gradient cyclohexane/ethyl acetate 20:1→5:1).

Yield: 1.00 g (84% of theory, cis/trans mixture)

$^1$H-NMR (400 MHz, DMSO-d$_6$): δ=9.57, 9.53 (2 s, 1H, cis/trans), 7.70-7.62 (m, 4H), 7.49-7.38 (m, 6H), 3.78-3.71 (m, 2H), 3.56-3.42 (m, 3H), 2.37-2.28 (m, 1H), 1.85-1.74 (m, 1H), 1.74-1.48 (m, 5H), 1.29-1.15 (m, 2H), 0.98 (s, 9H).

GC-MS (Method 8): $R_t$=9.95 min and 9.98 min; MS (ESIpos): m/z=428 [M+NH$_4$]$^+$.

Example 6A

2-Amino-4-[4-(2-{[tert-butyl(diphenyl)silyl]oxy}ethoxy)cyclohexyl]-6-mercaptopyridine-3,5-dicarbonitrile

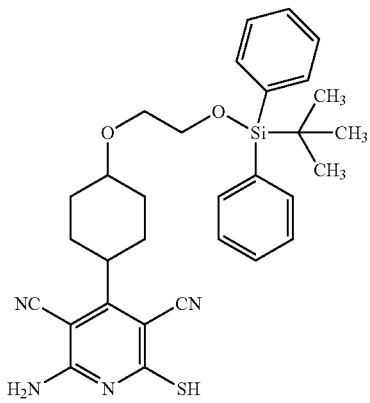

1.00 g (2.44 mmol) of the compound from Example 5A are dissolved in 10 ml of dry ethanol, and 512.1 mg (5.11 mmol) of cyanothioacetamide and 517.3 mg (5.11 mmol) of 4-methylmorpholine are added. The reaction mixture is stirred under reflux for 6 h and then at RT for 20 h. The solvent is then removed on a rotary evaporator. 290 mg of the crude product obtained are directly purified by preparative HPLC (column: YMC GEL ODS-AQ S-5/15 µm; mobile phase gradient: acetonitrile/water 10:90→95:5). This gives the cis/trans isomers in pure form. By repeated HPLC separations, it is also possible to purify the remainder of the crude product; however, for the next reaction it is used as isomer mixture.

trans Isomer:

Yield: 14 mg (1% of theory)

$^1$H-NMR (400 MHz, DMSO-d$_6$): δ=12.89 (br. s, 1H), 8.09-7.60 (br. s, 2H), 7.71-7.62 (m, 4H), 7.50-7.39 (m, 6H), 3.78-3.71 (m, 2H), 3.61-3.53 (m, 2H), 2.93-2.78 (m, 1H), 2.08-1.96 (m, 4H), 1.86-1.70 (m, 2H), 1.27-1.10 (m, 2H), 0.99 (s, 9H).

LC-MS (Method 5): $R_t$=4.55 min; MS (ESIpos): m/z=574 [M+NH$_4$]$^+$.

cis Isomer:

Yield: 33 mg (2% of theory)

$^1$H-NMR (400 MHz, DMSO-d$_6$): δ=12.87 (br. s, 1H), 7.82-7.56 (br. s, 2H), 7.70-7.62 (m, 4H), 7.48-7.39 (m, 6H), 3.84-3.78 (m, 2H), 3.64-3.60 (m, 1H), 3.54-3.48 (m, 2H), 2.93-2.83 (m, 1H), 2.38-2.23 (m, 2H), 2.02-1.89 (m, 2H), 1.52-1.36 (m, 4H), 0.98 (s, 9H).

LC-MS (Method 5): $R_t$=4.65 min; MS (ESIneg): m/z=555 [M−H]$^−$.

Example 7A

2-Amino-4-[4-(2-{[tert-butyl(diphenyl)silyl]oxy}ethoxy)cyclohexyl]-6-({[2-(4-chlorophenyl)-1,3-thiazol-4-yl]methyl}thio)pyridine-3,5-dicarbonitrile

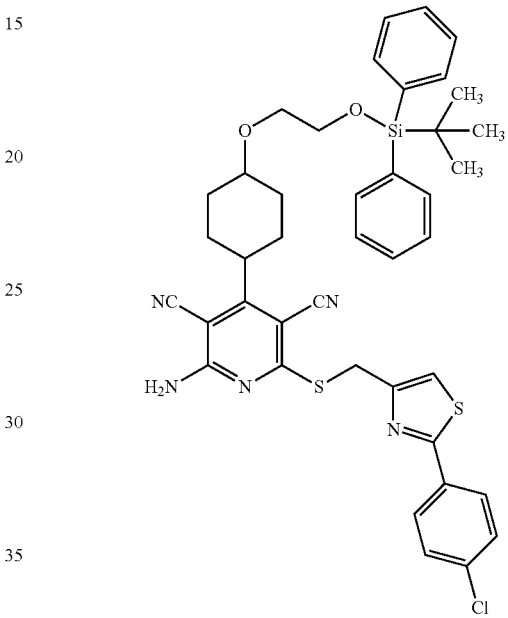

300 mg (0.32 mmol) of the compound from Example 6A (isomer mixture) are dissolved in 2.4 ml of dry DMF, 95 mg (0.39 mmol) of 4-(chloromethyl)-2-(4-chlorophenyl)-1,3-thiazole and 109 mg of sodium bicarbonate are added and the mixture is stirred at RT for 8 h. The mixture is then directly purified by preparative HPLC (column: YMC GEL ODS-AQ S-5/15 µm; mobile phase gradient: acetonitrile/water 10:90→95:5), the cis/trans isomers being separated in the process.

trans Isomer:

Yield: 35 mg (14% of theory)

$^1$H-NMR (400 MHz, DMSO-d$_6$): δ=8.21-7.82 (br. s, 2H), 7.95 (d, 2H), 7.89 (s, 7.70-7.62 (m, 4H), 7.56 (d, 2H), 7.50-7.40 (m, 6H), 4.58 (s, 2H), 3.73 (t, 2H), 3.56 (t, 2H), 2.89-2.78 (m, 1H), 2.13-2.05 (m, 2H), 2.05-1.92 (m, 2H), 1.80-1.70 (m, 2H), 1.23-1.11 (m, 2H), 0.99 (s, 9H).

LC-MS (Method 4): $R_t$=3.76 min; MS (ESIpos): m/z=764 [M+H]$^+$.

cis Isomer:

Yield: 43 mg (17% of theory)

$^1$H-NMR (400 MHz, DMSO-d$_6$): δ=8.16-7.22 (br. s, 2H), 7.96-7.90 (m, 2H), 7.88 (s, 1H), 7.69-7.60 (m, 4H), 7.55 (d, 2H), 7.49-7.38 (m, 6H), 4.57 (s, 2H), 3.80 (t, 2H), 3.61 (br. s, 1H), 3.50 (t, 2H), 2.94-2.82 (m, 1H), 2.37-2.20 (m, 2H), 2.01-1.91 (m, 2H), 1.48-1.38 (m, 4H), 0.99 (s, 9H).

LC-MS (Method 4): $R_t$=3.80 min; MS (ESIpos): m/z=764 [M+H]$^+$.

Example 8A

Methyl 4-hydroxycyclohexanecarboxylate

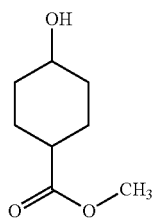

5.00 g (34.68 mmol) of 4-hydroxycyclohexanecarboxylic acid are dissolved in 80 ml of methanol, and 2 ml of conc. sulfuric acid are added slowly. The mixture is stirred under reflux for 20 h. After cooling to RT, the mixture is carefully poured into a mixture of 100 ml of ethyl acetate and 100 ml of saturated aqueous sodium bicarbonate solution. The phases are separated, and the organic phase is washed once with 20 ml of saturated aqueous ammonium chloride solution. The organic phase is dried over magnesium sulfate and the solvent is removed on a rotary evaporator. The crude product is directly used in the next reaction without further purification.

Yield: 4.5 g (74% of theory, 90% pure)

LC-MS (Method 13): $R_t$=1.17 min; MS (ESIpos): m/z=159 [M+H]$^+$.

Example 9A

Methyl 4-{[tert-butyl(dimethyl)silyl]oxy}cyclohexanecarboxylate

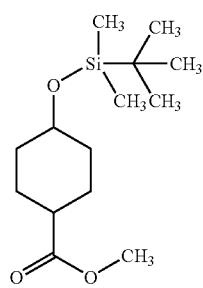

2.00 g (11.38 mmol) of the crude product from Example 8A (90% pure) are dissolved in 50 ml of dry DMF, and 1.47 g (21.62 mmol) of imidazole and 2.40 g (15.93 mmol) of tert-butyldimethyl-silyl chloride are added. The reaction mixture is stirred at RT for 20 h. 40 ml each of diethyl ether and of saturated aqueous sodium bicarbonate solution are then added to the mixture. After phase separation, the organic phase is dried over magnesium sulfate and the solvent is removed on a rotary evaporator. The crude product is used in the next reaction without further purification.

Yield: 3.9 g (100% of theory, 80% pure)

GC-MS (Method 9): $R_t$=7.30 min; MS (ESIpos): m/z=215 [M–C$_4$H$_9$]$^+$.

Example 10A (4-{[tert-Butyl(dimethyl)silyl]oxy}cyclohexyl)methanol

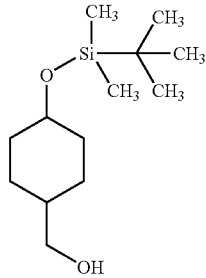

200 mg (0.59 mmol) of the crude product from Example 9A (80% pure) are dissolved in 1.5 ml of diethyl ether. At RT, this solution is added dropwise to a suspension of 13.4 mg (0.35 mmol) of lithium aluminum hydride in 1.5 ml of diethyl ether. The mixture is stirred at RT for 20 h. 12 μl of water, 12 μl of 15% strength aqueous potassium hydroxide solution and 3 ml of diethyl ether are then added, and the mixture is stirred at RT for 30 min. The reaction mixture is then filtered through a cartridge charged with 2.4 g of silica gel and 2.4 g of Extrelut (mobile phase: dichloromethane/ethanol 10:1). The solvent is removed on a rotary evaporator and the residue is purified chromatographically on silica gel 60 (mobile phase: gradient cyclohexane/ethyl acetate 20:1→10:1).

Yield: 88 mg (61% of theory)

$^1$H-NMR (400 MHz, DMSO-d$_6$): δ=4.31 (t, 1H), 3.95-3.89 (m, 1H), 3.17 (t, 2H), 1.58-1.49 (m, 2H), 1.43-1.20 (m, 7H), 0.83 (s, 9H), 0.01 (s, 6H).

GC-MS (Method 9): $R_t$=6.94 min; MS (ESIpos): m/z=245 [M+H]$^+$.

Example 11A

4-{[tert-Butyl(dimethyl)silyl]oxy}cyclohexanecarbaldehyde

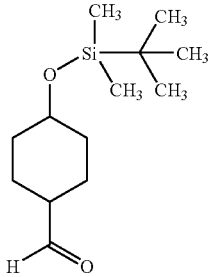

0.93 g (7.31 mmol) of oxalyl chloride is dissolved in 50 ml of dichloromethane and cooled to −78° C., and 1.14 g (14.63 mmol) of dimethyl sulfoxide are added slowly. A solution of 1.49 g (4.88 mmol) of the compound from Example 10A (incl. subsequent syntheses), dissolved in 10 ml of dichloromethane, is then added. The reaction mixture is stirred at −78° C. for 1 h. 3.4 ml (24.38 mmol) of triethylamine are then added slowly, and the mixture is warmed to RT over a period of 1 h. 50 ml of ethyl acetate and 30 ml of sodium bicarbonate solution are then added to the mixture. The phases are separated, and the aqueous phase is extracted twice with in each case 20 ml of ethyl acetate. The combined organic phases are dried over magnesium sulfate. The solvent is removed on a rotary evaporator and the residue is purified chromatographically on silica gel 60 (mobile phase: gradient cyclohexane/ethyl acetate 50:1→10:1).

Yield: 690 mg (56% of theory)

$^1$H-NMR (400 MHz, DMSO-d$_6$): δ=9.53 (s, 1H), 3.91-3.82 (m, 1H), 2.38-2.28 (m, 1H), 1.80-1.21 (m, 8H), 0.87 (s, 9H), 0.02 (s, 6H).

GC-MS (Method 9): R$_t$=6.59 min; MS (ESIpos): m/z=185 [M–C$_4$H$_9$]$^+$.

Example 12A

2-Amino-4-(4-{[tert-butyl(dimethyl)silyl]oxy}cyclohexyl)-6-mercaptopyridine-3,5-dicarbonitrile

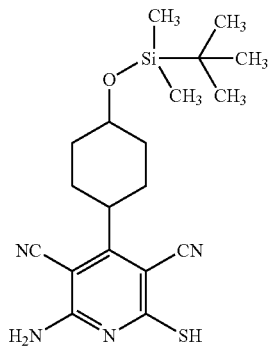

690 mg (2.85 mmol) of the compound from Example 1A and 598 mg (5.98 mmol) of cyanothioacetamide are dissolved in 20 ml of ethanol, and 604 mg (5.98 mmol) of N-methylmorpholine are added. The reaction mixture is stirred at +90° C. for 4 h. After cooling to RT the mixture is stirred at RT for a further 20 h. The precipitate formed is filtered off with suction and washed with 3 ml of ethanol which had been cooled to 0° C. The combined filtrate is concentrated on a rotary evaporator and the residue is purified by preparative HPLC (column: YMC GEL ODS-AQ S-5/15 μm; mobile phase gradient: acetonitrile/water 10:90→95:5), the cis/trans isomers being separated in the process.

cis Isomer:

Yield: 197 mg (17% of theory)

$^1$H-NMR (400 MHz, DMSO-d$_6$): δ=12.89 (s, 1H), 7.99-7.57 (br. s, 2H), 4.10-4.04 (m, 1H), 2.91-2.81 (m, 1H), 2.51-2.32 (m, 1H), 1.79-1.69 (m, 2H), 1.57-1.39 (m, 6H), 0.90 (s, 9H), 0.08 (s, 6H).

LC-MS (Method 4): R$_t$=3.10 min; MS (ESIpos): m/z=389 [M+H]$^+$.

trans Isomer:

Yield: 23 mg (2% of theory)

$^1$H-NMR (400 MHz, DMSO-d$_6$): δ=12.99-12.82 (br. s, 1H), 8.10-7.57 (br. s, 2H), 3.68-3.54 (m, 1H), 2.88-2.77 (m, 1H), 2.15-1.92 (m, 4H), 1.83-1.69 (m, 2H), 1.37-1.21 (m, 2H), 0.87 (s, 9H), 0.08 (s, 6H).

LC-MS (Method 13): R$_t$=2.88 min; MS (ESIpos): m/z=389 [M+H]$^+$.

Example 13A

2-Amino-4-(trans-4-{[tert-butyl(dimethyl)silyl]oxy}cyclohexyl)-6-({[2-(4-chlorophenyl)-1,3-thiazol-4-yl]methyl}thio)pyridine-3,5-dicarbonitrile

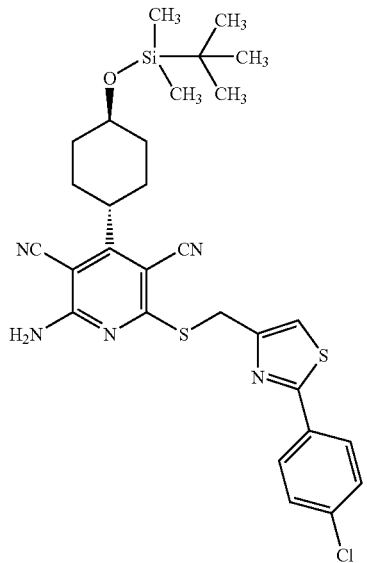

23 mg (0.06 mmol) of the compound from Example 12A (trans isomer), 17 mg (0.07 mmol) of 4-(chloromethyl)-2-(4-chlorophenyl)-1,3-thiazole and 20 mg (0.24 mmol) of sodium bicarbonate are initially charged in 2 ml of dry DMF and stirred at RT for 20 h. The mixture is then directly purified by preparative HPLC (column: YMC GEL ODS-AQ S-5/15 μm; mobile phase gradient: acetonitrile/water 10:90→95:5).

Yield: 25 mg (71% of theory)

LC-MS (Method 5): R$_t$=5.33 min; MS (ESIpos): m/z=596 [M+H]$^+$.

Example 14A

2-Amino-4-(cis-4-{[tert-butyl(dimethyl)silyl]oxy}cyclohexyl)-6-({[2-(4-chlorophenyl)-1,3-thiazol-4-yl]methyl}thio)pyridine-3,5-dicarbonitrile

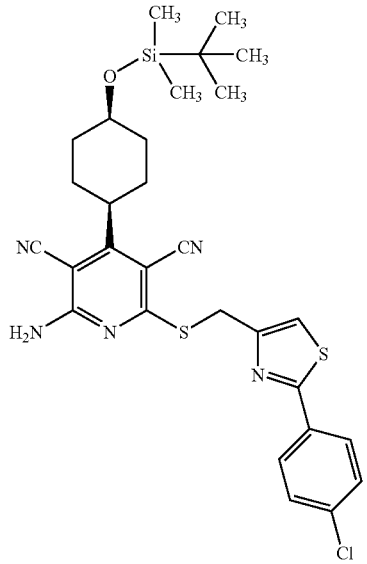

35 mg (0.08 mmol) of the compound from Example 12A (cis isomer), 23 mg (0.09 mmol) of 4-(chloromethyl)-2-(4- chlorophenyl)-1,3-thiazole and 26 mg (0.31 mmol) of sodium bicarbonate are initially charged in 2 ml of dry DMF and stirred at RT for 20 h. The mixture is then directly purified by preparative HPLC (column: YMC GEL ODS-AQ S-5/15 µm; mobile phase gradient: acetonitrile/water 10:90→95:5).

Yield: 24 mg (51% of theory)

LC-MS (Method 5): $R_t$=5.40 min; MS (ESIpos): m/z=596 [M+H]$^+$.

Example 15A

2-Amino-4-(cis-4-{[tert-butyl(dimethyl)silyl]oxy}cyclohexyl)-6-[(pyridin-3-ylmethyl)thio]-pyridine-3,5-dicarbonitrile

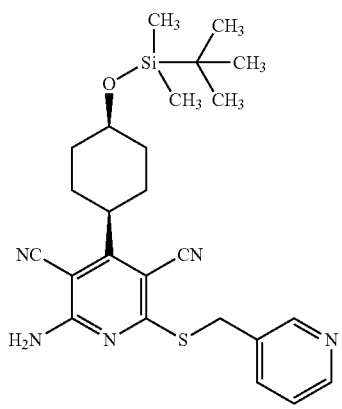

97 mg (0.23 mmol) of the compound from Example 12A (cis isomer), 46 mg (0.28 mmol) of 3-pyridinemethyl chloride hydrochloride and 78 mg (0.93 mmol) of sodium bicarbonate are initially charged in 2 ml of dry DMF and stirred at RT for 20 h. The mixture is then filtered and the filtrate is directly purified by preparative HPLC (column: YMC GEL ODS-AQ S-5/15 µm; mobile phase gradient: acetonitrile/water 10:90→95:5).

Yield: 80 mg (72% of theory)

$^1$H-NMR (500 MHz, DMSO-d$_6$): δ=8.70 (s, 1H), 8.38 (d, 1H), 8.20-7.72 (br. s, 2H), 7.87 (d, 1H), 7.30-7.25 (m, 1H), 4.39 (s, 2H), 4.00 (s, 1H), 2.85-2.77 (m, 1H), 2.36 (dq, 2H), 1.71-1.62 (m, 2H), 1.52-1.43 (m, 2H), 1.41-1.34 (m, 2H), 0.83 (s, 9H), 0.01 (s, 6H).

LC-MS (Method 12): $R_t$=3.03 min; MS (ESIpos): m/z=480 [M+H]$^+$.

Example 16A

2-Amino-4-(cis-4-{[tert-butyl(dimethyl)silyl]oxy}cyclohexyl)-6-[({2-[(4-fluorophenyl)amino]-1,3-thiazol-4-yl}methyl)thio]pyridine-3,5-dicarbonitrile

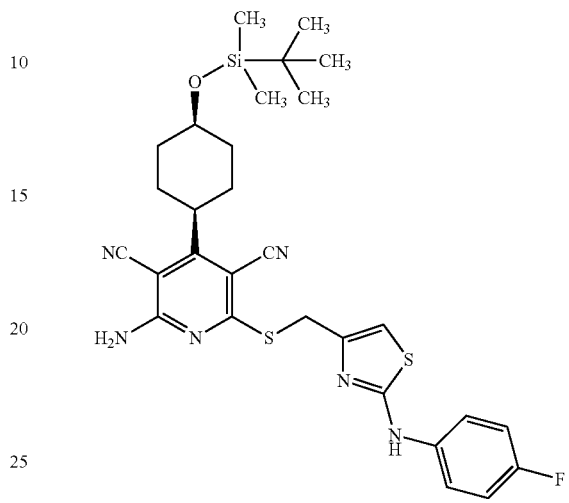

43 mg (0.26 mmol) of 4-fluorophenylthiourea and 31 mg (0.24 mmol) of 1,3-dichloroacetone are dissolved in 2 ml DMF and stirred at +80° C. for 3 h. After cooling to RT 93 mg (0.23 mmol) of the compound from Example 12A (cis isomer) and 78 mg (0.93 mmol) of sodium bicarbonate are added, and the reaction mixture is stirred at RT for 20 h. The mixture is then directly purified by preparative HPLC (column: YMC GEL ODS-AQ S-5/15 µm; mobile phase gradient: acetonitrile/water 10:90→95:5).

Yield: 66 mg (43% of theory)

$^1$H-NMR (500 MHz, DMSO-d$_6$): δ=10.22 (s, 1H), 8.05-7.87 (br. s, 2H), 7.63-7.56 (m, 2H), 7.12 (t, 2H), 6.92 (s, 1H), 4.40 (s, 2H), 4.05 (br. s, 1H), 2.91-2.82 (m, 1H), 2.48-1.68 (m, 2H), 1.58-1.47 (m, 2H), 1.47-1.39 (m, 2H), 0.89 (s, 9H), 0.06 (s, 6H).

LC-MS (Method 13): $R_t$=3.49 min; MS (ESIpos): m/z=595 [M+H]$^+$.

Example 17A tert-Butyl 4-(2-amino-3,5-dicyano-6-mercaptopyridin-4-yl)piperidine-1-carboxylate

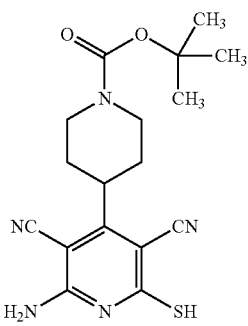

3.00 g (14.07 mmol) of tert-butyl 4-formylpiperidine-1-carboxylate and 2.82 g (28.13 mmol) of cyanothioacetamide are dissolved in 32 ml of ethanol, and 2.85 g (28.13 mmol) of 4-methylmorpholine are added. The mixture is stirred under reflux for 4 h then at RT for a further 8 h. The reaction mixture is then concentrated on a rotary evaporator and the residue is purified chromatographically on silica gel 60 (mobile phase: gradient dichloromethane/ethanol 50:1→5:1). The product obtained is used in the next reactions without further purification. Yield: 2.59 g (32% of theory, 63% pure)

LC-MS (Method 13): $R_t$=2.02 min; MS (ESIneg): m/z=358 [M–H]⁻.

Example 18A tert-Butyl 4-{2-amino-3,5-dicyano-6-[({2-[(4-fluorophenyl)amino]-1,3-thiazol-4-yl}methyl)thio]-pyridin-4-yl}piperdine-1-carboxylate

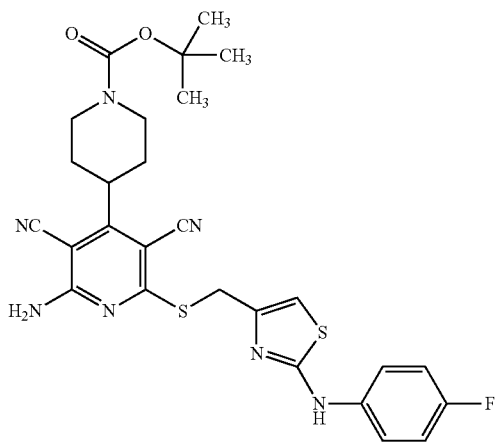

100 mg (0.20 mmol) of the compound from Example 17A (70% pure) and 130 mg (0.24 mmol) of 4-(chloromethyl)-N-(4-fluorophenyl)-1,3-thiazole-2-amine (from 4-fluorophenylthiourea and 1,3-dichloroacetone) are dissolved in 2.5 ml of dry DMF, and 100 mg (0.98 mmol) of sodium bicarbonate are added. The reaction mixture is stirred at RT for 8 h. After filtration the filtrate is concentrated under reduced pressure and the residue that remains is purified by preparative HPLC (column: YMC GEL ODS-AQ S-5/15 µm; mobile phase gradient: acetonitrile/water 10:90→95:5).

Yield: 40 mg (32% of theory, 88% pure)

LC-MS (Method 13): $R_t$=2.89 min; MS (ESIpos): m/z=566 [M+H]⁺.

Example 19A tert-Butyl 4-[2-amino-6-({[2-(4-chlorophenyl)-1,3-thiazol-4-yl]methyl}thio)-3,5-dicyanopyridin-4-yl]piperidine-1-carboxylate

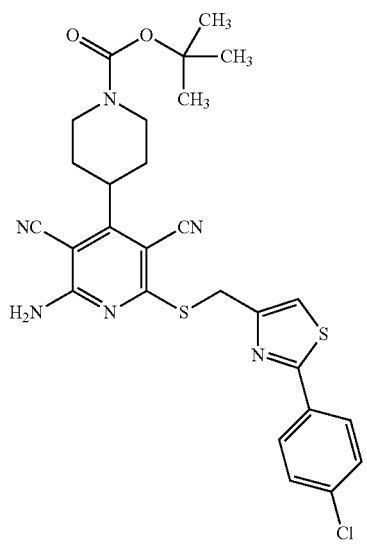

The title compound is obtained analogously to Example 18A from Example 17A and 4-(chloromethyl)-2-(4-chlorophenyl)-1,3-thiazole.

Yield: 41% of theory

LC-MS (Method 13): $R_t$=3.20 min; MS (ESIpos): m/z=567 [M+H]⁺.

Example 20A 4-({[tert-Butyl(diphenyl)silyl]oxy}methyl)piperidine

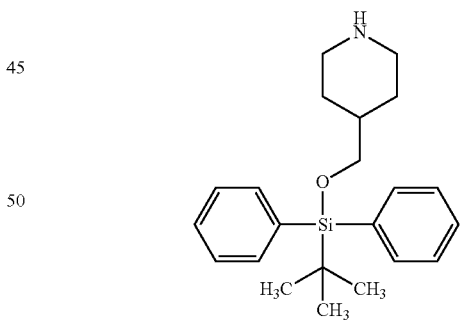

5.00 g (43.41 mmol) of 4-piperidinemethanol are dissolved in 400 ml of dichloromethane, and 9.1 ml (65.11 mmol) of triethylamine, 212 mg (1.74 mmol) of 4-N,N-dimethylaminopyridine and 16.9 ml (65.12 mmol) of tert-butyldiphenylchlorosilane are added in succession. The reaction mixture is stirred at RT for 8 h. After addition of 50 ml of dichloromethane the mixture is washed once with 20 ml of water and once with 20 ml of saturated aqueous sodium chloride solution. The organic phase is dried over magnesium sulfate. The crude product is used in the next reaction without further purification.

Yield: 21.16 g (96% of theory, 70% pure)

LC-MS (Method 4): $R_t$=1.91 min; MS (ESIpos): m/z=354 [M+H]$^+$.

Example 21A

2-[4-({[tert-Butyl(diphenyl)silyl]oxy}methyl)piperidin-1-yl]-2-oxoethyl acetate

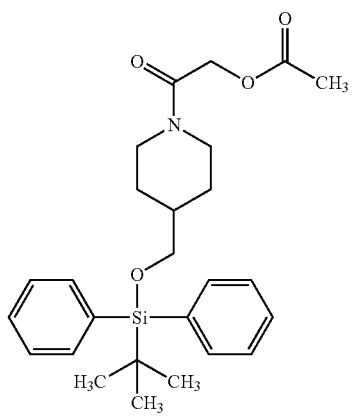

5 g of the crude product from Example 20A are suspended in 24 ml of dichloromethane and cooled to 0° C. 1.88 g (13.79 mmol) of acetoxyacetyl chloride and 5.9 ml (42.42 mmol) of triethylamine are added. The reaction mixture is stirred at RT for 8 h. After addition of 25 ml of dichloromethane the mixture is washed once with 10 ml of water and once with 10 ml of saturated aqueous sodium chloride solution. The organic phase is dried over magnesium sulfate. After removal of the solvent on a rotary evaporator the residue is purified chromatographically on silica gel 60 (mobile phase: gradient cyclohexane/ethyl acetate 20:1→1:1).

Yield: 4.04 g (84% of theory)

LC-MS (Method 4): $R_t$=3.21 min; MS (ESIpos): m/z=454 [M+H]$^+$.

Example 22A

2-[4-(Hydroxymethyl)piperidin-1-yl]-2-oxoethyl acetate

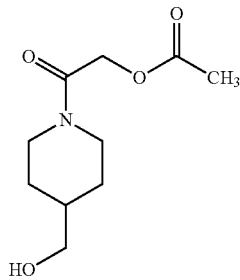

4.04 g (8.91 mmol) of the compound from Example 21A are dissolved in 69 ml of dry THF, and 9.8 ml (9.8 mmol) of a 1 M solution of tetrabutylammonium fluoride in THF are added. The reaction mixture is stirred at RT for 48 h. The solvent is then removed on a rotary evaporator and the residue is purified chromatographically on silica gel 60 (mobile phase: gradient dichloromethane/ethanol 200:1→1:1).

Yield: 800 mg (42% of theory)

GC-MS (Method 8): $R_t$=6.59 min; MS (ESIpos): m/z=216 [M+H]$^+$.

Example 23A 2-(4-Formylpiperidin-1-yl)-2-oxoethyl acetate

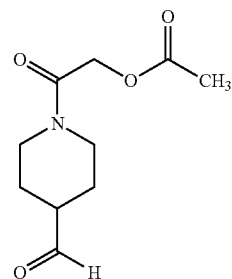

600 mg (2.79 mmol) of the compound from Example 22A are dissolved in 6 ml of dry dichloromethane, and 1.5 g of powdered molecular sieve (4 Å) and 490 mg (4.18 mmol) of N-methylmorpholine N-oxide are added. 49 mg (0.14 mmol) of tetrapropylammonium perruthenate are then added, and the mixture is stirred at RT for 1 h. The reaction mixture is then directly purified chromatographically on silica gel 60 (mobile phase: gradient dichloromethane/ethanol 100:1→20:1).

Yield: 194 mg (33% of theory)

GC-MS (Method 8): $R_t$=6.78 min; MS (ESIpos): m/z=214 [M+H]$^+$.

Example 24A

2-[4-(2-Amino-3,5-dicyano-6-mercaptopyridin-4-yl)piperidin-1-yl]-2-oxoethyl acetate

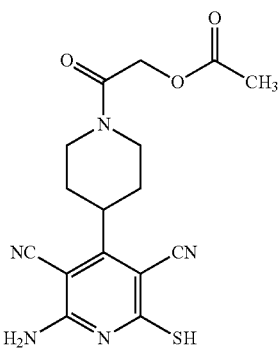

194 mg (0.91 mmol) of the compound from Example 23A and 182 mg (1.82 mmol) of cyanothioacetamide are initially charged in 2 ml of dry ethanol, and 184 mg (1.82 mmol) of 4-methylmorpholine are added. The reaction mixture is stirred at +78° C. for 4 h. After cooling to RT the mixture is stirred at this temperature for a further 8 h. After removal of the solvent on a rotary evaporator the residue is purified chromatographically on silica gel 60 (mobile phase: gradient dichloromethane/ethanol 20:1→1:1). The product obtained is used in the next reaction without further purification.

Yield: 102 mg (17% of theory, 55% pure)

Example 25A

2-{4-[2-Amino-6-({[2-(4-chlorophenyl)-1,3-thiazol-4-yl]methyl}thio)-3,5-dicyanopyridin-4-yl]-piperidin-1-yl}-2-oxoethyl acetate

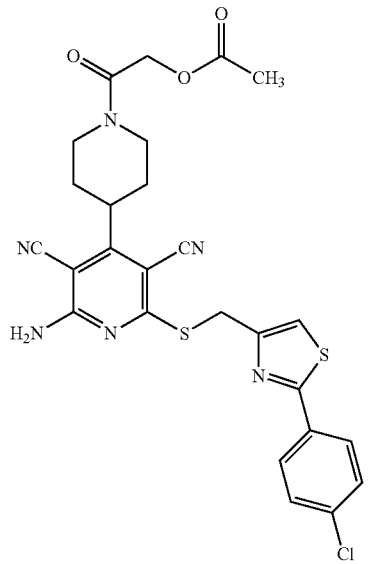

34 mg (0.06 mmol) of the compound from Example 24A are dissolved in 1.2 ml of dry DMF, and 17 mg (0.07 mmol) of 4-(chloromethyl)-2-(4-chlorophenyl)-1,3-thiazole and 19 mg (0.23 mmol) of sodium bicarbonate are added. The reaction mixture is stirred at RT for 8 h. The mixture is then filtered, and about 0.5 ml of water is added to the filtrate. The precipitate formed is filtered off with suction and dried under reduced pressure at +50° C.

Yield: 29 mg (74% of theory, 88% pure)

LC-MS (Method 3): $R_t$=2.58 min; MS (ESIpos): m/z=567 [M+H]$^+$.

Example 26A

3-[4-({[tert-Butyl(diphenyl)silyl]oxy}methyl)piperidin-1-yl]propyl acetate

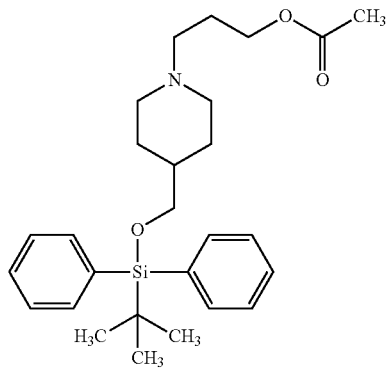

5.00 g (12.44 mmol) of the compound from Example 20A are dissolved in 57 ml of acetonitrile, and 4.51 g (24.89 mmol) of 3-bromopropyl acetate and 3.44 g (24.89 mmol) of potassium carbonate are added. The reaction mixture is stirred at +80° C. for 8 h. After filtration, the solvent is removed on a rotary evaporator. The residue is taken up in 50 ml of ethyl acetate and washed in each case once with 10 ml of water and 10 ml of saturated aqueous sodium bicarbonate solution. The organic phase is dried over magnesium sulfate and the solvent is removed on a rotary evaporator. The crude product is used in the next reaction without further purification.

Yield: 6.38 g (93% of theory, 82% pure)

LC-MS (Method 2): $R_t$=4.64 min; MS (ESIpos): m/z=454 [M+H]$^+$.

Example 27A

3-[4-(Hydroxymethyl)piperidin-1-yl]propyl acetate

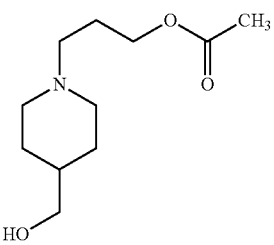

6.38 g (14.06 mmol) of the crude product from Example 26A are dissolved in 108 ml of dry THF, and 4.04 g (15.47 mmol) of tetra-n-butylammonium fluoride are added. The reaction mixture is stirred at RT for 48 h. After removal of the solvent the residue is directly purified chromatographically on silica gel 60 (mobile phase: gradient dichloromethane/ethanol 20:1→1:1).

Yield: 1.59 g (53% of theory)

$^1$H-NMR (400 MHz, DMSO-d$_6$): δ=4.39 (t, 1H), 4.00 (t, 2H), 3.22 (t, 2H), 2.89-2.78 (m, 4H), 2.37-2.24 (m, 2H), 2.00 (s, 3H), 1.90-1.78 (m, 2H), 1.76-1.67 (m, 2H), 1.66-1.53 (m, 2H), 1.39-1.23 (m, 1H), 1.17-1.02 (m, 2H).

MS (ESIpos): m/z=216 [M+H]$^+$.

Example 28A 3-(4-Formylpiperidin-1-yl)propyl acetate

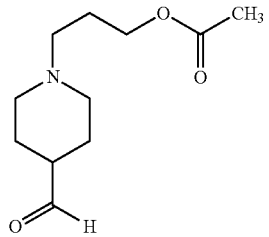

1.36 g (6.30 mmol) of the compound from Example 27A are dissolved in 14 ml dry dichloromethane, and 3.39 g of molecular sieve (4 Å), 1.11 g (9.44 mmol) of N-methylmorpholine N-oxide and 111 mg (0.32 mmol) of tetrapropylammonium perruthenate are added in succession. The reaction mixture is stirred at RT for 1 h and then directly purified chromatographically on silica gel 60 (mobile phase: gradient dichloromethane/ethanol 100:1→10:1).

Yield: 634 mg (48% of theory)

GC-MS (Method 8): $R_t$=5.53 min; MS (ESIpos): m/z=214 [M+H]$^+$.

Example 29A

3-[4-(2-Amino-3,5-dicyano-6-mercaptopyridin-4-yl)piperidin-1-yl]propyl acetate

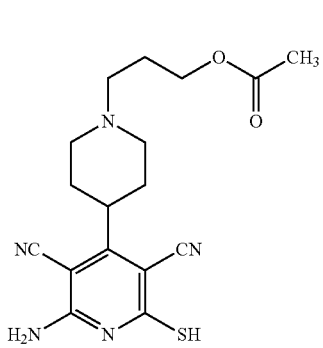

508 mg (2.38 mmol) of the compound from Example 28A and 477 mg (4.77 mmol) of cyanothioacetamide are initially charged in 5 ml of ethanol, and 482 mg (4.77 mmol) of 4-methylmorpholine are added. The reaction mixture is stirred at +78° C. for 4 h. After cooling to RT, the mixture is stirred at this temperature for a further 8 h. The solvent is removed on a rotary evaporator and the residue is adsorbed on diatomaceous earth and then purified chromatographically on silica gel 60 (mobile phase: gradient dichloromethane/ethanol 50:1→3:1).

Yield: 435 mg (48% of theory)

LC-MS (Method 14): $R_t$=2.09 min; MS (ESIpos): m/z=360 [M+H]$^+$.

Example 30A

Tetrahydro-2H-pyran-2-carbaldehyde

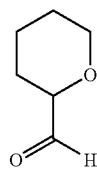

1000 mg (8.61 mmol) of 2-(hydroxymethyl)-tetrahydro-2H-pyran are dissolved in 27 ml of dry dichloromethane, and 1.5 g of powdered molecular sieve (4 Å) and 1.5 g (12.91 mmol) of N-methylmorpholine N-oxide are added. 151 mg (0.43 mmol) of tetrapropylammonium perruthenate are then added, and the reaction mixture is stirred at RT for 1 h. After removal of the solvent the mixture is prepurified chromatographically on silica gel 60 (mobile phase: gradient dichloromethane/ethanol 200:1→20:1). The product obtained is used in the next reaction without further purification.

Yield: 502 mg (51% of theory)

GC-MS (Method 8): $R_t$=2.07 min; MS (ESIpos): m/z=114 [M+H]$^+$.

Example 31A

2-Amino-6-mercapto-4-(tetrahydro-2H-pyran-2-yl)pyridine-3,5-dicarbonitrile

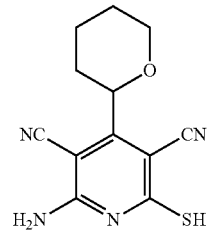

370 mg (2.66 mmol) of the crude product from Example 30A and 921 mg (9.20 mmol) of cyanothioacetamide are dissolved in 8.2 ml of ethanol, and 930 mg (9.20 mmol) of 4-methylmorpholine are added. The reaction mixture is stirred at +78° C. for 3 h. After cooling to RT, the mixture is stirred at this temperature for a further 8 h. After removal of the solvent the mixture is directly prepurified chromatographically on silica gel 60 (mobile phase: gradient dichloromethane/ethanol 200:1→20:1). The product obtained is used in the next reaction without further purification.

Yield: 387 mg (26% of theory, 76% pure)

LC-MS (Method 7): $R_t$=1.93 min; MS (ESIpos): m/z=261 [M+H]$^+$.

Example 32A

2-Amino-6-mercapto-4-(tetrahydro-2H-pyran-3-yl)pyridine-3,5-dicarbonitrile

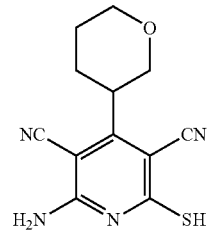

670 mg (5.87 mmol) of tetrahydro-2H-pyran-3-carbaldehyde [which can be prepared by the method of E. J. Corey et al., J. Am. Chem. Soc. 120, 13000-13001 (1998)] and 1.23 g (12.33 mmol) of cyanothioacetamide are dissolved in 11 ml of ethanol, and 1.23 g (12.33 mmol) of 4-methylmorpholine are added. The reaction mixture is stirred at +78° C. for 3 h. After cooling to RT the mixture is stirred at this temperature for a further 8 h. This results in the formation of a yellow precipitate. This precipitate is filtered off, adsorbed on diatomaceous earth and prepurified chromatographically on silica gel 60 (mobile phase: gradient dichloromethane/ethanol 200:1→1:1). The product obtained is used in the next reaction without further purification.

Yield: 564 mg (25% of theory, 69% pure)

LC-MS (Method 7): $R_t$=1.62 min; MS (ESIpos): m/z=261 [M+H]$^+$.

Example 33A

2-Amino-4-cyclohexyl-6-mercaptopyridine-3,5-dicarbonitrile

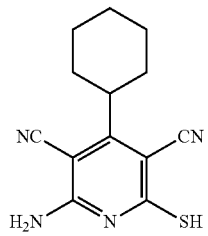

4.00 g (35.66 mmol) of cyclohexylcarbaldehyde and 7.14 g (71.32 mmol) of cyanothioacetamide are dissolved in 80 ml of ethanol, and 7.21 g (71.32 mmol) of 4-methylmorpholine are added. The reaction mixture is stirred at +78° C. for 3 h. After cooling to RT the mixture is stirred at this temperature for a further 8 h. The precipitate formed is filtered off with suction, the filtrate is then concentrated on a rotary evaporator and the residue that remains is purified chromatographically on silica gel 60 (mobile phase: gradient dichloromethane/ethanol 100:1→20:1).

Yield: 7.78 g (82% of theory)

$^1$H-NMR (400 MHz, DMSO-$d_6$): δ=7.37 (br. s, 2H), 2.92-2.79 (m, 1H), 2.09-1.92 (m, 2H), 1.90-1.77 (m, 2H), 1.75-1.54 (m, 3H), 1.37-1.08 (m, 3H).

LC-MS (Method 4): $R_t$=2.21 min; MS (ESIpos): m/z=259 [M+H]$^+$.

Example 34A

2-Amino-6-mercapto-4-(tetrahydro-2H-pyran-4-yl)pyridine-3,5-dicarbonitrile

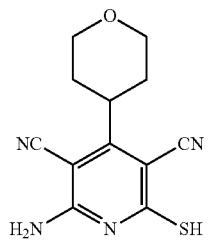

600 mg (5.26 mmol) of tetrahydropyran-4-carbaldehyde and 1.05 g (10.50 mmol) of cyanothioacetamide are dissolved in 10 ml of ethanol, and 1.06 g (10.50 mmol) of 4-methylmorpholine are added. The reaction mixture is stirred at +80° C. for 3 h. The precipitate formed is filtered off and used in the next reaction without further purification.

Yield: 720 mg (45% of theory, 87% pure)

$^1$H-NMR (400 MHz, DMSO-$d_6$): δ=12.94 (br. s, 1H), 7.82 (br. s, 2H), 3.99 (dd, 2H), 3.38 (dd, 2H), 3.13 (m, 1H), 2.29-2.19 (m, 2H), 1.60 (d, 2H).

LC-MS (Method 12): $R_t$=1.15 min; MS (ESIpos): m/z=261 [M+H]$^+$.

Example 35A

[6-(Pyridin-4-ylamino)pyridin-2-yl]methanol

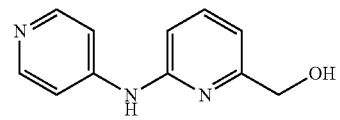

1.35 g (14.3 mmol) of 4-aminopyridine and 1.34 g (7.1 mmol) of (6-bromopyridin-2-yl)methanol are stirred at 150° C. for 4 h. After cooling to RT, 50 ml of acetonitrile are added and the reaction mixture is stirred for 20 min. The precipitate formed is filtered off with suction at 0° C. and washed with 10 ml of acetonitrile.

Yield: 1.25 g (39% of theory, 89% pure)

LC-MS (Method 14): $R_t$=1.76 min; MS (ESIpos): m/z=202 [M+H]$^+$.

Example 36A 6-(Chloromethyl)-N-pyridin-4-ylpyridine-2-amine

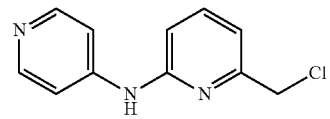

50 mg (0.22 mmol) of the compound from Example 35A and 53 mg (0.44 mmol) of thionyl chloride are initially charged at 0° C. in 1.5 ml of dichloromethane and, after warming to RT, stirred at this temperature for 12 h. The solvent is removed on a rotary evaporator and the product that remains is directly reacted further.

Yield: 65 mg (99% of theory, 74% pure)

LC-MS (Method 14): $R_t$=2.26 min; MS (ESIpos): m/z=220 [M+H]$^+$.

Example 37A

2-Chloro-6-({[2-(4-chlorophenyl)-1,3-thiazol-4-yl]methyl}thio)-4-cyclohexylpyridine-3,5-dicarbonitrite

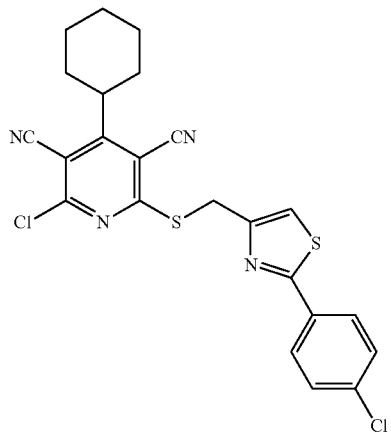

1.63 g (13.91 mmol) of isopentyl nitrite and 1.87 g (13.91 mmol) of copper(II) chloride are initially charged in 18 ml of acetonitrile, and 1.08 g (2.32 mmol) of the compound from Example 29 are added. The reaction mixture is stirred at +60° C. for 3 h. After cooling to RT 20 ml of 1 N hydrochloric acid are added to the reaction mixture. The aqueous phase is extracted twice with in each case 30 ml of ethyl acetate. The combined organic phases are washed once with 15 ml of saturated aqueous sodium bicarbonate solution and once with 15 ml of saturated aqueous sodium chloride solution. After drying over magnesium sulfate the solvent is removed on a rotary evaporator. The residue is purified chromatographically on silica gel 60 (mobile phase: gradient cyclohexane/ethyl acetate 100:1→5:1).

Yield: 626 mg (56% of theory)

$^1$H-NMR (400 MHz, DMSO-$d_6$): δ=7.94 (d, 2H), 7.72 (s, 1H), 7.58 (d, 2H), 4.72 (s, 2H), 3.08-2.96 (m, 1H), 2.04-1.78 (m, 6H), 1.77-1.57 (m, 2H), 1.42-1.11 (m, 2H).

LC-MS (Method 12): $R_t$=3.37 min; MS (ESIpos): m/z=485 [M+H]$^+$.

Example 38A

2-Amino-4-cyclohex-3-en-1-yl-6-mercaptopyridine-3,5-dicarbonitrile

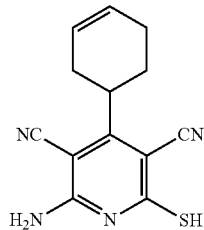

The title compound can be obtained analogously to Example 33A by reacting cyclohex-3-en-1-carbaldehyde with 2 equivalents of cyanothioacetamide in the presence of 4-methylmorpholine.

$^1$H-NMR (400 MHz, CDCl$_3$): δ=12.91 (s, 1H), 8.09-7.56 (br. s, 2H), 5.82-5.71 (m, 2H), 3.14-3.02 (m, 1H), 2.61-2.52 (m, 1H), 2.29-2.03 (m, 4H), 1.78 (d, 1H).

LC-MS (Method 5): $R_t$=2.82 min; MS (ESIpos): m/z=257 [M+H]$^+$.

Example 39A

2-Amino-6-methyl-4-(tetrahydro-2H-pyran-2-yl)pyridine-3,5-dicarbonitrile

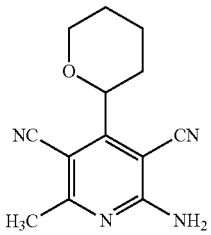

870 mg (7.62 mmol) of tetrahydro-2H-pyran-2-carbaldehyde, 504 mg (7.62 mmol) of malononitrile and 626 mg (7.62 mmol) of 3-aminocrotononitrile are dissolved in 8.4 ml of dry ethanol. The solution is cooled to 0° C., and 412 mg (7.62 mmol) of sodium methoxide are added a little at a time. The reaction mixture is then warmed to RT and stirred for 10 min. The mixture is then heated at reflux for 10 h. After cooling, the brown precipitate formed is filtered off with suction, washed three times with a total of 100 ml of ethanol and then dried at 50° C. under reduced pressure. The product is used without further purification for the next reaction. Purification may be carried out by preparative HPLC (column: YMC GEL ODS-AQ S-5, 15 μm; mobile phase gradient: acetonitrile/water 10:90→95:5).

Yield: 610 mg (20% of theory, 61% pure)

LC-MS (Method 7): $R_t$=2.45 min; MS (ESIpos): m/z=243 [M+H]$^+$.

Example 40A

2-Chloro-6-methyl-4-(tetrahydro-2H-pyran-2-yl)pyridine-3,5-dicarbonitrile

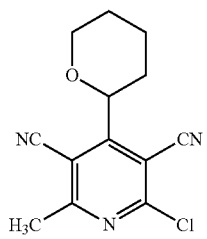

610 mg (2.52 mmol) of the compound from Example 39A are initially charged in 44 ml of acetonitrile, and 590 mg (5.04 mmol) of isopentyl nitrite and 677 mg (5.04 mmol) of copper (II) chloride are added. The reaction mixture is stirred at 60° C. for 30 min. 40 ml of 1 N hydrochloric acid are then added to the mixture and the mixture is extracted three times with in each case 100 ml of ethyl acetate. The combined organic phases are dried over magnesium sulfate and the solvent is removed on a rotary evaporator. The product is used in the next reaction without further purification.

Yield: 471 mg (53% of theory, 75% pure)

LC-MS (Method 4): $R_t$=2.50 min; MS (ESIpos): m/z=262 [M+H]$^+$.

Example 41A

2-Methyl-6-sulfanyl-4-(tetrahydro-2H-pyran-2-yl)pyridine-3,5-dicarbonitrile

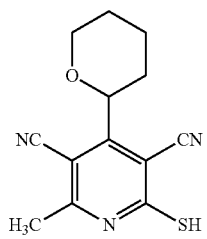

471 mg (1.35 mmol) of the compound from Example 40A are initially charged in 4 ml of dry DMF, and 126 mg (1.62 mmol) of sodium sulfide are added. The reaction mixture is stirred at RT for 12 h. The solvent is then removed on a rotary evaporator and the residue is purified chromatographically on silica gel 60 (mobile phase: gradient dichloromethane/ethanol 200:1→5:1).

Yield: 232 mg (64% of theory)

LC-MS (Method 4): $R_t$=2.01 min; MS (ESIpos): m/z=260 [M+H]$^+$.

Example 42A 4-(Chloromethyl)-2-(4-chlorophenyl)-1,3-oxazole

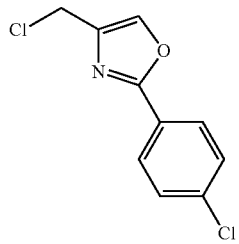

408 mg (3.21 mmol) of 1,3-dichloroacetone and 500 mg (3.21 mmol) of 4-chlorobenzamide are combined and stirred at 135° C. for 1 h. The mixture is then cooled to RT, 1.1 ml of conc. sulfuric acid are added carefully and the mixture is stirred for 5 min. The mixture is carefully poured onto ice. The precipitate is filtered off with suction and washed with water. After drying the crude product is used in the next reaction without further purification.

Yield: 426 mg (49% of theory, 85% pure)

LC-MS (Method 14): $R_t$=3.78 min; MS (ESIpos): m/z=228 [M+H]$^+$.

Example 43A rac-2-Chloro-6-({[2-(4-chlorophenyl)-1,3-oxazol-4-yl]methyl}sulfanyl)-4-(tetrahydro-2H-pyran-3-yl)pyridine-3,5-dicarbonitrile

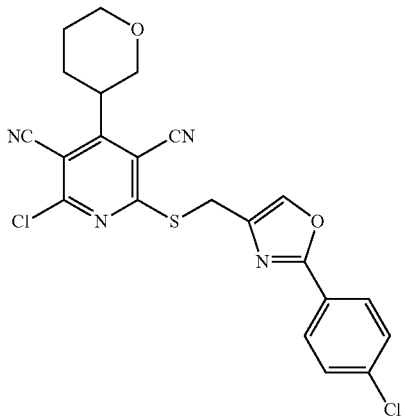

244 mg (2.08 mmol) of isopentyl nitrite and 280 mg (2.08 mmol) of copper(II) chloride are initially charged in 26 ml of acetonitrile, and 470 mg (1.04 mmol) of the compound from Example 58 are added at RT. The mixture is stirred at 60° C. for 3 h. After cooling to RT, 20 ml of 1 N hydrochloric acid are added to the reaction solution. The mixture is extracted twice with in each case 20 ml of ethyl acetate. The organic phases are dried over magnesium sulfate. After removal of the solvent on a rotary evaporator the residue is suspended in 20 ml of ethanol and the precipitate is filtered off with suction. The solid obtained is dried under reduced pressure. The crude product is used in the next reaction without further purification. Purification by preparative HPLC is possible (column: YMC GEL ODS-AQ S-5, 15 μm; mobile phase gradient: acetonitrile/water 10:90→95:5).

Yield: 239 mg (40% of theory, 82% pure)

LC-MS (Method 2): $R_t$=6.45 min; MS (ESIpos): m/z=471 [M+H]$^+$.

Example 44A 4-(Chloromethyl)-2-(4-fluoro-3-methylphenyl)-1,3-oxazole

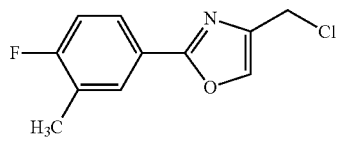

2.00 g (12.80 mmol) of 4-fluoro-3-methylbenzamide and 1.79 g (14.08 mmol) of 1,3-dichloroacetone are stirred at 130° C. for 2 days, resulting in the formation of a melt. The mixture is then cooled to RT, 3.0 ml of conc. sulfuric acid are added carefully at this temperature and the mixture is stirred for 15 min. The suspension obtained is poured into 20 ml of ice-water and stirred at RT overnight. The precipitate formed is filtered off and dried in a vacuum drying cabinet at 40° C. overnight.

Yield: 2.05 g (64% of theory, 90% pure)

LC-MS (Method 7): $R_t$=2.05 min; MS (ESIpos): m/z=226 [M+H]$^+$.

The other 4-(chloromethyl)-2-aryl-1,3-oxazoles used for the synthesis of working examples are prepared from the appropriate commercially available starting materials in an analogous manner.

Example 45A 2-(4-Chlorophenyl)-4,5-dimethyl-1,3-oxazole 3-oxide

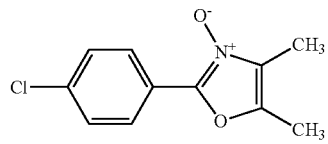

1.00 g (9.89 mmol) of diacetylmonoxime and 1.53 g (10.88 mmol) of 4-chlorobenzaldehyde are initially charged in 2 ml (34.94 mmol) of glacial acetic acid. With ice-cooling of the reaction mixture, hydrogen chloride gas is then introduced for 30 min. 10 ml of diethyl ether are then added to the reaction mixture. A precipitate is formed, which is filtered off with suction and washed twice with in each case 2 ml of diethyl ether. The precipitate is resuspended in about 5 ml of water and the suspension is made basic using ammonia. The mixture is then extracted four times with in each case 10 ml of dichloromethane. The combined organic phases are dried over magnesium sulfate and the solvent is removed on a rotary evaporator. The residue is used in the next reaction without further purification.

Yield: 1.85 g (84% of theory)

Example 46A 4-(Chloromethyl)-2-(4-chlorophenyl)-5-methyl-1,3-oxazole

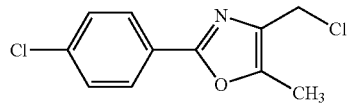

1.00 g (4.47 mmol) of the compound from Example 45A are initially charged in 15 ml of chloroform, and 1.5 ml (16.10 mmol) of phosphoryl chloride are added carefully. With stirring, the reaction mixture is heated at reflux for 30 min. The mixture is then cooled to 0° C. and made slightly basic by addition of ammonia. The mixture is extracted three times with in each case 20 ml of ethyl acetate. The combined organic phases are washed twice with in each case 5 ml of water and then dried over magnesium sulfate. The solvent is removed on a rotary evaporator. The residue is used in the next steps without further purification.

Yield: 1.33 g (96% of theory, 78% pure)

$^1$H-NMR (400 MHz, DMSO-$d_6$): δ=7.95 (d, 2H), 7.60 (d, 2H), 4.77 (s, 2H), 2.44 (s, 3H).

LC-MS (Method 3): $R_t$=2.80 min; MS (ESIpos): m/z=242 [M+H]$^+$.

Example 47A

Methyl 3-cyanobenzoate

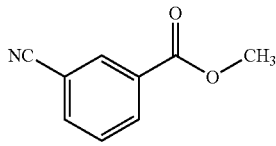

100 mg (0.68 mmol) of 3-cyanobenzoic acid are initially charged in 4 ml of toluene and 3.5 ml of methanol, and 0.51 ml (1.02 mnmol) of a 2 M solution of trimethylsilyldiazomethane in n-hexane is added at RT. The reaction mixture is stirred at RT for 1.5 h. After removal of the solvent on a rotary evaporator the residue is dried under reduced pressure. The product is obtained in pure form and is directly reacted further.

Yield: 116 mg (100% of theory)

LC-MS (Method 4): $R_t$=1.93 min; MS (ESIpos): m/z=162 [M+H]$^+$.

Example 48A

Methyl 3-(1H-tetrazol-5-yl)benzoate

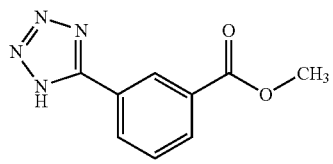

1.00 g (6.21 mmol) of the compound from Example 47A are initially charged in 18 ml of dry DMF. 2.42 g (37.23 mmol) of sodium azide and 1.99 g (37.23 mmol) of ammonium chloride are then added. The reaction mixture is stirred at 120° C. for 2.5 h. After cooling to RT the mixture is poured into a mixture of 30 ml of ice-water and 10 ml of ethyl acetate. 2.57 g (37.23 mmol) of sodium nitrite are added to this mixture to destroy excess azide. By addition of 6 N hydrochloric acid, the pH is then adjusted to 1-2 and the mixture is stirred at RT for 30 min. The mixture is extracted three times with in each case 20 ml of a 1:1 mixture of ethyl acetate and THF. The precipitate formed is filtered off with suction and dried under reduced pressure. In order to isolate more product, the separated organic phase is washed in each case once with in each case 10 ml of water and saturated aqueous sodium chloride solution. After drying over magnesium sulfate the solvent is removed on a rotary evaporator. Both solids are combined and used for the next step.

Yield: 1.18 g (91% of theory)

LC-MS (Method 5): $R_t$=1.87 min; MS (ESIpos): m/z=205 [M+H]$^+$.

Example 49A

[3-(1H-Tetrazol-5-yl)phenyl]methanol

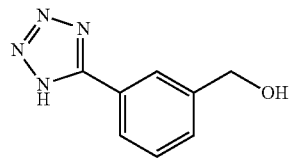

438 mg (11.56 mmol) of lithium aluminum hydride are initially charged in 60 ml of dry THF and cooled to 0° C., and a solution of 1.18 g (5.78 mmol) of the compound from Example 48A in 40 ml of dry THF is added. The reaction mixture is allowed to warm to RT and stirred at this temperature for 2 h. At 0° C., 4 M hydrochloric acid is added carefully to the reaction mixture until the evolution of hydrogen has stopped. The solution is then extracted three times with in each case 10 ml of ethyl acetate. The combined organic phases are washed in each case once with in each case 10 ml of water and saturated aqueous sodium chloride solution and dried over magnesium sulfate. After removal of the solvent on a rotary evaporator the residue is dried under reduced pressure. The product is used in the next reaction without further purification.

Yield: 0.80 g (77% of theory)

LC-MS (Method 5): $R_t$=0.90 min; MS (ESIpos): m/z=177 [M+H]$^+$.

Example 50A 3-(1H-Tetrazol-5-yl)benzyl methanesulfonate

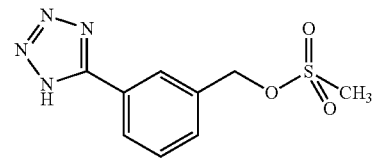

50 mg (0.28 mmol) of the compound from Example 49A are dissolved in 5 ml of dry dichloromethane, and 33 μl (0.43 mmol) of methanesulfonyl chloride and 0.06 ml (0.43 mmol) of triethylamine are added. The reaction mixture is stirred at RT for 10 h. The reaction mixture is then diluted with 10 ml of dichloromethane and washed in each case once with in each case 5 ml of water, 1 N hydrochloric acid and saturated aqueous sodium chloride solution. The organic phase is dried over magnesium sulfate. Removal of the solvent on a rotary evaporator gives a solid which is used in the next reaction without further purification.

Yield: 65 mg (40% of theory, 44% pure)

LC-MS (Method 4): $R_t$=1.58 min; MS (ESIpos): m/z=255 [M+H]$^+$.

Example 51A

Methyl cis-4-hydroxycyclohexanecarboxylate

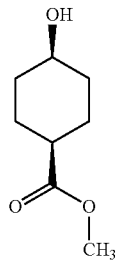

2.95 liters of methanol and 9.7 ml of conc. sulfuric acid are initially charged, and 175.0 g (1.21 mol) of cis-4-hydroxycyclohexanecarboxylic acid are added a little at a time at RT. The mixture is stirred at RT for 16 h. Almost all of the solvent is then removed on a rotary evaporator and the residue is taken up in 2 liters of a 1:1 mixture of saturated aqueous sodium bicarbonate solution and ethyl acetate. The phases are separated, and the organic phase is washed with 1 liter of 10% strength aqueous ammonium chloride solution and then dried over magnesium sulfate. After removal of the solvent on a rotary evaporator the residue is purified chromatographically on silica gel 60 (mobile phase: gradient ethyl acetate/petroleum ether 3:7→1:1).

Yield: 128.4 g (60% of theory, 89% pure)

$^1$H-NMR (400 MHz, CDCl$_3$): δ=3.89 (s, 1H), 3.68 (s, 3H), 2.44-2.35 (m, 1H), 2.07-1.90 (m, 2H), 1.90-1.58 (m, 8H).

GC-MS (Method 8): $R_t$=4.10 min; MS (ESIpos): m/z=140 [M−H$_2$O]$^+$.

Example 52A

Methyl cis-4-{[tert-butyl(dimethyl)silyl]oxy}cyclohexanecarboxylate

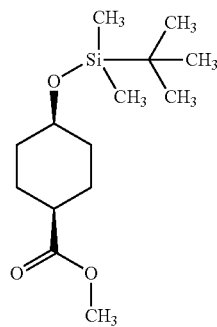

99.0 g (0.63 mol) of the compound from Example 51A are dissolved in 2 liters of dry DMF, and 132.0 g (0.88 mol) of tert-butyldimethylsilyl chloride and 80.9 g (1.19 mol) of imidazole are added at RT. The mixture is stirred at RT for 16 h. The solvent is then removed almost to dryness on a rotary evaporator and the residue is taken up in 2 liters of a 1:1 mixture of tert-butyl methyl ether and saturated aqueous sodium bicarbonate solution. The phases are separated, the organic phase is dried over magnesium sulfate and the solvent is removed on a rotary evaporator. The product is used in the next reaction without further purification.

Yield: 160.3 g (94% of theory)

$^1$H-NMR (400 MHz, CDCl$_3$): δ=3.89 (s, 1H), 3.65 (s, 3H), 2.35-2.25 (m, 1H), 1.99-1.88 (m, 2H), 1.70-1.55 (m, 4H), 1.55-1.41 (m, 2H), 0.88 (s, 9H), 0.04 (s, 6H).

GC-MS (Method 8): $R_t$=4.96 min; MS (ESIpos): m/z=273 [M+H]$^+$.

Example 53A (cis-4-{[tert-Butyl(dimethyl)silyl]oxy}cyclohexyl)methanol

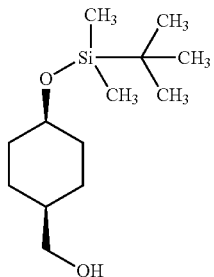

2.8 g (73.96 mmol) of lithium aluminum hydride are initially charged in 250 ml of tert-butyl methyl ether, and a solution of 22.9 g (84.05 mmol) of the compound from Example 52A in 250 ml of tert-butyl methyl ether is added dropwise at RT. The mixture is stirred at 40° C. for 16 h. A further 0.7 g (18.44 mmol) of lithium aluminum hydride is then added and the reaction mixture is heated at reflux for 10 h. After cooling to RT 20 ml of water are added carefully. 20 ml of a 15% strength solution of potassium hydroxide in water are then added. The phases are separated, the organic phase is dried over sodium sulfate and the solvent is removed on a rotary evaporator. The product obtained is used in the next reaction without further purification.

Yield: 21.1 g (100% of theory)

$^1$H-NMR (400 MHz, CDCl$_3$): δ=3.96-3.91 (br. s, 1H), 3.48-3.40 (br. s, 2H), 1.68-1.58 (m, 2H), 1.53-1.35 (m, 8H), 0.87 (s, 9H), 0.01 (s, 6H).

GC-MS (Method 8): $R_t$=4.77 min; MS (ESIpos): m/z=245 [M+H]$^+$.

Example 54A cis-4-{[tert-Butyl(dimethyl)silyl]oxy}cyclohexanecarbaldehyde

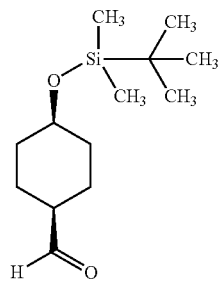

16.4 g (129.47 mmol) oxalyl chloride are dissolved in 600 ml of dichloromethane and cooled to −78° C. 20.2 g (258.95 mmol) of dimethyl sulfoxide are then slowly added dropwise. The mixture is stirred for 5 min. After addition of a solution of 21.1 g (86.32 mmol) of the compound from Example 53A in 200 ml of dichloromethane the mixture is stirred at −78° C. for 1 h. 60 ml (431.58 mmol) of triethylamine are then slowly added dropwise. Over a period of one hour, the reaction mixture is then warmed to RT, and 500 ml of saturated aqueous sodium bicarbonate solution are then added. The phases are separated, the organic phase is dried over sodium sulfate and the solvent is removed on a rotary evaporator. The residue is purified chromatographically on silica gel 60 (mobile phase: gradient petroleum ether→petroleum ether/ethyl acetate 9:1).

Yield: 15.6 g (75% of theory)

$^1$H-NMR (400 MHz, CDCl$_3$): δ=3.90-3.82 (br. s, 1H), 2.22-2.12 (m, 1H), 1.91-1.77 (m, 2H), 1.67-1.47 (m, 6H), 0.85 (s, 9H), 0.01 (s, 6H).

Example 55A

2-Amino-4-(cis-4-hydroxycyclohexyl)-6-sulfanylpyridine-3,5-dicarbonitrile

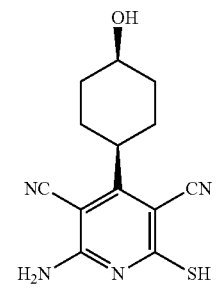

15.6 g (64.35 mmol) of the compound from Example 54A and 13.53 g (135.13 mmol) cyanothioacetamide are initially charged in 450 ml of ethanol, and 9.86 g (135.13 mmol) of 4-methylmorpholine are added. The mixture is heated at reflux for 4 h and then stirred at RT for 16 h. A precipitate is formed, which is filtered off with suction (and which corresponds to the tert-butyldimethylsilyl-protected target compound). The filtrate is freed from the solvent on a rotary evaporator and the residue is purified by preparative HPLC (Method 20).

Yield: 2.55 g (14% of theory)

$^1$H-NMR (400 MHz, DMSO-d$_6$): δ=12.95-12.83 (br. s, 1H), 8.06-7.52 (br. s, 2H), 4.88-4.46 (br. s, 1H), 3.46-3.22 (m, 1H), 2.84-2.73 (m, 1H), 2.13-1.92 (m, 4H), 1.77-1.67 (m, 3H), 1.28-1.12 (m, 3H).

LC-MS (Method 21): $R_t$=0.53 min; MS (ESIpos): m/z=275 [M+H]$^+$.

WORKING EXAMPLES

Example 1

2-Amino-6-({[2-(4-chlorophenyl)-1,3-thiazol-4-yl]methyl}thio)-4-[trans-4-(2-hydroxyethoxy)-cyclohexyl]pyridine-3,5-dicarbonitrile

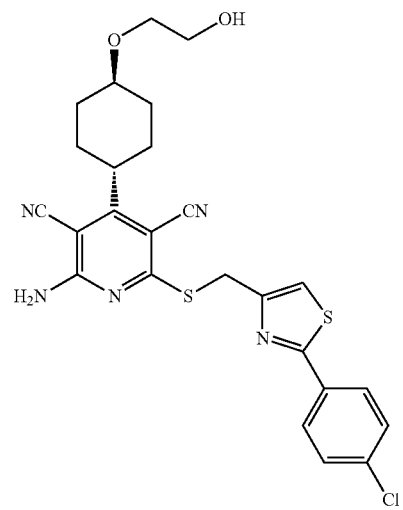

35 mg (0.05 mmol) of the compound from Example 7A (trans isomer) are dissolved in 5 ml of dry THF, 18 mg (0.07 mmol) of tetra-n-butylammonium fluoride are added and the mixture is stirred at RT for 20 h. 15 ml of ethyl acetate are then added to the mixture. The mixture is washed twice with in each case 3 ml of saturated aqueous sodium bicarbonate solution. The organic phase is dried over magnesium sulfate. After removal of the solvent on a rotary evaporator the crude product is purified by preparative HPLC (column: YMC GEL ODS-AQ S-5/15 µm; mobile phase gradient: acetonitrile/water 10:90→95:5).

Yield: 19 mg (79% of theory)

$^1$H-NMR (400 MHz, DMSO-d$_6$): δ=8.32-7.77 (br. s, 2H), 7.92 (d, 2H), 7.88 (s, 1H), 7.56 (d, 2H), 4.61-4.51 (m, 1H), 4.58 (s, 2H), 3.51-3.42 (m, 4H), 3.30-3.20 (m, 1H), 2.89-2.78 (m, 1H), 2.19-2.09 (m, 2H), 2.08-1.93 (m, 2H), 1.81-1.71 (m, 2H), 1.26-1.12 (m, 2H)

LC-MS (Method 5): R$_t$=3.86 min; MS (ESIpos): m/z=526 [M+H]$^+$..

Example 2

2-Amino-6-({[2-(4-chlorophenyl)-1,3-thiazol-4-yl]methyl}thio)-4-[cis-4-(2-hydroxyethoxy)cyclohexyl]pyridine-3,5-dicarbonitrile

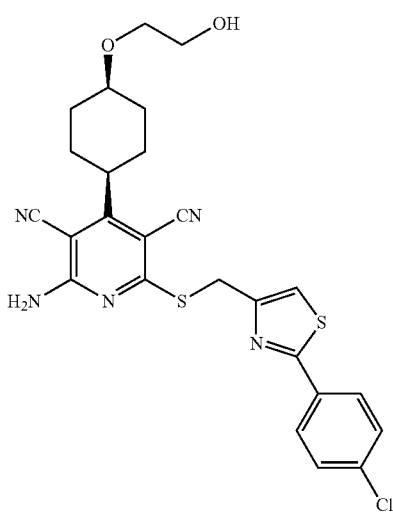

43 mg (0.06 mmol) of the compound from Example 7A (cis isomer) are dissolved in 5 ml of dry THF, 22 mg (0.08 mmol) of tetra-n-butylammonium fluoride are added and the mixture is stirred at RT for 20 h. 15 ml of ethyl acetate are then added to the mixture. The mixture is washed twice with in each case 3 ml of saturated aqueous sodium bicarbonate solution. The organic phase is dried over magnesium sulfate. After removal of the solvent on a rotary evaporator the crude product is purified chromatographically initially by preparative HPLC (column: YMC GEL ODS-AQ S-5/15 µm; mobile phase gradient: acetonitrile/water 10:90→95:5) and then once more on silica gel 60 (mobile phase: gradient dichloromethane/ethanol 200:1→10:1).

Yield: 21 mg (68% of theory)

$^1$H-NMR (400 MHz, DMSO-d$_6$): δ=8.18-7.82 (br. s, 2H), 7.93 (d, 2H), 7.88 (s, 1H), 7.57 (d, 2H), 4.58 (s, 2H), 4.31 (t, 1H), 3.61 (s, 1H), 3.56-3.48 (m, 2H), 3.43-3.36 (m, 2H), 2.95-2.84 (m, 1H), 2.36-2.20 (m, 2H), 2.03-1.92 (m, 2H), 1.49-1.37 (m, 4H).

LC-MS (Method 7): R$_t$=3.89 min; MS (ESIpos): m/z=526 [M+H]$^+$.

Example 3

2-Amino-6-({[2-(4-chlorophenyl)-1,3-thiazol-4-yl]methyl}thio)-4-(trans-4-hydroxycyclohexyl)-pyridine-3,5-dicarbonitrile

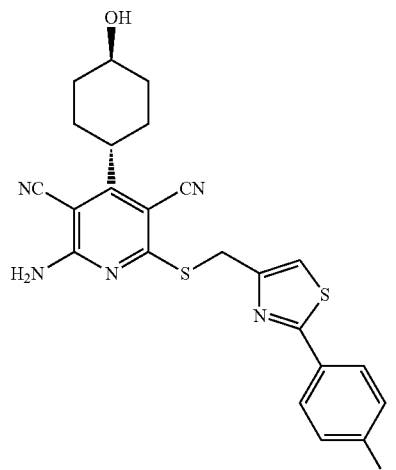

25 mg (0.04 mmol) of the compound from Example 13A (trans isomer) are dissolved in 1 ml of dry acetonitrile, and 0.1 ml (2.30 mmol) of 40% strength hydrofluoric acid is added. The reaction mixture is stirred at RT for 2 h. The mixture is then directly purified by preparative HPLC (column: YMC GEL ODS-AQ S-5/15 µm; mobile phase gradient: acetonitrile/water 10:90→95:5).

Yield: 20 mg (99% of theory)

$^1$H-NMR (400 MHz, DMSO-d$_6$): δ=8.21-7.81 (br. s, 2H), 7.94 (d, 2H), 7.88 (s, 1H), 7.56 (d, 2H), 4.70 (d, 1H), 4.58 (s, 2H), 3.48-3.37 (m, 1H), 2.85-2.75 (m, 1H), 2.06-1.92 (m, 4H), 1.77-1.68 (m, 2H), 1.28-1.14 (m, 2H).

LC-MS (Method 7): R$_t$=3.65 min; MS (ESIpos): m/z=482 [M+H]$^+$.

The compounds listed in the table below are prepared analogously to Example 3 from the appropriate starting materials:

| Example No. | Structure (yield) | LC-MS: R$_t$ [min] (Method); MS (ESI): m/z [M + H]$^+$ | $^1$H-NMR (DMSO-d$_6$): δ = |
|---|---|---|---|
| 4 | 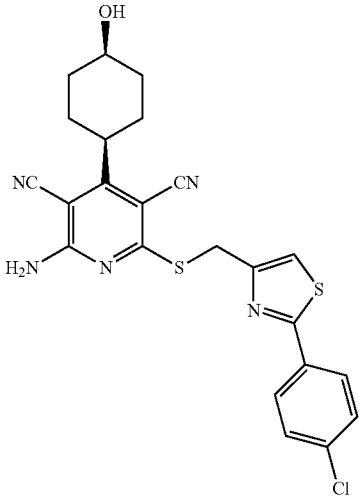<br>(88% of theory) | 3.75 min (7);<br>m/z = 482 | 8.21-7.80 (br. s, 2H), 7.92 (d, 2H), 7.88 (s, 1H), 7.56 (d, 2H), 4.59 (s, 2H), 4.38 (d, 1H), 3.90 (br. s, 1H), 2.89-2.79 (m, 1H), 2.45-2.31 (m, 2H), 1.83-1.73 (m, 2H), 1.52-1.35 (m, 4H). |
| 5 | 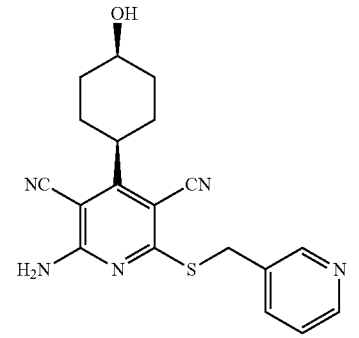<br>(33% of theory) | 1.49 min (4);<br>m/z = 366 | 8.74 (s, 1H), 8.43 (d, 1H), 8.27-7.70 (br. s, 2H), 7.92 (d, 1H), 7.37-7.29 (m, 1H), 4.45 (s, 2H), 4.38 (br. s, 1H), 3.89 (br. s, 1H), 2.99-2.78 (m, 1H), 2.45-2.29 (m, 2H), 1.83-1.72 (m, 2H), 1.51-1.36 (m, 4H). |
| 6 | 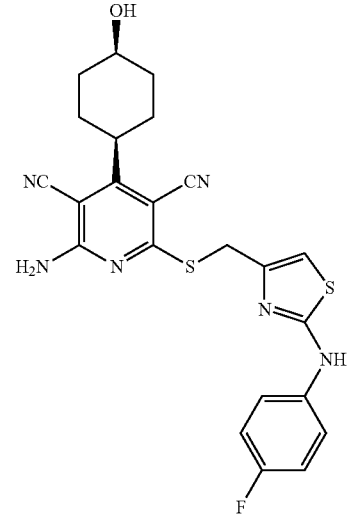<br>(96% of theory) | 2.40 min (13);<br>m/z = 481 | 10.21 (s, 1H), 8.16-7.75 (br. s, 2H), 7.60 (dd, 2H), 7.12 (pseudo-t, 2H), 6.93 (s, 1H), 4.40 (s, 2H), 4.38 (d, 1H), 3.90 (br. s, 1H), 2.90-2.80 (m, 1H), 2.47-2.31 (m, 2H), 1.83-1.73 (m, 2H), 1.51-1.38 (m, 4H). |

Example 7

2-Amino-6-[({2-[(4-fluorophenyl)amino]-1,3-thiazol-4-yl}methyl)thio]-4-piperidin-4-ylpyridine-3,5-dicarbonitrile

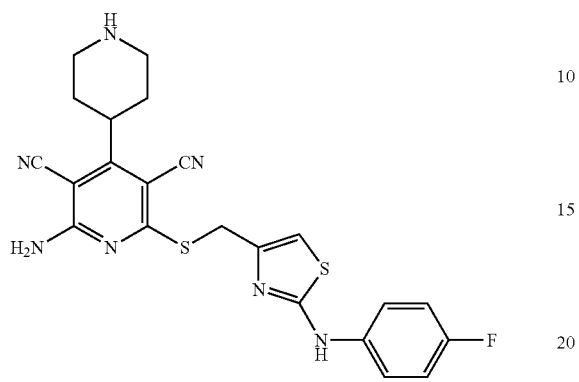

40 mg (0.07 mmol) of the compound from Example 18A are dissolved in 0.9 ml of dioxane, and 0.9 ml of a 4 M solution of hydrogen chloride in dioxane are added. The reaction mixture is stirred at RT for 2 h and then directly purified by preparative HPLC (column: YMC GEL ODS-AQ S-5, 15 μm; mobile phase gradient: acetonitrile/water 10:90→95:5).

Yield: 17 mg (52% of theory)

$^1$H-NMR (500 MHz, DMSO-$d_6$): δ=10.27 (s, 1H), 8.20-7.72 (br. s, 2H), 7.61 (dd, 2H), 7.12 (dd, 2H), 6.93 (s, 1H), 4.40 (s, 2H), 3.74-3.66 (m, 1H), 3.53-3.37 (m, 2H), 3.04 (d, 2H), 2.96-2.87 (m, 1H), 2.10-1.91 (m, 2H), 1.54 (d, 2H).

LC-MS (Method 12): $R_t$=1.52 min; MS (ESIpos): m/z=466 [M+H]$^+$.

Example 8

2-Amino-6-({[2-(4-chlorophenyl)-1,3-thiazol-4-yl]methyl}thio)-4-piperidin-4-ylpyridin-3,5-dicarbonitrile

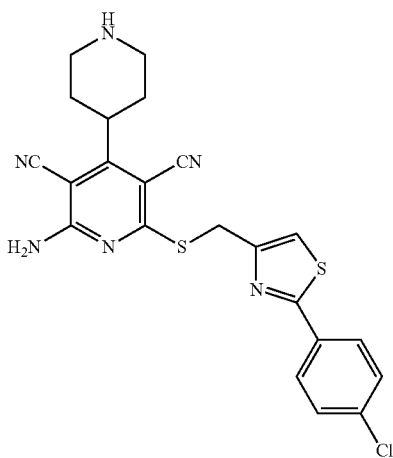

The title compound is obtained in an analogous manner from Example 19A.

Yield: 57% of theory

LC-MS (Method 12): $R_t$=1.74 min; MS (ESIpos): m/z=467 [M+H]$^+$.

Example 9

2-Amino-6-({[2-(4-chlorophenyl)-1,3-thiazol-4-yl]methyl}thio)-4-(1-glycoloylpiperidin-4-yl)-pyridine-3,5-dicarbonitrile

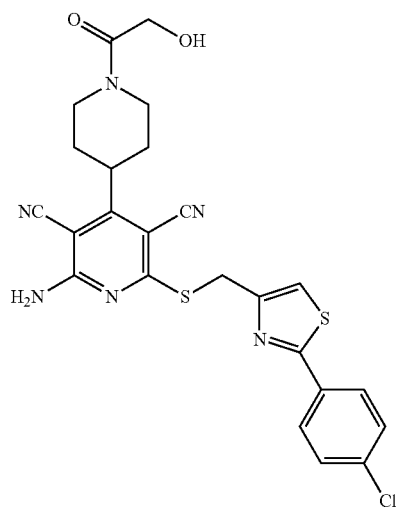

29 mg (0.05 mmol) of the compound from Example 25A are dissolved in a mixture of 1.5 ml of dioxane and 0.8 ml of water, and 2.4 mg (0.10 mmol) of lithium hydroxide are added. The reaction mixture is stirred at RT for two hours. After removal of the solvent on a rotary evaporator the residue is purified by preparative HPLC (column: YMC GEL ODS-AQ S-5, 15 μm; mobile phase gradient: acetonitrile/water 10:90→95:5).

Yield: 13 mg (47% of theory)

$^1$H-NMR (400 MHz, DMSO-$d_6$): δ=8.29-7.83 (br. s, 2H), 7.94 (d, 2H), 7.89 (s, 1H), 7.57 (d, 2H), 4.61-4.47 (m, 2H), 4.48 (s, 2H), 4.17-4.03 (m, 2H), 3.89-3.78 (m, 1H), 3.19-2.97 (m, 2H), 2.72-2.61 (m, 1H), 2.13-1.90 (m, 2H), 1.80-1.69 (m, 2H).

LC-MS (Method 3): $R_t$=2.47 min; MS (ESIpos): m/z=525 [M+H]$^+$.

Example 10

3-{4-[2-Amino-6-({[2-(4-chlorophenyl)-1,3-thiazol-4-yl]methyl}thio)-3,5-dicyanopyridin-4-yl]-piperidin-1-yl}propyl acetate

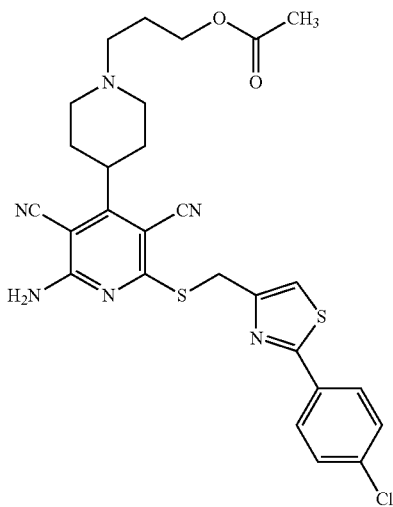

60 mg (0.16 mmol) of the compound from Example 29A are dissolved in 3 ml of dry DMF, and 46 mg (0.19 mmol) of 4-(chloromethyl)-2-(4-chlorophenyl)-1,3-thiazole and 53 mg (0.63 mmol) of sodium bicarbonate are added in succession. The reaction mixture is stirred at RT for 8 h. After removal of the solvent on a rotary evaporator the residue is directly purified by preparative HPLC (column: YMC GEL ODS-AQ S-5, 15 µm; mobile phase gradient: acetonitrile/water 10:90→95:5).

Yield: 65 mg (72% of theory)

LC-MS (Method 3): $R_t$=1.77 min; MS (ESIpos): m/z=568 [M+H]$^+$.

The compounds listed in the table below are prepared analogously to Example 10 from the appropriate starting materials:

| Example No. | Structure (yield) | LC-MS: $R_t$ [min] (Method); MS (ESI): m/z [M + H]$^+$ | $^1$H-NMR (DMSO-d$_6$): δ = |
|---|---|---|---|
| 11 | (structure shown) (12% of theory) | 1.71 min (4); m/z = 566 | 10.21 (s, 1H), 8.20-7.87 (br. s, 2H), 7.59 (dd, 2H), 7.12 (pseudo-t, 2H), 6.92 (s, 1H), 4.41 (s, 2H), 4.02 (t, 2H), 3.06-2.97 (m, 2H), 2.88-2.78 (m, 1H), 2.42-2.30 (m, 2H), 2.24-2.11 (m, 2H), 2.01 (s, 3H), 1.98-1.87 (m, 2H), 1.80-1.69 (m, 2H), 1.69-1.60 (m, 2H). |

| Example No. | Structure (yield) | LC-MS: $R_t$ [min] (Method); MS (ESI): m/z [M + H]$^+$ | $^1$H-NMR (DMSO-d$_6$): δ = |
|---|---|---|---|
| 12 | 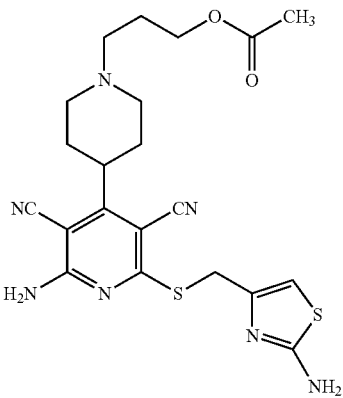 (54% of theory) | 2.27 min (14); m/z = 472 | |

Example 13

2-Amino-6-({[2-(4-chlorophenyl)-1,3-thiazol-4-yl]methyl}thio)-4-[1-(3-hydroxypropyl)piperidin-4-yl]pyridine-3,5-dicarbonitrile

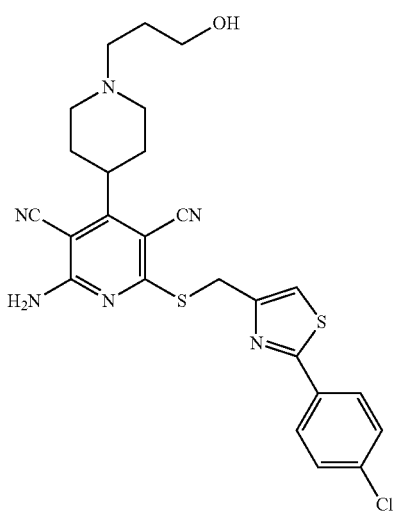

65 mg (0.12 mmol) of the compound from Example 10 are initially charged in a mixture of 3.5 ml of dioxane and 1.7 ml of water, and 11 mg of lithium hydroxide are added. The mixture is initially stirred at RT for 8 h. Another 22 mg of lithium hydroxide are then added, and the mixture is stirred at RT for a further 16 h. The solvent is then removed on a rotary evaporator. The residue is taken up in 10 ml ethyl acetate and washed once with 3 ml of saturated aqueous sodium bicarbonate solution. The mixture is dried over magnesium sulfate. After removal of the solvent on a rotary evaporator the residue is purified chromatographically on silica gel 60 (mobile phase: gradient dichloromethane/ethanol 50:1→10:1).

Yield: 12 mg (19% of theory)

$^1$H-NMR (400 MHz, DMSO-d$_6$): δ=8.25-7.77 (br. s, 2H), 7.94 (d, 2H), 7.87 (s, 1H), 7.56 (d, 2H), 4.59 (s, 2H), 4.41 (br. s, 1H), 3.42 (br. s, 2H), 3.00 (d, 2H), 2.88-2.77 (m, 1H), 2.40-2.29 (m, 2H), 2.24-2.10 (m, 2H), 1.97-1.85 (m, 2H), 1.70-1.52 (m, 4H).

LC-MS (Method 5): $R_t$=2.67 min; MS (ESIpos): m/z=525 [M+H]$^+$.

Example 14 rac-2-Amino-6-({[2-(4-chlorophenyl)-1,3-thiazol-4-yl]methyl}thio)-4-(tetrahydro-2H-pyran-2-yl)-pyridine-3,5-dicarbonitrile

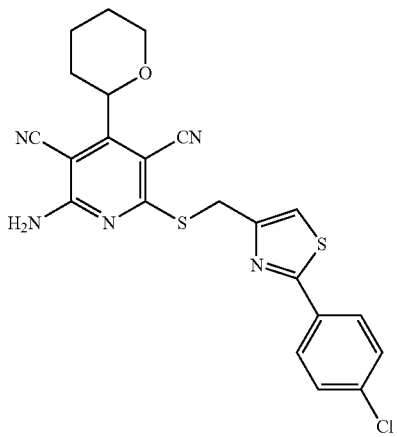

33 mg (0.10 mmol) of the compound from Example 31A, 29 mg (0.12 mmol) of 4-(chloromethyl)-2-(4-chlorophenyl)-1,3-thiazole and 33 mg (0.39 mmol) of sodium bicarbonate are suspended in 2 ml of dry DMF. The reaction mixture is stirred at RT for 20 h. The mixture is filtered and directly purified by preparative HPLC (column: YMC GEL ODS-AQ S-5, 15 μm; mobile phase gradient: acetonitrile/water 10:90→95:5).

Yield: 30 mg (66% of theory)

$^1$H-NMR (400 MHz, DMSO-d$_6$): δ=8.27-7.82 (br. s, 2H), 7.93 (d, 2H), 7.87 (s, 1H), 7.55 (d, 2H), 4.59 (s, 2H), 4.57-4.50 (m, 1H), 4.01 (d, 1H), 3.55-3.47 (m, 1H), 1.97-1.83 (m, 1H), 1.74-1.48 (m, 5H).

LC-MS (Method 4): $R_t$=3.15 min; MS (ESIpos): m/z=468 [M+H]$^+$.

Example 15 and Example 16 ent-2-Amino-6-({[2-(4-chlorophenyl)-1,3-thiazol-4-yl]methyl}thio)-4-(tetrahydro-2H-pyran-2-yl)-pyridine-3,5-dicarbonitrile (Enantiomer 1 and Enantiomer 2)

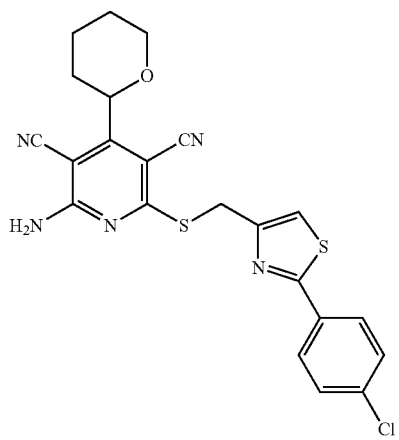

20 mg of the compound from Example 14 are dissolved in 0.5 ml of methanol and 4.5 ml of tert-butyl methyl ether and separated into the enantiomers by preparative HPLC on a chiral phase (Method 10):

Example 15

Enantiomer 1

Yield: 8 mg

HPLC (Method 10): $R_t$=8.13 min; ee>98%.

Example 16

Enantiomer 2

Yield: 9 mg

HPLC (Method 10): $R_t$=8.62 min; ee>98%.

The compounds listed in the table below are prepared in racemic form analogously to Example 14 from the appropriate starting materials:

| Example No. | Structure (yield) | LC-MS: $R_t$ [min] (Method); MS (ESI): m/z [M + H]$^+$ | $^1$H-NMR (DMSO-d$_6$): δ = |
|---|---|---|---|
| 17 | (39% of theory) | 1.71 min (4); m/z = 467 | 10.20 (s, 1H), 8.19-7.83 (br. s, 2H), 7.58 (dd, 2H), 7.11 (pseudo-t, 2H), 6.91 (s, 1H), 4.59-4.52 (m, 1H), 4.40 (s, 2H), 4.03 (d, 1H), 3.56-3.47 (m, 1H), 1.96-1.87 (m, 1H), 1.75-1.50 (m, 5H). |

| Example No. | Structure (yield) | LC-MS: $R_t$ [min] (Method); MS (ESI): m/z [M + H]$^+$ | $^1$H-NMR (DMSO-d$_6$): δ = |
|---|---|---|---|
| 18 | 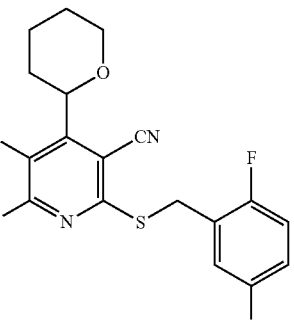<br>(45% of theory) | 2.48 min (12); m/z = 387 | 8.36-7.74 (br. s, 2H), 7.65-7.59 (m, 1H), 7.31-7.22 (m, 1H), 7.21-7.12 (m, 1H), 4.57-4.50 (m, 1H), 4.45 (s, 2H), 4.02 (s, 1H), 3.54-3.43 (m, 1H), 1.96-1.84 (m, 1H), 1.75-1.50 (m, 5H). |
| 19 | 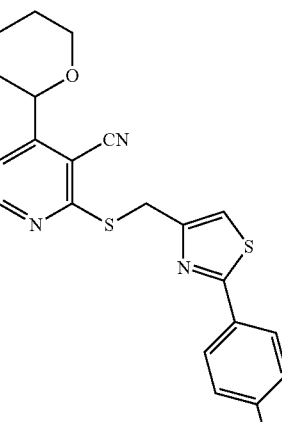<br>(49% of theory) | 4.22 min (5); m/z = 506 | 8.30-7.89 (br. s, 2H), 8.03 (s, 4H), 7.96 (s, 1H), 4.62 (s, 2H), 4.57-4.50 (m, 1H), 4.34 (q, 2H), 4.02 (d, 1H), 3.54-3.46 (m, 1H), 1.93-1.87 (m, 1H), 1.73-1.51 (m, 5H), 1.33 (t, 3H). |

Example 20 and Example 21 ent-Ethyl 4-[4-({[6-amino-3,5-dicyano-4-(tetrahydro-2H-pyran-2-yl)pyridin-2-yl]thio}methyl)-1,3-thiazol-2-yl]benzoate (Enantiomer 1 and Enantiomer 2)

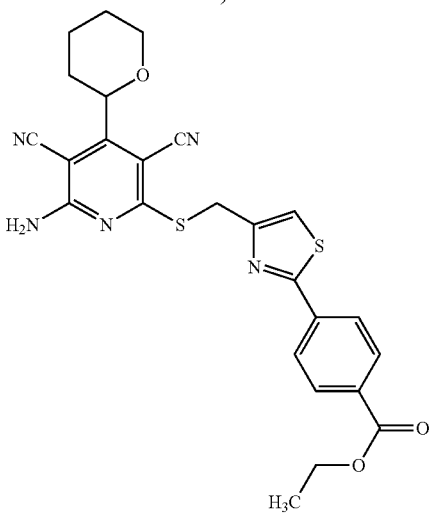

500 mg of the compound from Example 19 are dissolved at about 40° C. in 35 ml of 2-propanol and separated into the enantiomers by preparative HPLC on a chiral phase (Method 11):

Example 20

Enantiomer 1

Yield: 231 mg

HPLC (Method 11): $R_t$=9.70 min; ee>99% optical rotation: −0.059° (c=0.45 g/100 ml, chloroform).

Example 21

Enantiomer 2

Yield: 209 mg

HPLC (Method 11): $R_t$=11.74 min; ee>98% optical rotation: +0.054° (c=0.49 g/100 ml, chloroform).

Example 22 rac-4-[4-({[6-Amino-3,5-dicyano-4-(tetrahydro-2H-pyran-2-yl)pyridin-2-yl]thio}methyl-1,3-thiazol-2-yl]benzoic acid

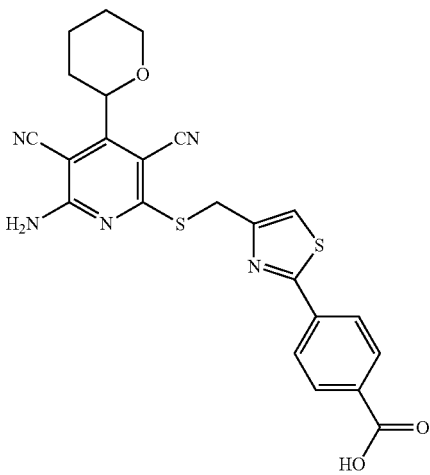

50 mg (0.10 mmol) of the compound from Example 19 and 16 mg (0.40 mmol) of sodium hydroxide are dissolved in a mixture of 4 ml of 1,2-dimethoxyethane, 1 ml of ethanol and 4 ml of water. The reaction mixture is stirred at RT for 3 h. After removal of the solvent the mixture is directly purified by preparative HPLC (column: YMC GEL ODS-AQ S-5, 15 μm; mobile phase gradient: acetonitrile/water 10:90→95:5 with addition of 0.1% hydrochloric acid).

Yield: 29 mg (61% of theory)

$^1$H-NMR (400 MHz, DMSO-$d_6$): δ=8.26-7.85 (br. s, 2H), 7.91 (d, 2H), 7.79 (s, 1H), 7.78 (d, 2H), 4.60 (s, 2H), 4.58-4.51 (m, 1H), 4.03 (d, 1H), 3.55-3.46 (m, 1H), 1.96-1.84 (m, 1H), 1.76-1.50 (m, 5H).

LC-MS (Method 5): $R_t$=3.53 min; MS (ESIpos): m/z=478 [M+H]$^+$.

The enantiomers listed in the table below are obtained in an analogous manner from Example 20 or Example 21:

| Example No. | Structure (yield) | LC-MS: $R_t$ [min] (Method); MS (ESI): m/z [M + H]$^+$ optical rotation | $^1$H-NMR (DMSO-$d_6$): δ = |
|---|---|---|---|
| 23 (ent-1) | 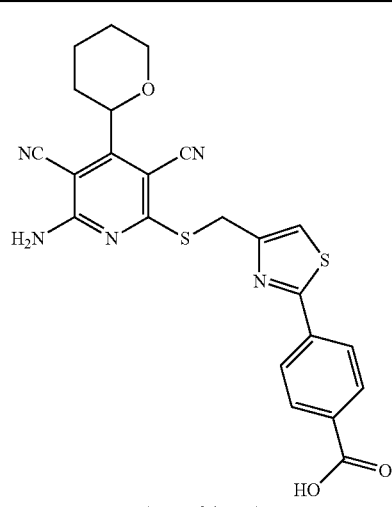<br>(69% of theory) | 3.53 min (5); m/z = 478; +0.025° (c = 0.465 g/100 ml, methanol) | 13.18 (s, 1H), 8.31-7.85 (br. s, 2H), 8.04 (s, 4H), 7.94 (s, 1H), 4.61 (s, 2H), 4.57-4.51 (m, 1H), 4.03 (dd, 1H), 3.55-3.46 (m, 1H), 1.95-1.86 (m, 1H), 1.74-1.50 (m, 5H). |

| Example No. | Structure (yield) | LC-MS: $R_t$ [min] (Method); MS (ESI): m/z [M + H]$^+$ optical rotation | $^1$H-NMR (DMSO-d$_6$): δ = |
|---|---|---|---|
| 24 (ent-2) | 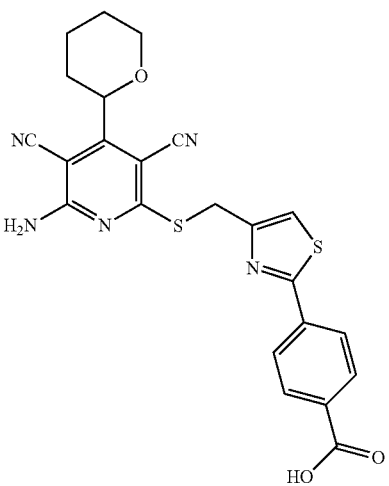 (59% of theory) | 3.53 min (5); m/z = 478; −0.032° (c = 0.465 g/ 100 ml, methanol) | |

Example 25 rac-2-({[2-(4-Chlorophenyl)-1,3-thiazol-4-yl]methyl}thio)-4-(tetrahydro-2H-pyran-2-yl)pyridine-3,5-dicarbonitrile

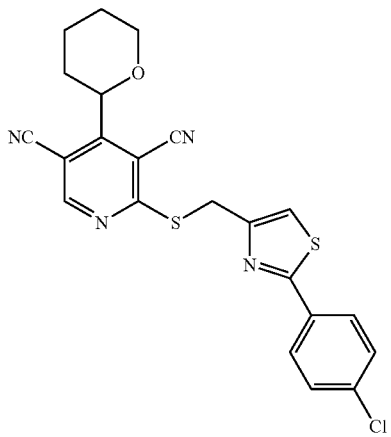

100 mg (0.21 mmol) of the compound from Example 14 are initially charged in 5 ml of dry THF, and 167 mg (1.42 mmol) of isopentyl nitrite and 3 mg (0.02 mmol) of copper(II) chloride are added. The reaction mixture is stirred at RT for 8 h. Another 3 mg (0.02 mmol) of copper(II)-chloride are added, and the reaction mixture is stirred at RT for another 12 h. 6 ml of 1 N hydrochloric acid are then added to the mixture. The aqueous phase is extracted twice with in each case 10 ml ethyl acetate. The combined organic phases are washed once with 5 ml of saturated aqueous sodium bicarbonate solution and once with 5 ml of saturated aqueous sodium chloride solution. The mixture is then dried over magnesium sulfate. After removal of the solvent the residue is purified by preparative HPLC (column: YMC GEL ODS-AQ S-5, 15 μm; mobile phase gradient: acetonitrile/water 10:90→95:5).

Yield: 43 mg (44% of theory)

$^1$H-NMR (400 MHz, DMSO-d$_6$): δ=13.19 (s, 1H), 9.12 (s, 1H), 8.04 (s, 4H), 7.81 (s, 1H), 4.79-4.70 (m, 1H), 4.68 (s, 2H), 4.08 (dd, 1H), 3.63-3.53 (m, 1H), 1.99-1.79 (m, 1H), 1.87-1.74 (m, 1H), 1.73-1.52 (m, 4H).

LC-MS (Method 4): $R_t$=2.69 min; MS (ESIpos): m/z=463 [M+H]$^+$.

Example 26 rac-2-Amino-6-({[2-(4-chlorophenyl)-1,3-thiazol-4-yl]methyl}thio)-4-(tetrahydro-2H-pyran-3-yl)-pyridine-3,5-dicarbonitrile

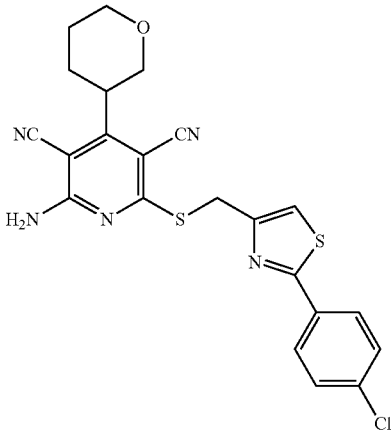

50 mg (0.13 mmol) of the compound from Example 32A, 39 mg (0.16 mmol) of 4-(chloromethyl)-2-(4-chlorophenyl)-1,3-thiazole and 45 mg (0.54 mmol) of sodium bicarbonate are initially charged in 3 ml of dry DMF. The reaction mixture is stirred at RT for 12 h and then directly purified by preparative HPLC (column: YMC GEL ODS-AQ S-5, 15 μm; mobile phase gradient: acetonitrile/water 10:90→95:5).

Yield: 37 mg (58% of theory)

¹H-NMR (400 MHz, DMSO-d₆): δ=8.28-7.83 (br. s, 2H), 7.93 (d, 2H), 7.88 (s, 1H), 7.57 (d, 2H), 4.59 (s, 2H), 3.97-3.88 (m, 1H), 3.86-3.79 (m, 2H), 3.20-3.09 (m, 1H), 2.23 (dq, 1H), 1.93-1.84 (m, 1H), 1.77-1.56 (m, 2H).

LC-MS (Method 7): $R_t$=3.98 min; MS (ESIpos): m/z=468 [M+H]⁺.

The compounds listed in the table below are prepared analogously to Example 26 from the appropriate starting materials:

| Example No. | Structure (yield) | LC-MS: $R_t$ [min] (Method); MS (ESI): m/z [M + H]⁺ | ¹H-NMR (DMSO-d₆): δ = |
|---|---|---|---|
| 27 | (31% of theory) | 3.54 min (7); m/z = 467 | 10.21 (s, 1H), 8.26-7.86 (br. s, 2H), 7.60 (dd, 2H), 7.13 (pseudo-t, 2H), 6.93 (s, 1H), 4.51 (s, 2H), 3.96-3.88 (m, 1H), 3.82 (d, 2H), 3.21-3.09 (m, 1H), 2.24 (dq, 1H), 1.89 (d, 1H), 1.78-1.56 (m, 2H). |
| 28 | (40% of theory) | 2.07 min (5); m/z = 373 | 8.19-7.80 (br. s, 2H), 6.98 (s, 2H), 6.61 (s, 1H), 4.24 (s, 2H), 3.96-3.89 (m, 1H), 3.86-3.79 (m, 2H), 3.20-3.09 (m, 1H), 2.24 (dq, 1H), 1.94-1.84 (m, 1H), 1.77-1.55 (m, 2H). |

Example 29

2-Amino-6-({[2-(4-chlorophenyl)-1,3-thiazol-4-yl]methyl}thio)-4-cyclohexylpyridine-3,5-dicarbonitrile

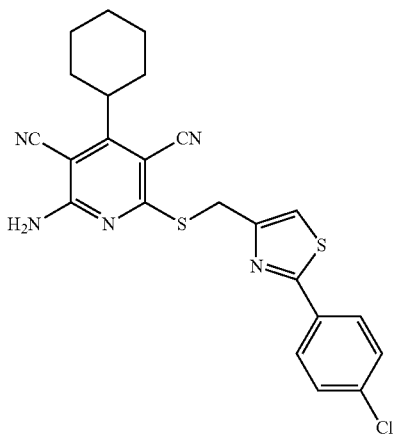

2.00 g (5.42 mmol) of the compound from Example 33A are initially charged in 111 ml of dry DMF, and 1.46 g (5.96 mmol) of 4-(chloromethyl)-2-(4-chlorophenyl)-1,3-thiazole and 1.82 g (21.68 mmol) of sodium bicarbonate are added. The reaction mixture is stirred at RT for 12 h. The mixture is then diluted with 20 ml of water and extracted twice with in each case 100 ml of ethyl acetate. The combined organic phases are washed once with 15 ml of saturated aqueous sodium bicarbonate solution and dried over magnesium sulfate. After removal of the solvent the residue is purified chromatographically on silica gel 60 (mobile phase: gradient cyclohexane/ethyl acetate 50:1→2:1).

Yield: 1.08 g (40% of theory)

$^1$H-NMR (400 MHz, DMSO-$d_6$): δ=8.20-7.80 (br. s, 2H), 7.93 (d, 2H), 7.88 (s, 1H), 7.57 (d, 1H), 4.59 (s, 2H), 2.92-2.80 (m, 1H), 2.01-1.88 (m, 2H), 1.87-1.77 (m, 2H), 1.76-1.60 (m, 3H), 1.37-1.10 (m, 3H).

LC-MS (Method 12): $R_t$=3.10 min; MS (ESIpos): m/z=466 [M+H]$^+$.

The compounds listed in the table below are prepared analogously to Example 29 from the appropriate starting materials:

| Example No. | Structure (yield) | LC-MS: $R_t$ [min] (Method); MS (ESI): m/z [M + H]$^+$ | $^1$H-NMR (DMSO-$d_6$): δ = |
|---|---|---|---|
| 30 | (31% of theory) | 2.79 min (12); m/z = 465 | 10.20 (s, 1H), 7.96 (br. s, 2H), 7.59 (dd, 2H), 7.11 (dd, 2H), 6.92 (s, 1H), 4.39 (s, 2H), 2.90-2.84 (m, 1H), 1.99-1.90 (m, 2H), 1.85-1.82 (m, 2H), 1.70-1.66 (m, 3H), 1.39-1.12 (m, 3H). |
| 31 | (40% of theory) | 2.15 min (15); m/z = 371 | 7.92 (br. s, 2H), 6.96 (s, 2H), 6.60 (s, 1H), 4.26 (s, 2H), 2.90-2.84 (m, 1H), 2.00-1.90 (m, 2H), 1.85-1.82 (m, 2H), 1.72-1.69 (m, 3H), 1.38-1.12 (m, 3H). |

| Example No. | Structure (yield) | LC-MS: $R_t$ [min] (Method); MS (ESI): m/z [M + H]$^+$ | $^1$H-NMR (DMSO-d$_6$): δ = |
|---|---|---|---|
| 32 | 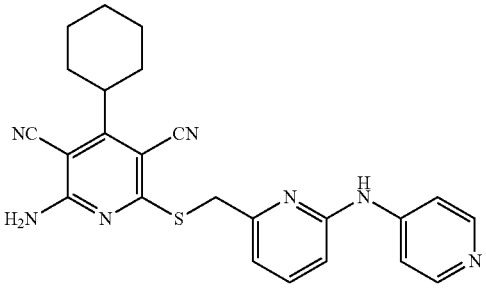<br>(10% of theory) | 1.87 min (13); m/z = 442 | 8.83 (d, 2H), 8.69 (s, 2H), 8.29-7.78 (br. s, 2H), 8.11 (t, 1H), 7.88 (d, 1H), 7.80 (d, 1H), 7.01 (d, 2H), 4.61 (s, 2H), 2.93-2.82 (m, 1H), 2.01-1.89 (m, 2H), 1.89-1.79 (m, 2H), 1.77-1.64 (m, 3H), 1.37-1.12 (m, 3H). |

Example 33

2-({[2-(4-Chlorophenyl)-1,3-thiazol-4-yl]methyl}thio)-4-cyclohexyl-6-{[3-(diethylamino)propyl]-amino}pyridine-3,5-dicarbonitrile

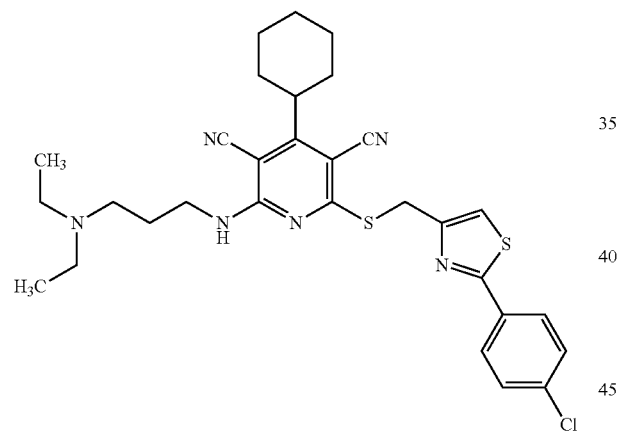

50 mg (0.10 mmol) of the compound from Example 37A and 30 mg (0.23 mmol) of 3-(diethylamino)propylamine are dissolved in 0.7 ml of dry DMF. The reaction mixture is stirred at RT for 12 h and then directly purified by preparative HPLC (column: YMC GEL ODS-AQ S-5, 15 µm; mobile phase gradient: acetonitrile/water 10:90→95:5).

Yield: 35 mg (58% of theory)

$^1$H-NMR (400 MHz, DMSO-d$_6$): δ=8.58 (t, 1H), 7.93 (d, 2H), 7.63 (s, 1H), 7.55 (d, 2H), 4.66 (s, 2H), 3.53-3.45 (m, 2H), 2.92-2.84 (m, 1H), 2.43-2.31 (m, 6H), 2.02-1.90 (m, 2H), 1.89-1.81 (m, 2H), 1.76-1.68 (m, 3H), 1.65-1.56 (m, 2H), 1.39-1.14 (m, 3H), 0.89 (t, 6H).

LC-MS (Method 2): $R_t$=4.66 min; MS (ESIpos): m/z=579 [M+H]$^+$.

The compounds listed in the table below are prepared analogously to Example 33 from the appropriate starting materials:

| Example No. | Structure (yield) | LC-MS: R_t [min] (Method); MS (ESI): m/z [M + H]+ | 1H-NMR (DMSO-d6): δ = |
|---|---|---|---|
| 34 | 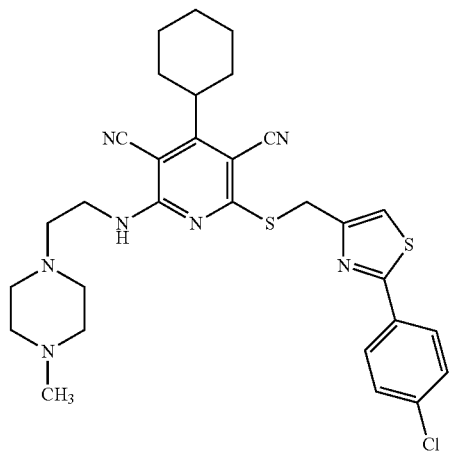 (64% of theory) | 4.51 min (2); m/z = 592 | 7.93 (d, 2H), 7.86-7.79 (m, 1H), 7.65 (s, 1H), 7.56 (d, 2H), 4.67 (s, 2H), 3.57-3.49 (m, 2H), 2.94-2.86 (m, 1H), 2.42 (t, 2H), 2.37-2.11 (m, 8H), 2.08 (s, 3H), 2.03-1.89 (m, 2H), 1.88-1.71 (m, 2H), 1.77-1.67 (m, 3H), 1.39-1.15 (m, 3H). |
| 35 | 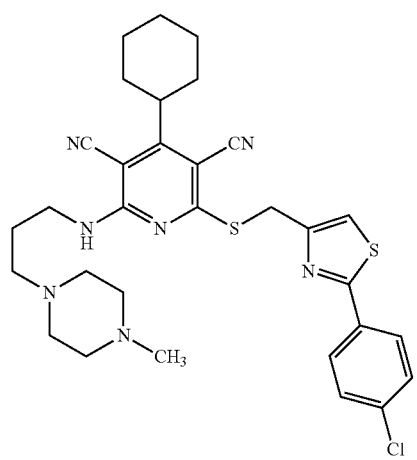 (8% of theory) | 4.66 min (2); m/z = 606 | 8.11 (t, 1H), 7.93 (d, 2H), 7.63 (s, 1H), 7.57 (d, 2H), 4.66 (s, 2H), 3.47 (q, 2H), 2.94-2.84 (m, 1H), 2.32-2.10 (m, 9H), 2.07 (s, 3H), 2.02-1.89 (m, 2H), 1.88-1.79 (m, 2H), 1.77-1.67 (m, 3H), 1.64-1.54 (m, 2H), 1.38-1.14 (m, 4H). |
| 36 | 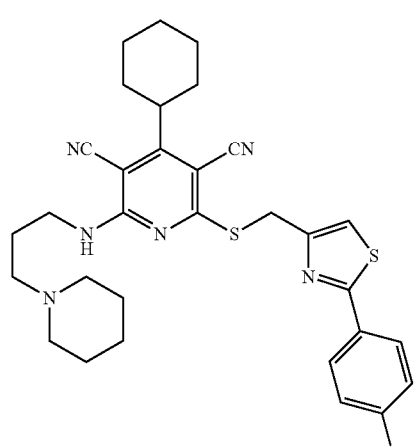 (69% of theory) | 4.63 min (2); m/z = 591 | 8.21-8.15 (m, 1H), 7.93 (d, 2H), 7.63 (s, 1H), 7.56 (d, 2H), 4.65 (s, 2H), 3.52-3.43 (m, 2H), 2.96-2.85 (m, 1H), 2.28-2.11 (m, 6H), 2.03-1.90 (m, 2H), 1.89-1.80 (m, 2H), 1.78-1.67 (m, 3H), 1.66-1.54 (m, 2H), 1.48-1.39 (m, 4H), 1.39-1.14 (m, 5H). |

| Example No. | Structure (yield) | LC-MS: R_t [min] (Method); MS (ESI): m/z [M + H]+ | 1H-NMR (DMSO-d6): δ = |
|---|---|---|---|
| 37 | (71% of theory) | 4.64 min (2); m/z = 577 | |
| 38 | (73% of theory) | 4.63 min (2); m/z = 577 | 8.79-8.73 (m, 1H), 7.92 (d, 2H), 7.63 (s, 1H), 7.56 (d, 2H), 4.67 (s, 2H), 3.61-3.02 (m, 1H), 3.48-3.33 (m, 1H), 2.93-2.84 (m, 2H), 2.19-2.12 (m, 1H), 2.18 (s, 3H), 2.03-1.88 (m, 3H), 1.87-1.66 (m, 7H), 1.65-1.51 (m, 3H), 1.50-1.40 (m, 1H), 1.38-1.13 (m, 3H). |
| 39 | (93% of theory) | 4.55 min (2); m/z = 593 | 8.18-8.09 (m, 1H), 7.93 (d, 2H), 7.64 (s, 1H), 7.58 (d, 2H), 4.66 (s, 2H), 3.54-3.41 (m, 6H), 2.96-2.84 (m, 1H), 2.30-2.16 (br. s, 6H), 2.03-1.91 (m, 2H), 1.89-1.79 (m, 2H), 1.77-1.66 (m, 3H), 1.65-1.55 (m, 2H), 1.39-1.13 (m, 3H). |

-continued
| Example No. | Structure (yield) | LC-MS: R_t [min] (Method); MS (ESI): m/z [M + H]+ | 1H-NMR (DMSO-d_6): δ = |
|---|---|---|---|
| 40 | 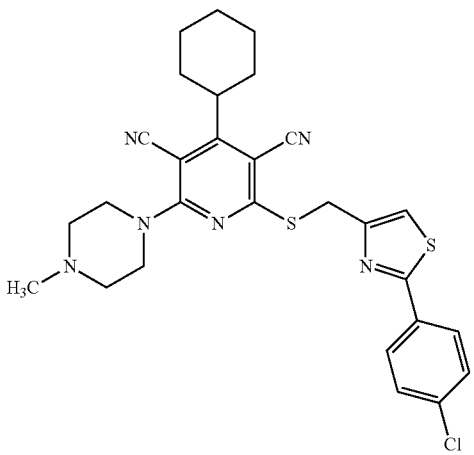<br>(92% of theory) | 2.53 min (12); m/z = 549 | 7.94 (d, 2H), 7.67 (s, 1H), 7.58 (d, 2H), 4.63 (s, 2H), 3.80 (br. s, 4H), 3.07-2.96 (m, 1H), 2.39-2.29 (m, 4H), 2.13 (s, 3H), 2.07-1.93 (m, 2H), 1.90-1.81 (m, 2H), 1.78-1.67 (m, 3H), 1.38-1.16 (m, 3H). |
| 41 | 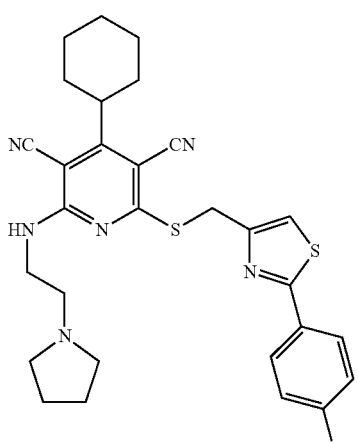<br>(47% of theory) | 2.09 min (12); m/z = 563 | 7.99-7.90 (m, 3H), 7.64 (s, 1H), 7.57 (d, 2H), 4.68 (s, 2H), 3.53 (q, 2H), 2.95-2.84 (m, 1H), 2.39-2.31 (m, 4H), 2.03-1.90 (m, 2H), 1.89-1.82 (m, 2H), 1.77-1.68 (m, 3H), 1.61-1.53 (m, 4H), 1.38-1.15 (m, 3H). |
| 42 | 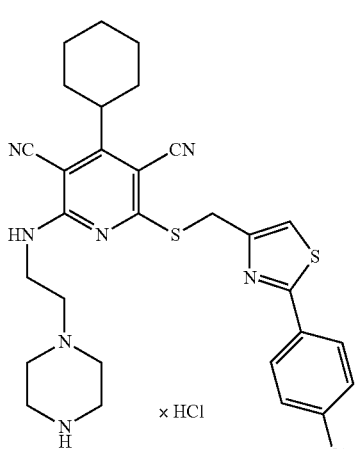<br>(77% of theory) | 2.20 min (12); m/z = 578 | |

Example 43

2-Amino-6-({[2-(4-chlorophenyl)-1,3-thiazol-4-yl]methyl}thio)-4-cyclohex-3-en-1-ylpyridine-3,5-dicarbonitrile

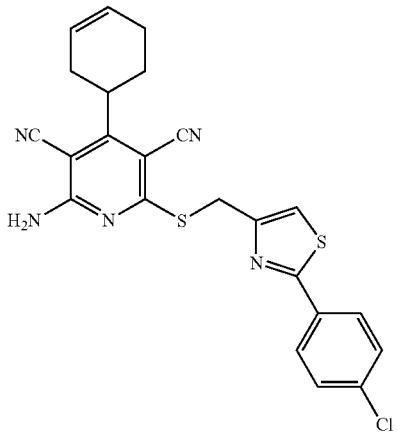

50 mg (0.20 mmol) of the compound from Example 38A, 52 mg (0.22 mmol) of 4-(chloromethyl)-2-(4-chlorophenyl)-1,3-thiazole and 49 mg (0.59 mmol) of sodium bicarbonate are initially charged in 2.5 ml of dry DMF. The reaction mixture is stirred at RT for 12 h and then directly purified by preparative HPLC (column: YMC GEL ODS-AQ S-5, 15 µm; mobile phase gradient: acetonitrile/water 10:90→95:5).

Yield: 42 mg (46% of theory)

$^1$H-NMR (400 MHz, DMSO-$d_6$): δ=8.26-7.86 (br. s, 2H), 7.94 (d, 2H), 7.89 (s, 1H), 7.58 (d, 2H), 5.81-5.71 (m, 2H), 4.60 (s, 2H), 3.13-3.03 (m, 1H), 2.26-2.08 (m, 4H), 1.83-1.76 (m, 1H).

LC-MS (Method 13): $R_t$=3.20 min; MS (ESIpos): m/z=464 [M+H]$^+$.

The compounds listed in the table below are prepared analogously to Example 43 from the appropriate starting materials:

| Example No. | Structure (yield) | LC-MS: $R_t$ [min] (Method); MS (ESI): m/z [M + H]$^+$ | $^1$H-NMR (DMSO-$d_6$): δ = |
|---|---|---|---|
| 44 | (47% of theory) | 1.82 min (12); m/z = 369 | 8.14-7.83 (br. s, 2H), 6.98 (s, 2H), 6.60 (s, 1H), 5.81-5.71 (m, 2H), 4.26 (s, 2H), 3.13-3.03 (m, 1H), 2.28-2.06 (m, 4H), 1.83-1.75 (m, 1H). |
| 45 | (23% of theory) | 2.83 min (13); m/z = 463 | 8.20-7.83 (br. s, 2H), 7.60 (dd, 2H), 7.13 (pseudo-t, 2H), 6.93 (s, 1H), 5.81-5.71 (m, 2H), 4.40 (s, 2H), 3.13-3.04 (m, 1H), 2.28-2.08 (m, 4H), 1.81-1.75 (m, 1H). |

Example 46

2-Amino-6-({[2-(4-chlorophenyl)-1,3-thiazol-4-yl]methyl}thio)-4-(tetrahydro-2H-pyran-4-yl)-pyridine-3,5-dicarbonitrile

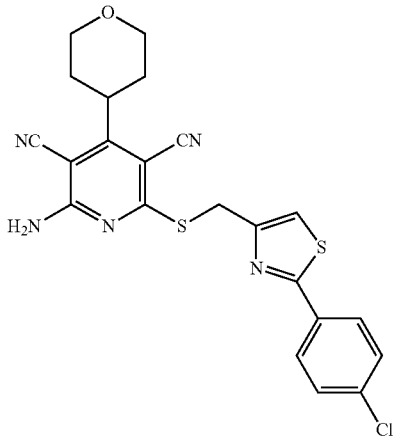

100 mg (0.34 mmol) of the compound from Example 34A, 83 mg (0.34 mmol) of 4-(chloromethyl)-2-(4-chlorophenyl)-1,3-thiazole and 57 mg (0.68 mmol) of sodium bicarbonate are initially charged in 5 ml of dry DMF. The reaction mixture is stirred at RT for 16 h. After removal of the solvent on a rotary evaporator the residue is triturated with about 2 ml of acetonitrile. This results in the formation of a precipitate which is filtered off with suction and dried.

Yield: 72 mg (45% of theory)

$^1$H-NMR (400 MHz, DMSO-$d_6$): δ=8.04 (br. s, 2H), 7.93 (d, 2H), 7.88 (s, 1H), 7.56 (d, 2H), 4.59 (s, 2H), 3.98 (dd, 2H), 3.39 (dd, 2H), 3.13 (m, 1H), 2.24-2.15 (m, 2H), 1.61 (d, 2H).

LC-MS (Method 15): $R_t$=2.96 min; MS (ESIpos): m/z=468 [M+H]$^+$.

The compounds listed in the table below are prepared analogously to Example 46 from the appropriate starting materials:

| Example No. | Structure (yield) | LC-MS: $R_t$ [min] (Method); MS (ESI): m/z [M + H]$^+$ | $^1$H-NMR (DMSO-$d_6$): δ = |
|---|---|---|---|
| 47 | (13% of theory) | 2.49 min (13); m/z = 467 | 10.21 (s, 1H), 8.05 (br. s, 1H), 7.60 (dd, 2H), 7.13 (t, 2H), 6.94 (s, 1H), 4.41 (s, 2H), 4.00 (dd, 2H), 3.38 (dd, 2H), 3.14 (m, 1H), 2.24-2.16 (m, 2H), 1.61 (d, 2H). |
| 48 | (35% of theory) | 1.55 min (13); m/z = 371 | 7.98 (br. s, 2H), 6.70 (s, 1H), 6.60 (s, 1H), 4.26 (s, 2H), 3.98 (dd, 2H), 3.38 (dd, 2H), 3.13 (m, 1H), 2.24-2.16 (m, 2H), 1.61 (d, 2H). |

Example 49

Methyl 3-({[6-amino-3,5-dicyano-4-(tetrahydro-2H-pyran-2-yl)pyridin-2-yl]thio}methyl)benzoate

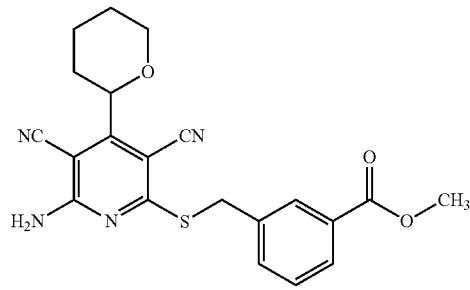

48 mg (0.58 mmol) of sodium bicarbonate are added to a solution of 50 mg (0.19 mmol) of the compound from Example 31A and 48 mg (0.21 mmol) of 3-(bromomethyl)benzoic acid methyl ester in 2 ml of dry DMF, and the mixture is stirred at RT for 20 h. The mixture is then directly purified by preparative HPLC (column: YMC GEL ODS-AQ S-5/15 μm; mobile phase gradient: acetonitrile/water 10:90→95:5).

Yield: 44 mg (53% of theory)

$^1$H-NMR (400 MHz, CDCl$_3$): δ=8.25-7.77 (br. s, 2H), 8.06 (s, 1H), 7.82 (pseudo-dd, 2H), 7.46 (t, 1H), 4.58-4.49 (m, 1H), 4.53 (s, 2H), 4.02 (dd, 1H), 3.85 (s, 3H), 3.55-3.45 (m, 1H), 1.97-1.85 (br. s, 1H), 1.73-1.51 (m, 5H).

LC-MS (Method 5): R$_t$=3.79 min; MS (ESIpos): m/z=409 [M+H]$^+$.

The compounds listed in the table below are prepared analogously to Example 49 from the appropriate starting materials:

Example 52

2-({[2-(4-Chlorophenyl)-1,3-thiazol-4-yl]methyl}sulfanyl)-6-methyl-4-(tetrahydro-2H-pyran-2-yl)-pyridine-3,5-dicarbonitrile

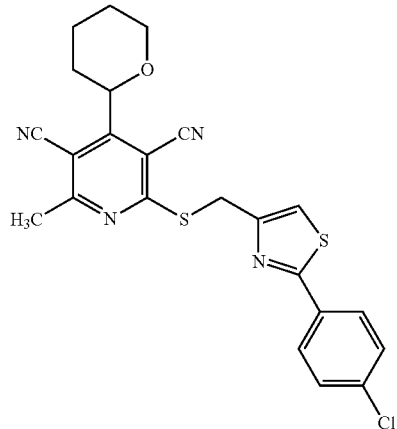

50 mg (0.14 mmol) of the compound from Example 41A, 40 mg (0.16 mmol) of 4-(chloromethyl)-2-(4-chlorophenyl)-1,3-thiazole and 45 mg (0.54 mmol) of sodium bicarbonate are reacted in 2.8 ml of dry DMF analogously to the preparation of the compound of Example 14.

Yield: 32 mg (50% of theory)

$^1$H-NMR (400 MHz, DMSO-d$_6$): δ=7.94 (d, 2H), 7.73 (s, 1H), 7.57 (d, 2H), 4.73 (s, 2H), 4.71-4.69 (m, 1H), 4.07 (dd, 1H), 3.62-3.53 (m, 1H), 2.78 (s, 3H), 2.00-1.89 (br. s, 1H), 1.82-1.72 (m, 1H), 1.71-1.53 (m, 4H).

| Example No. | Structure (yield) | LC-MS: R$_t$ [min] (Method); MS (ESI): m/z [M + H]$^+$ | $^1$H-NMR (DMSO-d$_6$): δ = |
|---|---|---|---|
| 50 | (structure: 6-amino-3,5-dicyano-4-(tetrahydro-2H-pyran-2-yl)pyridin-2-yl thiomethyl benzamide) (29% of theory) | 3.12 min (5); m/z = 394 | 8.21-7.82 (br. s, 2H), 7.99-7.94 (m, 2H), 7.76 (d, 1H), 7.66 (d, 1H), 7.43-7.35 (m, 2H), 4.57-4.45 (m, 1H), 4.49 (s, 2H), 4.03 (dd, 1H), 3.56-3.46 (m, 1H), 1.95-1.86 (br. s, 1H), 1.74-1.51 (m, 5H). |
| 51 | (structure: 6-amino-3,5-dicyano-4-(tetrahydro-2H-pyran-2-yl)pyridin-2-yl thiomethyl benzoic acid) (44% of theory) | 3.38 min (5); m/z = 395 | 13.0 (br. s, 1H), 8.30-7.71 (br. s, 2H), 8.02 (s, 1H), 7.79 (dd, 2H), 7.43 (t, 1H), 4.52 (s, 2H), 4.52-4.51 (m, 1H), 4.02 (d, 1H), 3.54-3.46 (m, 1H), 1.97-1.86 (br. s, 1H), 1.73-1.50 (m, 5H). |

Example 53 rac-Ethyl 4-[4-({[3,5-dicyano-6-methyl-4-(tetrahydro-2H-pyran-2-yl)pyridin-2-yl]sulfanyl}-methyl)-1,3-thiazol-2-yl]benzoate

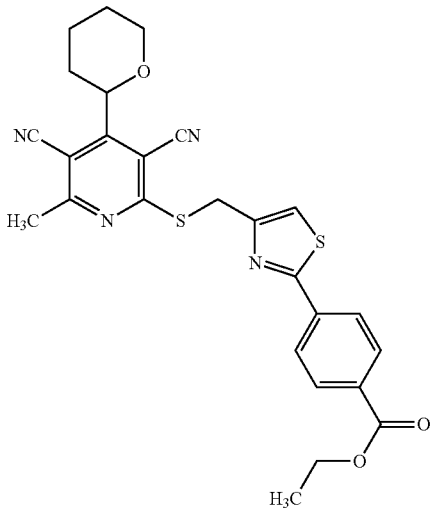

The title compound is obtained analogously to Example 52 from the appropriate starting materials.
Yield: 192 mg (37% of theory)
¹H-NMR (400 MHz, DMSO-$d_6$): δ=8.06 (d, 4H), 7.81 (s, 1H), 4.75 (s, 2H), 4.70 (d, 1H), 4.33 (q, 2H), 4.07 (dd, 1H), 3.62-3.53 (m, 1H), 2.79 (s, 3H), 1.99-1.89 (m, 1H), 1.82-1.73 (m, 1H), 1.70-1.55 (m, 4H), 1.34 (t, 3H).
LC-MS (Method 4): $R_t$=3.32 min; MS (ESIpos): m/z=505 [M+H]⁺.

Example 54 and Example 55 ent-Ethyl 4-[4-({[3,5-dicyano-6-methyl-4-(tetrahydro-2H-pyran-2-yl)pyridin-2-yl]sulfanyl}-methyl)-1,3-thiazol-2-yl]benzoate (Enantiomer 1 and Enantiomer 2)

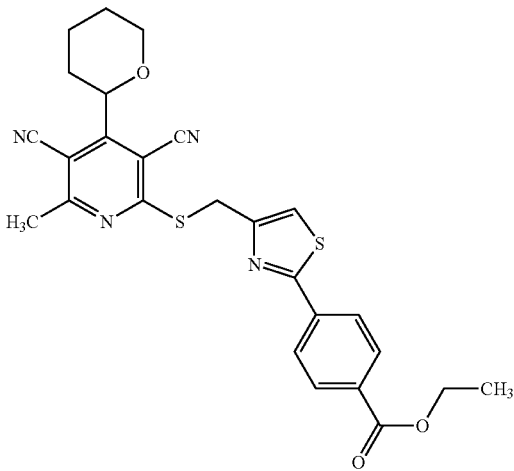

190 mg of the compound from Example 53 are dissolved at about 30° C. in 4 ml of methanol and 10 ml of TBME and separated into the enantiomers by preparative HPLC on a chiral phase (Method 16):

Example 54

Enantiomer 1

Yield: 90 mg
HPLC (Method 17): $R_t$=5.44 min; ee>99%
optical rotation: +0.073° (c=0.50 g/100 ml, chloroform).

Example 55

Enantiomer 2

Yield: 82 mg
HPLC (Method 17): $R_t$=5.83 min; ee>98%.

Example 56

(+)-4-[4-({[3,5-Dicyano-6-methyl-4-(tetrahydro-2H-pyran-2-yl)pyridin-2-yl]sulfanyl}methyl)-1,3-thiazol-2-yl]benzoic acid

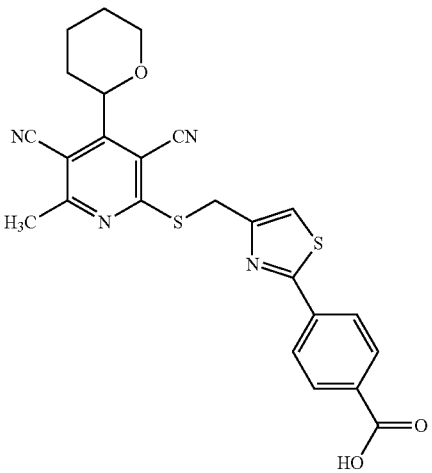

The title compound is obtained analogously to Example 22 from the compound of Example 54.
Yield: 17 mg (19% of theory)
¹H-NMR (400 MHz, DMSO-$d_6$): δ=13.22-13.13 (br. s, 1H), 8.04 (s, 4H), 7.71 (s, 1H), 4.76 (s, 2H), 4.74-4.68 (m, 1H), 4.06 (dd, 1H), 3.62-3.53 (m, 1H), 2.79 (s, 3H), 1.98-1.89 (m, 1H), 1.82-1.72 (m, 1H), 1.72-1.55 (m, 4H).
LC-MS (Method 4): $R_t$=2.84 min; MS (ESIpos): m/z=477 [M+H]⁺
optical rotation: +0.009° (c=0.17 g/100 ml, methanol).

Example 57

(−)-4-[4-({[3,5-Dicyano-6-methyl-4-(tetrahydro-2H-pyran-2-yl)pyridin-2-yl]sulfanyl}methyl)-1,3-thiazol-2-yl]benzoic acid

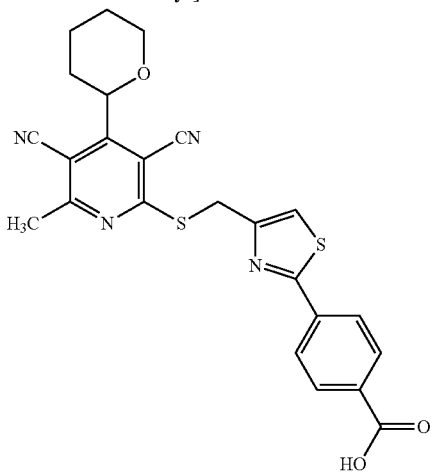

The title compound is obtained analogously to Example 22 from the compound of Example 55.

Yield: 11 mg (12% of theory)

$^1$H-NMR (400 MHz, DMSO-$d_6$): δ=13.22-13.11 (br. s, 1H), 8.04 (s, 4H), 7.70 (s, 1H), 4.76 (s, 2H), 4.74-4.68 (m, 1H), 4.07 (dd, 1H), 3.62-3.52 (m, 1H), 2.79 (s, 3H), 1.98-1.89 (m, 1H), 1.82-1.72 (m, 1H), 1.71-1.54 (m, 4H).

LC-MS (Method 22): $R_t$=2.39 min; MS (ESIpos): m/z=477 [M+H]$^+$.

Example 58

2-Amino-6-({[2-(4-chlorophenyl)-1,3-oxazol-4-yl]methyl}sulfanyl)-4-(tetrahydro-2H-pyran-3-yl)-pyridine-3,5-dicarbonitrile

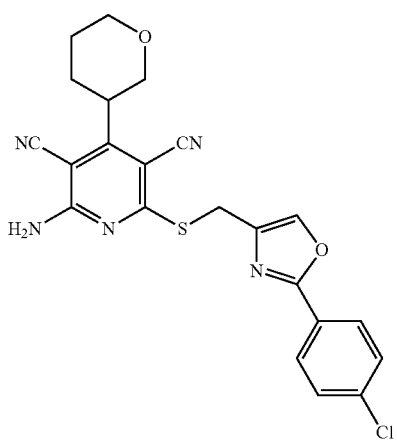

The title compound is obtained analogously to Example 14 from 200 mg (0.67 mmol) of the compound of Example 32A and 197 mg (0.74 mmol) of the compound of Example 42A.

Yield: 324 mg (95% of theory)

$^1$H-NMR (400 MHz, DMSO-$d_6$): δ=8.33 (s, 1H), 8.28-7.88 (br. s, 2H), 7.97 (d, 2H), 7.61 (d, 2H), 4.48 (s, 2H), 3.95-3.88 (m, 1H), 3.83 (s, 2H), 3.82-3.78 (m, 1H), 3.19-3.08 (m, 1H), 2.30-2.17 (m, 1H), 1.93-1.86 (m, 1H), 1.77-1.68 (m, 1H), 1.68-1.55 (m, 1H).

LC-MS (Method 4): $R_t$=2.87 min; MS (ESIpos): m/z=452 [M+H]$^+$.

Example 59 rac-Ethyl 4-[4-({[6-amino-3,5-dicyano-4-(tetrahydro-2H-pyran-3-yl)pyridin-2-yl]sulfanyl}methyl)-1,3-thiazol-2-yl]benzoate

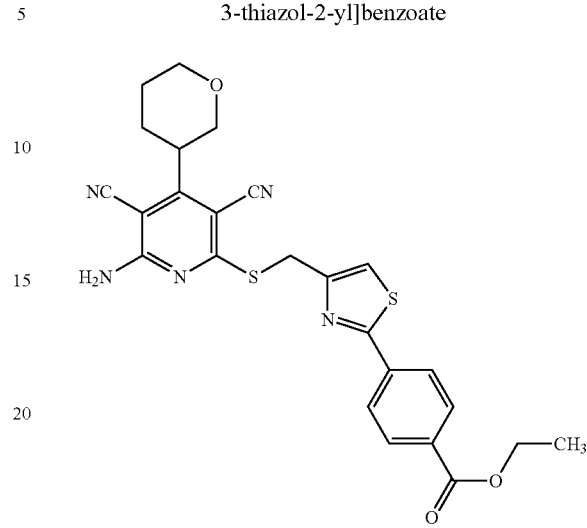

The title compound is obtained analogously to Example 14 from 282 mg (0.76 mmol) of the compound of Example 32A and 290 mg (0.83 mmol) of ethyl 4-[4-(chloromethyl)-1,3-thiazol-2-yl]benzoate.

Yield: 181 mg (47% of theory)

$^1$H-NMR (400 MHz, DMSO-$d_6$): δ=8.33-7.89 (br. s, 2H), 8.08 (s, 4H), 7.96 (s, 1H), 4.61 (s, 2H), 4.36 (q, 2H), 3.96-3.87 (m, 1H), 3.83 (s, 2H), 3.83-3.79 (m, 1H), 3.19-3.08 (m, 1H), 2.29-2.18 (m, 1H), 1.93-1.85 (m, 1H), 1.76-1.69 (m, 1H), 1.69-1.57 (m, 1H), 1.35 (t, 3H).

LC-MS (Method 4): $R_t$=2.87 min; MS (ESIpos): m/z=452 [M+H]$^+$.

Example 60 and Example 61 ent-Ethyl 4-[4-({[6-amino-3,5-dicyano-4-(tetrahydro-2H-pyran-3-yl)pyridin-2-yl]sulfanyl}methyl-1,3-thiazol-2-yl]benzoate (Enantiomer 1 and Enantiomer 2)

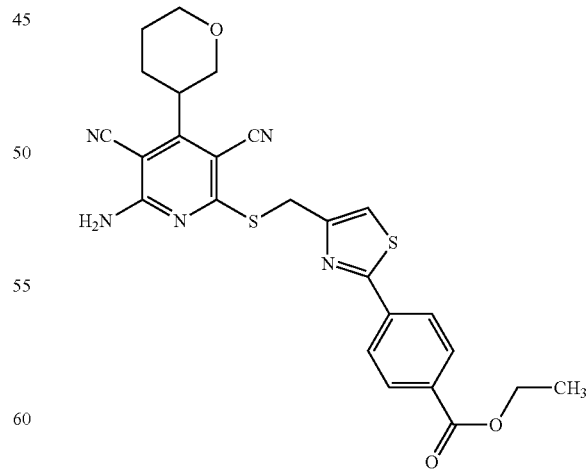

180 mg of the compound from Example 59 are dissolved at about 30° C. in 5 ml of methanol and 20 ml of TBME and separated into the enantiomers by preparative HPLC on a chiral phase (Method 18):

Example 60

Enantiomer 1

Yield: 59 mg
HPLC (Method 19): R$_t$=9.11 min; ee>99%
optical rotation: +0.057° (c=0.455 g/100 ml, chloroform).

Example 61

Enantiomer 2

Yield: 77 mg
HPLC (Method 19): R$_t$=10.29 min; ee>99%.

Example 62

(+)-4-[4-({[6-Amino-3,5-dicyano-4-(tetrahydro-2H-pyran-3-yl)pyridin-2-yl]sulfanyl}methyl)-1,3-thiazol-2-yl]benzoic acid

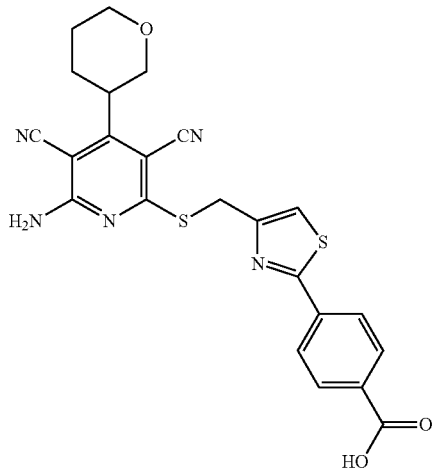

The title compound is obtained analogously to Example 22 from the compound of Example 60.

Yield: 18 mg (48% of theory)
$^1$H-NMR (400 MHz, DMSO-d$_6$): δ=13.23-13.10 (br. s, 1H), 8.35-7.83 (br. s, 2H), 8.05 (s, 4H), 7.96 (s, 1H), 4.61 (s, 2H), 3.91 (dd, 1H), 3.84-3.78 (m, 2H), 3.19-3.08 (m, 1H), 2.30-2.18 (m, 1H), 1.93-1.85 (m, 1H), 1.77-1.69 (m, 1H), 1.69-1.56 (m, 1H).
LC-MS (Method 4): R$_t$=2.41 min; MS (ESIpos): m/z=478 [M+H]$^+$.

Example 63

(−)-4-[4-({[6-Amino-3,5-dicyano-4-(tetrahydro-2H-pyran-3-yl)pyridin-2-yl]sulfanyl}methyl)-1,3-thiazol-2-yl]benzoic acid

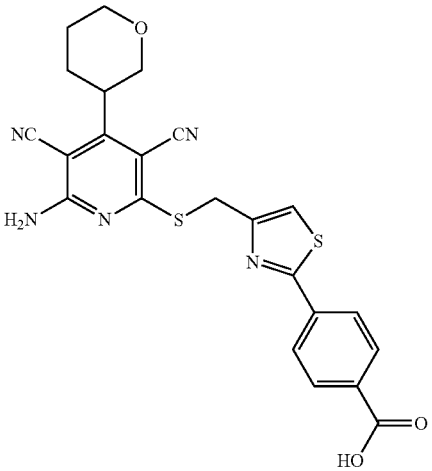

The title compound is obtained analogously to Example 22 from the compound of Example 61.

Yield: 30 mg (53% of theory)
$^1$H-NMR (400 MHz, DMSO-d$_6$): δ=13.22-13.13 (br. s, 1H), 8.29-7.88 (br. s, 2H), 8.04 (s, 4H), 7.95 (s, 1H), 4.60 (s, 2H), 3.92 (dd, 1H), 3.83-3.78 (m, 2H), 3.19-3.09 (m, 1H), 2.31-2.18 (m, 1H), 1.95-1.85 (m, 1H), 1.77-1.68 (m, 1H), 1.68-1.57 (m, 1H).
LC-MS (Method 4): R$_t$=2.42 min; MS (ESIpos): m/z=478 [M+H]$^+$
optical rotation: −0.050° (c=0.495 g/100 ml, methanol/dichloromethane 1:1).

Example 64 rac-4-[4-({[6-Amino-3,5-dicyano-4-(tetrahydro-2H-pyran-3-yl)pyridin-2-yl]sulfanyl}methyl)-1,3-thiazol-2-yl]benzoic acid

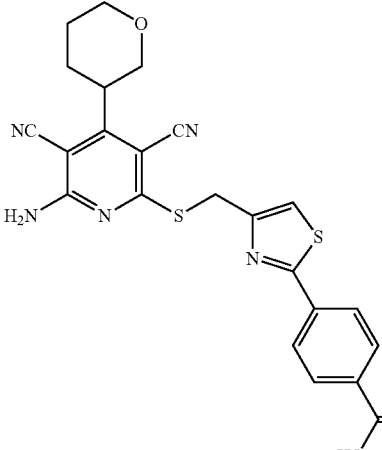

The title compound is obtained analogously to Example 22 from 69 mg (0.14 mmol) of the compound from Example 59.

Yield: 51 mg (78% of theory)

LC-MS (Method 5): $R_t$=3.37 min; MS (ESIpos): m/z=478 [M+H]$^+$.

Example 65 rac-4-[4-({[3,5-Dicyano-4-(tetrahydro-2H-pyran-3-yl)pyridin-2-yl]sulfanyl}methyl)-1,3-thiazol-2-yl]benzoic acid

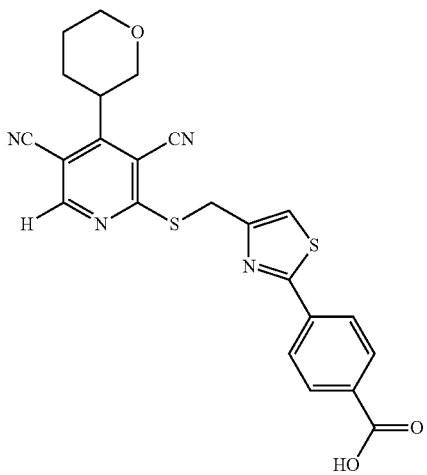

51 mg (0.11 mmol) of the compound from Example 64 are initially charged in 2.6 ml of dry THF, and 84 mg (0.72 mmol) of isopentyl nitrite and 1.43 mg (0.01 mmol) of copper(II) chloride are added. The reaction mixture is stirred at RT for 10 h. 4 ml of 1 N hydrochloric acid are then added to the mixture, and the aqueous phase is extracted twice with in each case 10 ml of ethyl acetate. The combined organic phases are washed once with 5 ml of saturated aqueous sodium bicarbonate solution and once with 5 ml of saturated aqueous sodium chloride solution and dried over magnesium sulfate. After removal of the solvent on a rotary evaporator the residue is purified by preparative HPLC (column: YMC GEL ODS-AQ S-5, 15 µm; mobile phase gradient: acetonitrile/water 10:90→95:5, with 0.3% hydrochloric acid). This gives a white solid.

Yield: 7 mg (14% of theory)

$^1$H-NMR (400 MHz, DMSO-d$_6$): δ=13.18 (s, 1H), 9.10 (s, 1H), 8.04 (s, 4H), 7.80 (s, 1H), 4.78 (s, 2H), 3.99-3.91 (m, 2H), 3.82 (t, 1H), 3.42-3.31 (m, 2H), 2.34-2.20 (m, 1H), 2.05-1.97 (m, 1H), 1.81-1.60 (m, 2H).

LC-MS (Method 7): $R_t$=3.45 min; MS (ESIpos): m/z=463 [M+H]$^+$.

Example 66 rac-Methyl N-[6-({[2-(4-chlorophenyl)-1,3-oxazol-4-yl]methyl}sulfanyl)-3,5-dicyano-4-(tetrahydro-2H-pyran-3-yl)pyridin-2-yl]-N-methylglycinate

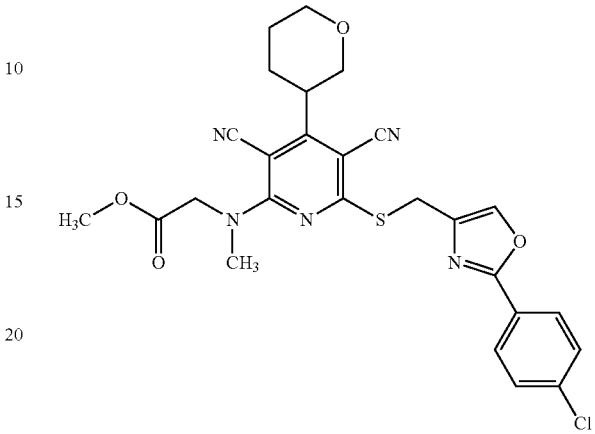

239 mg (0.42 mmol) of the compound from Example 43A are dissolved in 6 ml of dry THF, and 116 mg (0.83 mmol) of sarcosine methyl ester hydrochloride and 126 mg (1.25 mmol) of triethylamine are then added in succession. The reaction mixture is stirred at RT for 10 h. The solvent is then removed on a rotary evaporator and the residue is purified by preparative HPLC (column: YMC GEL ODS-AQ S-5, 15 µm; mobile phase gradient: acetonitrile/water 10:90→95:5).

Yield: 123 mg (55% of theory)

$^1$H-NMR (400 MHz, DMSO-d$_6$): δ=8.16 (s, 1H), 7.97 (d, 2H), 7.61 (d, 2H), 4.56 (s, 2H), 4.36 (s, 2H), 3.97-3.81 (m, 3H), 3.63 (s, 3H), 3.42 (s, 3H), 3.30 (s, 2H), 2.38-2.25 (m, 1H), 1.98-1.89 (m, 1H), 1.79-1.71 (m, 1H), 1.71-1.58 (m, 1H).

LC-MS (Method 2): $R_t$=2.47 min; MS (ESIpos): m/z=538 [M+H]$^+$.

Example 67 rac-3-({[6-Amino-3,5-dicyano-4-(tetrahydro-2H-pyran-2-yl)pyridin-2-yl]sulfanyl}methyl)benzamide

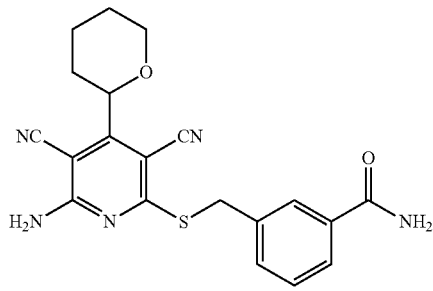

50 mg (0.14 mmol) of the compound from Example 31A, 36 mg (0.21 mmol) of 3-(chloromethyl)benzamide and 48 mg (0.58 mmol) of sodium bicarbonate in 2.0 ml of dry DMF are reacted analogously to the preparation of the compound of Example 14.

Yield: 23 mg (29% of theory)

¹H-NMR (400 MHz, DMSO-$d_6$): δ=8.20-7.82 (br. s, 2H), 7.99-7.93 (m, 2H), 7.76 (d, 1H), 7.65 (d, 1H), 7.43-7.34 (m, 2H), 4.57-4.45 (m, 1H), 4.49 (s, 2H), 4.02 (dd, 1H), 3.56-3.45 (m, 1H), 1.95-1.85 (br. s, 1H), 1.73-1.50 (m, 5H).

LC-MS (Method 5): $R_t$=3.12 min; MS (ESIpos): m/z=394 [M+H]⁺.

Example 68 rac-2-Amino-6-{[(2-amino-1,3-thiazol-4-yl)methyl]sulfanyl}-4-(tetrahydro-2H-pyran-2-yl)-pyridine-3,5-dicarbonitrile

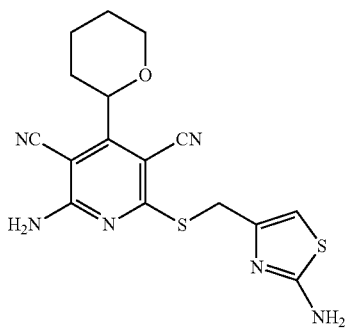

50 mg (0.14 mmol) of the compound from Example 31A, 39 mg (0.21 mmol) of 4-(chloromethyl)-1,3-thiazol-2-amine and 48 mg (0.58 mmol) of sodium bicarbonate in 2.0 ml of dry DMF are reacted analogously to the preparation of the compound of Example 14.

Yield: 35 mg (49% of theory)

¹H-NMR (400 MHz, DMSO-$d_6$): δ=8.20-7.79 (br. s, 2H), 7.08-6.93 (br. s, 2H), 6.60 (s, 1H), 4.59-4.49 (m, 1H), 4.27 (s, 2H), 4.02 (dd, 1H), 2.55-2.46 (m, 1H), 1.96-1.85 (m, 1H), 1.74-1.65 (m, 2H), 1.65-1.51 (m, 3H).

LC-MS (Method 5): $R_t$=2.31 min; MS (ESIpos): m/z=373 [M+H]⁺.

Example 69

Methyl 3-{[(6-amino-3,5-dicyano-4-cyclohexylpyridin-2-yl)sulfanyl]methyl}benzoate

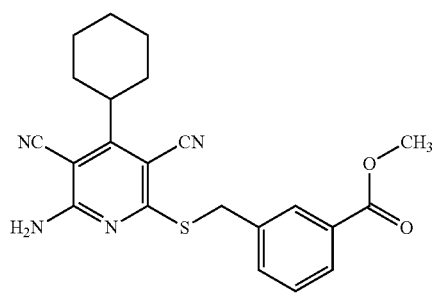

140 mg (0.54 mmol) of the compound from Example 33A, 137 mg (0.60 mmol) of methyl 3-(bromomethyl)benzoate and 182 mg (2.17 mmol) of sodium bicarbonate in 2.0 ml of dry DMF are reacted analogously to the preparation of the compound of Example 29.

Yield: 30 mg (14% of theory)

¹H-NMR (400 MHz, DMSO-$d_6$): δ=8.23-7.78 (br. s, 2H), 8.07 (s, 1H), 7.83 (d, 2H), 7.47 (t, 1H), 4.53 (s, 2H), 3.87 (s, 3H), 2.93-2.82 (m, 1H), 2.02-1.89 (m, 2H), 1.89-1.80 (m, 2H), 1.76-1.65 (m, 3H), 1.39-1.13 (m, 3H).

LC-MS (Method 7): $R_t$=4.05 min; MS (ESIpos): m/z=407 [M+H]⁺.

The compounds listed in the table below are prepared analogously to Example 69 from the appropriate starting materials:

| Example No. | Structure (yield) | LC-MS: $R_t$ [min] (Method); MS (ESI): m/z [M + H]⁺ | ¹H-NMR (DMSO-$d_6$): δ = |
|---|---|---|---|
| 70 | 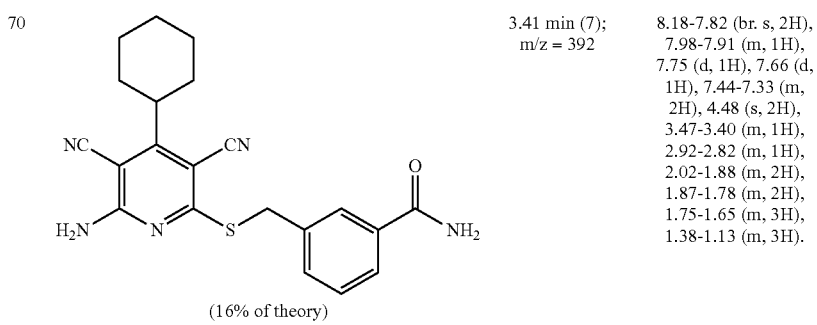 (16% of theory) | 3.41 min (7); m/z = 392 | 8.18-7.82 (br. s, 2H), 7.98-7.91 (m, 1H), 7.75 (d, 1H), 7.66 (d, 1H), 7.44-7.33 (m, 2H), 4.48 (s, 2H), 3.47-3.40 (m, 1H), 2.92-2.82 (m, 1H), 2.02-1.88 (m, 2H), 1.87-1.78 (m, 2H), 1.75-1.65 (m, 3H), 1.38-1.13 (m, 3H). |

-continued
| Example No. | Structure (yield) | LC-MS: $R_t$ [min] (Method); MS (ESI): m/z [M + H]⁺ | ¹H-NMR (DMSO-d₆): δ = |
|---|---|---|---|
| 71 | 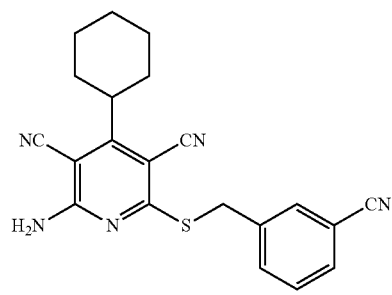<br>(26% of theory) | 4.10 min (5); m/z = 373 | 8.46-7.63 (br. s, 2H), 8.06 (s, 1H), 7.86 (d, 1H), 7.71 (d, 1H), 7.51 (t, 1H), 4.45 (s, 2H), 2.91-2.81 (m, 1H), 1.99-1.77 (m, 4H), 1.76-1.63 (m, 3H), 1.37-1.12 (m, 3H). |
| 72 | 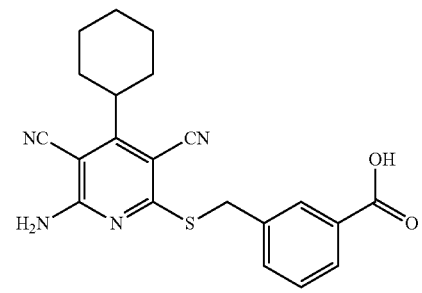<br>(16% of theory) | 2.69 min (4); m/z = 393 | 13.15-12.82 (br. s, 1H), 8.17-7.71 (br. s, 2H), 8.02 (s, 1H), 7.81 (d, 1H), 7.75 (d, 1H), 7.41 (t, 1H), 4.52 (s, 2H), 2.92-2.81 (m, 1H), 2.01-1.88 (m, 2H), 1.88-1.78 (m, 2H), 1.76-1.65 (m, 3H), 1.37-1.13 (m, 3H). |
| 73 | 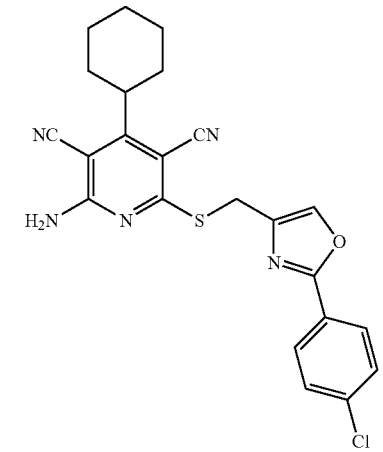<br>(68% of theory) | 2.86 min (22); m/z = 450 | 8.33 (s, 1H), 8.28-7.72 (br. s, 2H), 7.97 (d, 2H), 7.60 (d, 2H), 4.47 (s, 2H), 2.94-2.83 (m, 1H), 2.01-1.89 (m, 2H), 1.89-1.79 (m, 2H), 1.77-1.66 (m, 3H), 1.38-1.12 (m, 3H). |

| Example No. | Structure (yield) | LC-MS: $R_t$ [min] (Method); MS (ESI): m/z [M + H]$^+$ | $^1$H-NMR (DMSO-$d_6$): δ = |
|---|---|---|---|
| 74 | 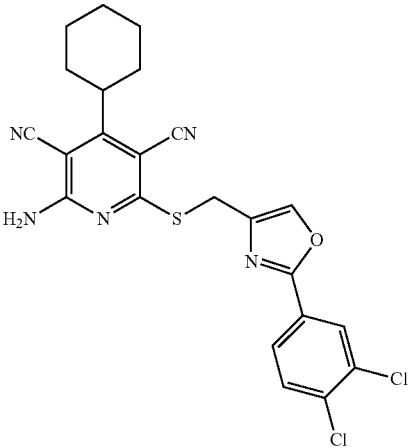<br>(31% of theory) | 3.40 min (4); m/z = 484 | 8.48 (s, 1H), 8.24-7.86 (br. s, 2H), 8.10 (s, 1H), 7.91 (d, 1H), 7.79 (d, 1H), 4.37 (s, 2H), 2.92-2.82 (m, 1H), 2.01-1.87 (m, 2H), 1.87-1.79 (m, 2H), 1.75-1.63 (m, 3H), 1.37-1.13 (m, 3H). |
| 75 | 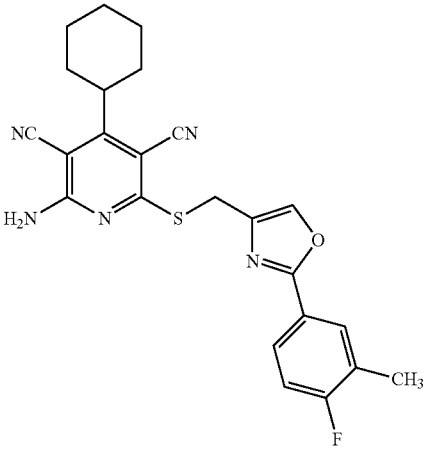<br>(20% of theory) | 3.23 min (4); m/z = 448 | 8.29 (s, 1H), 8.21-7.85 (br. s, 2H), 7.90 (d, 1H), 7.83-7.76 (m, 1H), 7.29 (t, 1H), 4.35 (s, 2H), 2.92-2.82 (m, 1H), 2.30 (s, 3H), 2.00-1.88 (m, 2H), 1.88-1.79 (m, 2H), 1.75-1.65 (m, 3H), 1.37-1.15 (m, 3H). |
| 76 | 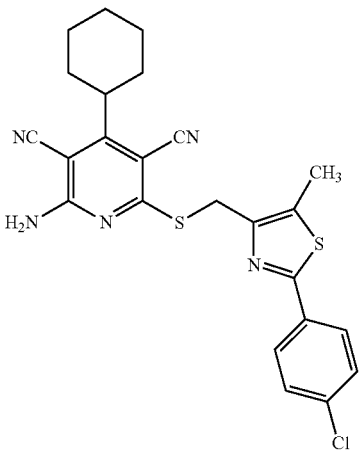<br>(39% of theory) | 3.44 min (4); m/z = 481 | 8.10-7.83 (br. s, 2H), 7.87 (d, 2H), 7.55 (d, 2H), 4.63 (s, 2H), 2.95-2.85 (m, 1H), 2.55 (s, 3H), 2.03-1.90 (m, 2H), 1.89-1.81 (m, 2H), 1.77-1.68 (m, 3H), 1.39-1.13 (m, 3H). |

| Example No. | Structure (yield) | LC-MS: $R_t$ [min] (Method); MS (ESI): m/z [M + H]⁺ | ¹H-NMR (DMSO-d₆): δ = |
|---|---|---|---|
| 77 | 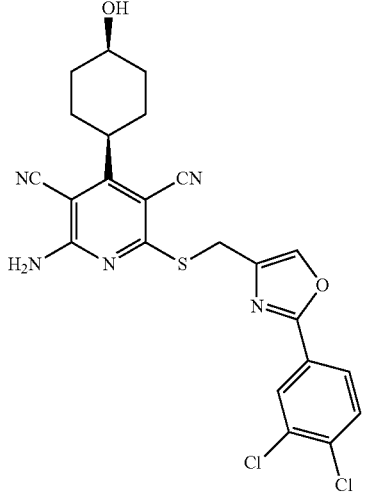<br>(80% of theory) | 2.80 min (4);<br>m/z = 500 | 8.39 (s, 1H), 8.25-7.86 (br. s, 2H), 8.10 (s, 1H), 7.91 (d, 1H), 7.79 (d, 1H), 4.70 (d, 1H), 4.37 (s, 2H), 3.47-3.37 (m, 1H), 2.84-2.73 (m, 1H), 2.07-1.92 (m, 4H), 1.76-1.66 (m, 2H), 1.27-1.15 (m, 2H). |
| 78 | 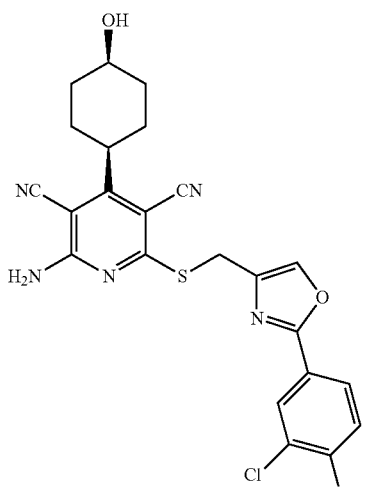<br>(71% of theory) | 2.65 min (4);<br>m/z = 484 | 8.36 (s, 1H), 8.21-7.84 (br. s, 2H), 8.08 (d, 1H), 7.98-7.93 (m, 1H), 7.59 (t, 1H), 4.69 (d, 1H), 4.37 (s, 2H), 3.47-3.37 (m, 1H), 2.84-2.75 (m, 1H), 2.07-1.92 (m, 4H), 1.76-1.67 (m, 2H), 1.28-1.15 (m, 2H). |
| 79 | 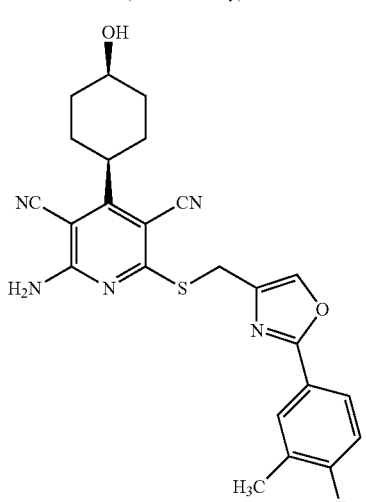<br>(75% of theory) | 2.58 min (4);<br>m/z = 464 | 8.30 (s, 1H), 8.19-7.75 (br. s, 2H), 7.91 (d, 1H), 7.83-7.77 (m, 1H), 7.29 (t, 1H), 4.70 (d, 1H), 4.36 (s, 2H), 3.47-3.36 (m, 1H), 2.84-2.75 (m, 1H), 2.31 (s, 3H), 2.08-1.92 (m, 4H), 1.75-1.67 (m, 2H), 1.28-1.15 (m, 2H). |

Example 80 rac-2-Amino-4-(tetrahydro-2H-pyran-2-yl)-6-{[3-(1H-tetrazol-5-yl)benzyl]sulfanyl}pyridine-3,5-dicarbonitrile

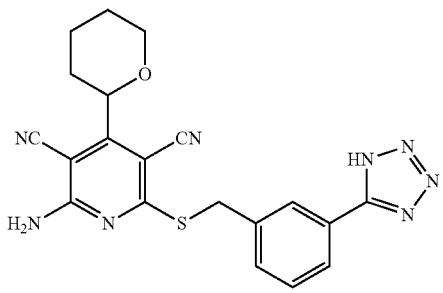

55 mg (0.16 mmol) of the compound from Example 31A, 65 mg (0.18 mmol) of the compound from Example 50A and 41 mg (0.49 mmol) of sodium bicarbonate are suspended in 1.7 ml of dry DMF and stirred at RT for 10 h. The mixture is then poured into 2 ml of water and adjusted to pH 4 by addition of a little 1 N hydrochloric acid. A brown precipitate is formed, which is filtered off and purified further by preparative HPLC (column: YMC GEL ODS-AQ S-5, 15 µm; mobile phase gradient: acetonitrile/water 10:90→95:5).

Yield: 5 mg (7% of theory)

$^1$H-NMR (400 MHz, DMSO-$d_6$): δ=16.96-16.76 (br. s, 1H), 8.18-7.86 (br. s, 2H), 8.14 (s, 1H), 7.92 (d, 1H), 7.75 (d, 1H), 7.54 (t, 1H), 4.56 (s, 2H), 4.56-4.49 (m, 1H), 4.01 (d, 1H), 3.58-3.47 (m, 1H), 1.96-1.87 (m, 1H), 1.75-1.51 (m, 5H).

LC-MS (Method 4): $R_t$=2.50 min; MS (ESIpos): m/z=419 $[M+H]^+$.

B. Assessing the Pharmacological and Physiological Activity

The pharmacological and physiological activity of the compounds according to the invention can be demonstrated in the following assays:

B-1. Indirect Determination of the Adenosine Agonism by Way of Gene Expression

Cells of the CHO (Chinese Hamster Ovary) permanent cell line are transfected stably with the cDNA for the adenosine receptor subtypes A1, A2a and A2b. The adenosine A1 receptors are coupled to the adenylate cyclase by way of $G_i$ proteins, while the adenosine A2a and A2b receptors are coupled by way of $G_s$ proteins. In correspondence with this, the formation of cAMP in the cell is inhibited or stimulated, respectively. After that, expression of the luciferase is modulated by way of a cAMP-dependent promoter. The luciferase test is optimized, with the aim of high sensitivity and reproducibility, low variance and good suitability for implementation on a robot system, by varying several test parameters, such as cell density, duration of the growth phase and the test incubation, forskolin concentration and medium composition. The following test protocol is used for pharmacologically characterizing cells and for the robot-assisted substance screening:

The stock cultures are grown, at 37° C. and under 5% $CO_2$, in DMEM/F12 medium containing 10% FCS (fetal calf serum) and in each case split 1:10 after 2-3 days. The test cultures are seeded in 384-well plates with 2000 cells per well and grown at 37° C. for approx. 48 hours. The medium is then replaced with a physiological sodium chloride solution (130 mM sodium chloride, 5 mM potassium chloride, 2 mM calcium chloride, 20 mM HEPES, 1 mM magnesium chloride hexahydrate, 5 mM sodium bicarbonate, pH 7.4). The substances to be tested, which are dissolved in DMSO, are pipetted into the test cultures (maximum final concentration of DMSO in the test mixture: 0.5%) in a dilution series of from $5\times10^{-11}$M to $3\times10^{-6}$M (final concentration). 10 minutes later, forskolin is added to the A1 cells and all the cultures are subsequently incubated at 37° C. for four hours. After that, 35 µl of a solution which is composed of 50% lysis reagent (30 mM disodium hydrogenphosphate, 10% glycerol, 3% TritonX100, 25 mM TrisHCl, 2 mM dithiothreitol (DTT), pH 7.8) and 50% luciferase substrate solution (2.5 mM ATP, 0.5 mM luciferin, 0.1 mM coenzyme A, 10 mM tricine, 1.35 mM magnesium sulfate, 15 mM DTT, pH 7.8) are added to the test cultures, which are shaken for approx. 1 minute and the luciferase activity is measured using a camera system. The $EC_{50}$ values are determined, i.e., the concentrations at which 50% of the luciferase answer is inhibited in the case of the A1 cell, and, respectively, 50% of the maximum stimulation with the corresponding substance is achieved in the case of the A2b and A2a cells. The adenosine-analogous compound NECA (5-N-ethylcarboxamidoadenosine), which binds to all adenosine receptor subtypes with high affinity and possesses an agonistic effect, is used in these experiments as the reference compound [Klotz, K. N., Hessling, J., Hegler, J., Owman, C., Kull, B., Fredholm, B. B., Lohse, M. J., "Comparative pharmacology of human adenosine receptor subtypes—characterization of stably transfected receptors in CHO cells", *Naunyn Schmiedebergs Arch. Pharmacol.*, 357 (1998), 1-9].

Table 1 below lists the $EC_{50}$ values of representative working examples for the receptor stimulation on adenosine A1, A2a and A2b receptor subtypes:

TABLE 1

| Example No. | $EC_{50}$ A1 [nM] (1 µM forskolin) | $EC_{50}$ A2a [nM] | $EC_{50}$ A2b [nM] |
|---|---|---|---|
| 3 | 0.8 | 1260 | 558 |
| 4 | 2.9 | 1100 | 320 |
| 9 | 8.9 | >3000 | 791 |
| 15 | 10 | 380 | 670 |
| 23 | 0.4 | 620 | 75 |
| 29 | 3.8 | >3000 | 345 |
| 35 | 68 | 1470 | >3000 |
| 51 | 6.8 | >3000 | >3000 |
| 56 | 0.8 | >3000 | 51 |
| 58 | 11 | >3000 | 950 |
| 62 | 0.06 | >3000 | >3000 |
| 65 | 9.5 | >3000 | 860 |
| 70 | 0.08 | 224 | 22 |
| 76 | 106 | >3000 | >3000 |
| 78 | 17 | >3000 | >3000 |

B-2. Studies on Isolated Blood Vessels

The caudal artery of anesthetized rats is excised and mounted in a conventional apparatus for measuring isolated blood vessels. The vessels are perfused in a heated bath and contracted using phenylephrine. The extent of the contraction is determined using a contraction meter. Test substances are added to the precontracted blood vessels, and the reduction of the contraction of the vessels is measured. A reduction of contraction corresponds to a dilation of the vessels. The concentration at which the contraction of the blood vessels is reduced by 50% is given as the $EC_{50}$ value of a test substance with respect to its relaxing properties.

B-3. Measurement of Blood Pressure and Heart Rate on Awake Rats

Various dosages of test substances are administered orally to awake SHR rats (spontaneously hypertensive rats) carrying an internal transmitter capable of measuring permanently both blood pressure and heart rate (telemetric monitoring of hemodynamic parameters. Blood pressure, heart rate and their changes are then recorded over a period of 24 hours.

B-4. Measurement of Blood Pressure and Heart Rate on Awake Marmosets

Various concentrations of the test substances are administered orally to awake marmosets which carry an internal transmitter capable of measuring permanently both blood pressure and heart rate (telemetric monitoring of hemodynamic parameters). Blood pressure, heart rate and their changes are then recorded for a period of 6-24 hours.

B-5. Determination of the Solubility

Reagents Required:

PBS buffer pH 7.4: weigh 90.00 g of NaCl p.a. (for example from Merck, Art. No. 1.06404.1000), 13.61 g of $KH_2PO_4$ p.a. (for example from Merck, Art. No. 1.04873.1000) and 83.35 g of 1 N aqueous sodium hydroxide solution (for example from Bernd Kraft GmbH, Art. No. 01030.4000) into a 1 liter graduated flask, make up to the mark with water and stir for about 1 hour;

acetate buffer pH 4.6: weigh 5.4 g of sodium acetate× $3H_2O$, analytical grade (e.g. from Merck, Cat. No. 1.06267.0500) into a 100 ml graduated flask, dissolve in 50 ml of water, add 2.4 g of glacial acetic acid, make up to 100 ml with water, check the pH and adjust to pH 4.6 if necessary;

dimethyl sulfoxide (for example from Baker, Art. No. 7157.2500);

distilled water.

Preparation of the Calibration Solutions

Preparation of the starting solution for calibration solutions (stock solution): About 0.5 mg of the test substance is weighed accurately into a 2 ml Eppendorf safe-lock tube (from Eppendorf, Cat. No. 0030 120.094), DMSO is added to a concentration of 600 µg/ml (e.g. 0.5 mg of substance+833 µl of DMSO), and the mixture is agitated with a vortexer until dissolution is complete.

Calibration solution 1 (20 µg/ml): 34.4 µl of the stock solution are mixed with 1000 µl of DMSO and homogenized.

Calibration solution 2 (2.5 µg/ml): 100 µl of calibration solution 1 are mixed with 700 µl of DMSO and homogenized.

Preparation of the Sample Solutions:

Sample solution for solubility up to 10 g/l in PBS buffer pH 7.4: About 5 mg of the test substance are weighed accurately into a 2 ml Eppendorf safe-lock tube (from Eppendorf, Cat. No. 0030 120.094), and PBS buffer pH 7.4 is added to a concentration of 5 g/l (e.g. 5 mg of substance+500 µl of PBS buffer pH 7.4).

Sample solution for solubility up to 10 g/l in acetate buffer pH4.6: About 5 mg of the test substance are weighed accurately into a 2 ml Eppendorf safe-lock tube (from Eppendorf, Cat. No. 0030 120.094), and acetate buffer pH 4.6 is added to a concentration of 5 g/l (e.g. 5 mg of substance+500 µl of acetate buffer pH 4.6).

Sample solution for solubility up to 10 g/l in water: About 5 mg of the test substance are weighed accurately into a 2 ml Eppendorf safe-lock tube (from Eppendorf, Cat. No. 0030 120.094), and water is added to a concentration of 5 g/l (e.g. 5 mg of substance+500 µl of water).

Procedure:

The sample solutions prepared in this way are shaken at 1400 rpm using a controlled-temperature shaker (e.g. Eppendorf thermomixer comfort Cat. No. 5355 000.011 with exchangeable block Cat. No. 5362.000.019) at 20° C. for 24 hours. 180 µl are removed from each of the solutions and transferred into Beckman polyallomer centrifuge tubes (Cat. No. 343621). These solutions are centrifuged at about 223 000×g for 1 hour (e.g. Beckman Optima L-90K ultracentrifuge with type 42.2 Ti rotor at 42 000 rpm). 100 µl of the supernatant are removed from each sample solution and diluted 1:5, 1:100 and 1:1000 with the solvent used in each case (water, PBS buffer 7.4 or acetate buffer pH 4.6). A portion of each dilution is dispensed into a suitable vessel for HPLC analysis.

Analysis:

The samples are analyzed by RP-HPLC. A two-point calibration plot of the test compound in DMSO is used for quantification. The solubility is expressed in mg/l. Analysis sequence: 1) calibration solution 2.5 mg/ml; 2) calibration solution 20 µg/ml; 3) sample solution 1:5; 4) sample solution 1:100; 5) sample solution 1:1000.

HPLC Method for Acids:

Agilent 1100 with DAD (G1315A), quat. pump (G1311A), autosampler CTC HTS PAL, degasser (G1322A) and column thermostat (G1316A); column: Phenomenex Gemini C18, 50 mm×2 mm, 5µ; temperature: 40° C.; eluent A: water/phosphoric acid pH 2; eluent B: acetonitrile; flow rate: 0.7 ml/min; gradient: 0-0.5 min 85% A, 15% B; ramp: 0.5-3 min 10% A, 90% B; 3-3.5 min 10% A, 90% B; ramp: 3.5-4 min 85% A, 15% B; 4-5 min 85% A, 15% B.

HPLC Method for Bases:

Agilent 1100 with DAD (G1315A), quat. pump (G1311A), autosampler CTC HTS PAL, degasser (G1322A) and column thermostat (G1316A); column: VDSoptilab Kromasil 100 C18, 60 mm×2.1 mm, 3.5µ; temperature: 30° C.; eluent A: water+5 ml perchloric acid/l; eluent B: acetonitrile; flow rate: 0.75 ml/min; gradient: 0-0.5 min 98% A, 2% B; ramp: 0.5-4.5 min 10% A, 90% B; 4.5-6 min 10% A, 90% B; ramp: 6.5-6.7 min 98% A, 2% B; 6.7-7.5 min 98% A, 2% B.

B-6. Determination of Pharmacokinetic Parameters After Intravenous and Oral Administration The substance to be tested is administered intravenously as a solution to animals (for example mice, rats, dogs), and oral administration takes place as solution or suspension by gavage. After administration of the substance, blood is taken from the animals at fixed times and is heparinized, and then plasma is obtained therefrom by centrifugation. The substance is quantified analytically in the plasma by LC/MS-MS. The plasma concentration/time courses found in this way are used to calculate the pharmacokinetic parameters such as AUC, $C_{max}$, $T_{1/2}$ (half-life) and CL (clearance) by means of a validated pharmacokinetic computer program.

C. Working Examples of Pharmaceutical Compositions

The compounds of the invention can be converted into pharmaceutical preparations in the following ways:

Tablet:

Composition:

100 mg of the compound of the invention, 50 mg of lactose (monohydrate), 50 mg of maize starch (native), 10 mg of polyvinylpyrrolidone (PVP 25) (from BASF, Ludwigshafen, Germany) and 2 mg of magnesium stearate.

Tablet weight 212 mg, diameter 8 mm, radius of curvature 12 mm.

Production:

The mixture of compound of the invention, lactose and starch is granulated with a 5% strength solution (mi/m) of the PVP in water. The granules are dried and mixed with the magnesium stearate for 5 minutes. This mixture is compressed in a conventional tablet press (see above for format of the tablet). A guideline compressive force for the compression is 15 kN.

Suspension which can be Administered Orally:

Composition:

1000 mg of the compound of the invention, 1000 mg of ethanol (96%), 400 mg of Rhodigel® (xanthan gum from FMC, Pennsylvania, USA) and 99 g of water.

10 ml of oral suspension correspond to a single dose of 100 mg of the compound of the invention.

Production:

The Rhodigel is suspended in ethanol, and the compound of the invention is added to the suspension. The water is added while stirring. The mixture is stirred for about 6 h until the swelling of the Rhodigel is complete.

Solution which can be Administered Orally:

Composition:

500 mg of the compound of the invention, 2.5 g of polysorbate and 97 g of polyethylene glycol 400. 20 g of oral solution correspond to a single dose of 100 mg of the compound of the invention.

Production:

The compound of the invention is suspended in the mixture of polyethylene glycol and polysorbate with stirring. The stirring process is continued until the compound of the invention has completely dissolved.

i.v. Solution:

The compound of the invention is dissolved in a concentration below the saturation solubility in a physiologically tolerated solvent (e.g. isotonic saline, 5% glucose solution and/or 30% PEG 400 solution). The solution is sterilized by filtration and used to fill sterile and pyrogen-free injection containers.

The invention claimed is:

1. A compound of the formula (I)

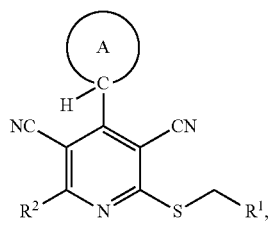

(I)

in which ring A represents a $(C_4-C_7)$-cycloalkyl or $(C_4-C_7)$-cycloalkenyl ring or represents a 4- to 7-membered heterocycle which is attached via carbon and which contains one or two ring members from the group consisting of N—$R^3$ and O, where $(C_4-C_7)$-cycloalkyl and $(C_4-C_7)$-cycloalkenyl may be mono- or disubstituted by identical or different radicals selected from the group consisting of $(C_1-C_6)$-alkyl, hydroxyl, $(C_1-C_6)$-alkoxy, amino, mono-$(C_1-C_6)$-alkylamino and di-$(C_1-C_6)$-alkylamino, where the $(C_1-C_6)$-alkyl and $(C_1-C_6)$-alkoxy radicals mentioned for their part may be mono- or disubstituted by identical or different radicals from the group consisting of hydroxyl, $(C_1-C_4)$-alkoxy and $(C_3-C_6)$-cyclo-alkyl, and where $R^3$ represents hydrogen, $(C_1-C_6)$-alkyl which may be mono- or disubstituted by identical or different radicals from the group consisting of hydroxyl, $(C_1-C_4)$-alkoxy, $(C_1-C_4)$-acyloxy and $(C_3-C_6)$-cycloalkyl, or $(C_1-C_6)$-acyl which may be substituted by hydroxyl or $(C_1-C_4)$-alkoxy, $R^1$ represents a $(C_6-C_{10})$-aryl or 5- to 10-membered heteroaryl having up to three ring heteroatoms from the group consisting of N, O and S, each of which radicals (i) is mono- or disubstituted by identical or different radicals selected from the group consisting of halogen, nitro, cyano, $(C_1-C_6)$-alkyl, trifluoromethyl, hydroxyl, $(C_1-C_6)$-alkoxy, amino, mono-$(C_1-C_6)$-alkylamino, di-$(C_1-C_6)$-alkylamino, carboxyl, $(C_1-C_6)$-alkoxycarbonyl, carbamoyl, mono-$(C_1-C_6)$-alkylaminocarbonyl and di-$(C_1-C_6)$-alkylamino-carbonyl and/or (ii) is substituted by pyrrolidino, piperidino, morpholino, piperazino, N'—$(C_1-C_4)$-alkylpiperazino, tetrazolyl or a group of the formula -L-$R^4$ in which L represents a bond, NH or O and $R^4$ represents phenyl or 5- or 6-membered heteroaryl having up to three ring heteroatoms from the group consisting of N, O and S, each of which radicals may be mono- to trisubstituted by identical or different radicals selected from the group consisting of halogen, nitro, cyano, $(C_1-C_6)$-alkyl, trifluoromethyl, hydroxyl, $(C_1-C_6)$-alkoxy, difluoromethoxy, trifluoromethoxy, amino, mono-$(C_1-C_6)$-alkylamino, di-$(C_1-C_6)$-alkylamino, $(C_1-C_6)$-alkoxycarbonyl and carboxyl, and $R^2$ represents hydrogen or represents $(C_1-C_6)$-alkyl or $(C_1-C_6)$-alkoxy, each of which radicals may be substituted by hydroxyl, $(C_1-C_4)$-alkoxy, carboxyl, $(C_1-C_4)$-alkoxycarbonyl or up to three times by fluorine or $R^2$ represents a group of the formula —$NR^5R^6$ in which $R^5$ and $R^6$ are identical or different and independently of one another represent hydrogen or $(C_1-C_6)$-alkyl which may be mono- or disubstituted by identical or different radicals from the group consisting of hydroxyl, $(C_1-C_4)$-alkoxy, amino, mono-$(C_1-C_4)$-alkylamino, di-$(C_1-C_4)$-alkylamino, carboxyl, $(C_1-C_4)$-alkoxycarbonyl and a 4- to 7-membered heterocycle, where the heterocycle mentioned contains one or two ring heteroatoms from the group consisting of N, O and S and for its part may be mono- or disubstituted by identical or different radicals from the group consisting of $(C_1-C_4)$-alkyl, hydroxyl, oxo and $(C_1-C_4)$-alkoxy, or $R^5$ and $R^6$ together with the nitrogen atom, to which they are attached, form a 4- to 7-membered heterocycle which may contain a further ring heteroatom from the group consisting of N, O or S and may be mono- or disubstituted by identical or different radicals from the group consisting of $(C_1-C_4)$-alkyl, hydroxyl, oxo, $(C_1-C_4)$-alkoxy, azetidino, pyrrolidino, piperidino and morpholino, and N-oxides, physiologically acceptable salts, and physiologically acceptable salts of the N-oxides thereof.

2. The compound of the formula (I) as claimed in claim 1 in which
$R^1$ represents phenyl or a 5- or 6-membered heteroaryl having up to three ring heteroatoms from the group consisting of N, O and S, each of which radicals
  (i) is mono- or disubstituted by identical or different radicals selected from the group consisting of halogen, nitro, cyano, $(C_1-C_6)$-alkyl, trifluoromethyl, hydroxyl, $(C_1-C_6)$-alkoxy, amino, mono-$(C_1-C_6)$-alkylamino, di-$(C_1-C_6)$-alkylamino, carboxyl, $(C_1-C_6)$-alkoxycarbonyl, carbamoyl, mono-$(C_1-C_6)$-alkylaminocarbonyl and di-$(C_1-C_6)$-alkylamino-carbonyl
  and/or
  (ii) is substituted by pyrrolidino, piperidino, morpholino, piperazino, N'—$(C_1-C_4)$-alkylpiperazino, tetrazolyl or a group of the formula -L-$R^4$ in which
    L represents a bond, NH or O
    and
    $R^4$ represents phenyl or a 5- or 6-membered heteroaryl having up to three ring heteroatoms from the group consisting of N, O and S, each of which radicals may be mono- to trisubstituted by identical or different radicals selected from the group consisting of halogen, nitro, cyano, $(C_1-C_6)$-alkyl, trifluoromethyl, hydroxyl, $(C_1-C_6)$-alkoxy, difluoromethoxy, trifluoromethoxy, amino, mono-$(C_1-C_6)$-alkylamino, di-$(C_1-C_6)$-alkylamino, $(C_1-C_6)$-alkoxycarbonyl and carboxyl,
or
$R^1$ represents N-oxidopyridyl.

3. The compound of the formula (I) of claim 1 in which ring A represents cyclopentyl, cyclohexyl, cyclopent-2-en-1-yl, cyclopent-3-en-1-yl, cyclohex-2-en-1-yl or cyclohex-3-en-1-yl, represents a 5- or 6-membered heterocycle which is attached via carbon and which contains a ring member from the group consisting of N—$R^3$ and O, or represents a heterocycle of the formula

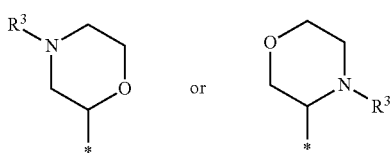

which is attached via carbon and in which
cyclopentyl, cyclohexyl, cyclopentenyl and cyclohexenyl may be mono- or disubstituted by identical or different radicals selected from the group consisting of $(C_1-C_4)$-alkyl, hydroxyl, $(C_1-C_4)$-alkoxy, amino, mono-$(C_1-C_4)$-alkylamino and di-$(C_1-C_4)$-alkylamino, where the $(C_1-C_4)$-alkyl- and $(C_1-C_4)$-alkoxy radicals mentioned for their part may be mono- or disubstituted by identical or different radicals from the group consisting of hydroxyl, $(C_1-C_4)$-alkoxy and $(C_3-C_5)$-cycloalkyl,
* denotes the point of attachment to the pyridine ring
and
$R^3$ represents hydrogen, $(C_1-C_4)$-alkyl which may be mono- or disubstituted by identical or different radicals from the group consisting of hydroxyl, $(C_1-C_4)$-alkoxy, $(C_1-C_4)$-acyloxy and $(C_3-C_5)$-cycloalkyl, or $(C_1-C_4)$-acyl which may be substituted by hydroxyl or $(C_1-C_4)$-alkoxy,
$R^1$ represents a phenyl or 5- or 6-membered heteroaryl having up to three ring heteroatoms from the group consisting of N, O and S, each of which radicals
  (i) is mono- or disubstituted by identical or different radicals selected from the group consisting of fluorine, chlorine, cyano, $(C_1-C_4)$-alkyl, amino, mono-$(C_1-C_4)$-alkylamino, di-$(C_1-C_4)$-alkylamino, $(C_1-C_4)$-alkoxycarbonyl, carboxyl and carbamoyl
  and/or
  (ii) is substituted by morpholino, N'—$(C_1-C_4)$-alkylpiperazino or a group of the formula -L-$R^4$ in which
    L represents a bond or NH
    and
    $R^4$ represents phenyl or 5- or 6-membered heteroaryl having up to three ring heteroatoms from the group consisting of N, O and S, each of which radicals may be mono- to trisubstituted by identical of different radicals selected from the group consisting of fluorine, chlorine, cyano, $(C_1-C_4)$-alkyl, trifluoromethyl, $(C_1-C_4)$-alkoxy, trifluoromethoxy, $(C_1-C_4)$-alkoxycarbonyl and carboxyl,
or
$R^1$ represents N-oxidopyridyl,
and
$R^2$ represents hydrogen or represents $(C_1-C_4)$-alkoxy which may be substituted up to three times by fluorine
or
$R^2$ represents a group of the formula —$NR^5R^6$ in which
  $R^5$ represents hydrogen or $(C_1-C_4)$-alkyl which may be substituted by hydroxyl, $(C_1-C_4)$-alkoxy, amino, mono-$(C_1-C_4)$-alkylamino, di-$(C_1-C_4)$-alkylamino, carboxyl, $(C_1-C_4)$-alkoxycarbonyl or a 5- or 6-membered heterocycle,
  where the heterocycle mentioned contains one or two ring heteroatoms from the group consisting of N and O and for its part may be mono- or disubstituted by identical or different radicals from the group consisting of methyl, ethyl, hydroxyl, methoxy and ethoxy, and
  $R^6$ represents hydrogen or methyl
or
  $R^5$ and $R^6$ together with the nitrogen atom, to which they are attached form a 5- or 6-membered heterocycle which may contain a further ring heteroatom from the group consisting of N or O and may be mono- or disubstituted by identical or different radicals from the group consisting of methyl, ethyl, hydroxyl, methoxy and ethoxy.

4. The compound of the formula (I) of claim 1 in which ring A represents a group of the formula

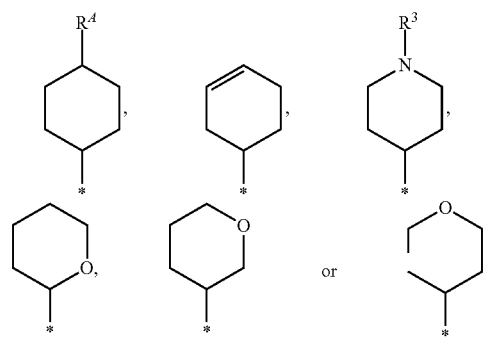

in which
* denotes the point of attachment to the pyridine ring,
$R^4$ represents hydrogen, hydroxyl, methoxy, ethoxy or 2-hydroxyethoxy
and $R^3$ represents methyl, ethyl, 2-hydroxyethyl, 2-acetoxyethyl, 3-hydroxypropyl, 3-acetoxypropyl or hydroxyacetyl, $R^1$ represents phenyl, oxazolyl, thiazolyl or pyridyl, each of which radicals
- (i) is mono- or disubstituted by identical or different radicals selected from the group consisting of fluorine, chlorine, methyl, amino, methoxycarbonyl, ethoxycarbonyl, carboxyl and carbamoyl or
- (ii) is substituted by a group of the formula -L-$R^4$ in which
    L represents a bond or NH
    and
    $R^4$ represents phenyl or pyridyl, each of which radicals may be mono- or disubstituted by identical or different radicals selected from the group consisting of fluorine, chlorine, cyano, methyl, methoxy and carboxyl, and $R^2$ represents hydrogen, methoxy or a group of the formula —$NR^5R^6$ in which
    $R^5$ represents hydrogen or $(C_1-C_4)$-alkyl which may be substituted by hydroxyl, amino, methylamino, ethylamino, dimethylamino, diethylamino or a heterocycle of the formula

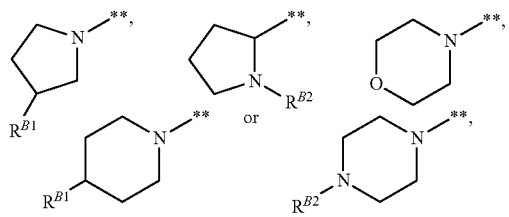

and $R^6$ represents hydrogen or $R^5$ and $R^6$ together with the nitrogen atom to which they are attached form a group of the formula

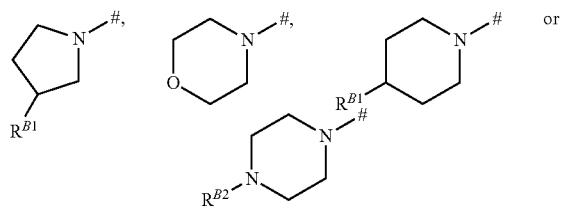

in which in each case
** denotes the point of attachment to the $(C_1-C_4)$-alkyl radical,
\# denotes the point of attachment to the pyridine ring,
$R^{B1}$ represents hydrogen or hydroxyl
and
$R^{B2}$ represents hydrogen or methyl.

5. A process for preparing a compound of the formula (I) of claim 1 in which $R^2$ represents $NH_2$, wherein a compound of the formula (II)

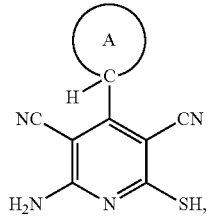

in which ring A has the meaning given in claim 1,
is reacted in an inert solvent in the presence of a base with a compound of the formula (III)

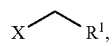

in which $R^1$ has the meaning given in claim 1 and
X represents a suitable leaving group, such as halogen, mesylate, tosylate or triflate, to give a compound of the formula (I-A)

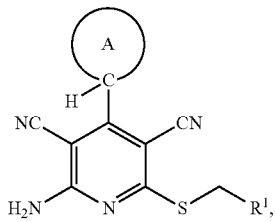

in which $R^1$ and ring A have the meanings given above,
and the compounds of the formula (I-A) are, if appropriate, converted with the appropriate (i) solvents and/or (ii) bases or acids into their physiologically acceptable salts.

6. A process for preparing the compounds of the formula (I) as defined in claim 1 in which $R^2$ represents the group —$NR^5R^6$ and in which at least one of the two radicals $R^5$ and $R^6$ is not hydrogen, characterized in that compounds of the formula (I-A) are initially converted with copper(II) chloride and isoamyl nitrite in a suitable solvent into compounds of the formula (VI)

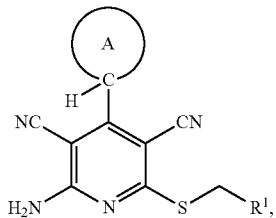

in which $R^1$ and ring A have the meanings given in claim 1,

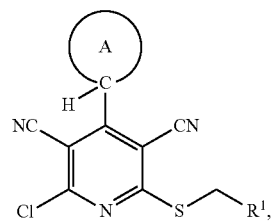

in which $R^1$ and the ring A have the meanings given above, and these are then reacted with a compound of the formula (VII)

(VII)

in which
$R^{5A}$ has the meaning of $R^5$ given in claim 1,
$R^{6A}$ has the meaning of $R^6$ given in claim 1,
but at least one of the two radicals $R^{5A}$ and $R^{6A}$ does not represent hydrogen,
to give compounds of the formula (I-B)

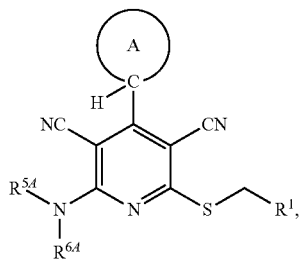
(I-B)

in which $R^1$, $R^{5A}$, $R^{6A}$ and ring A each have the meanings given above,
and the compounds of the formula (I-B) are, if appropriate, converted with the appropriate (i) solvents and/or (ii) bases or acids into their physiologically acceptable salts.

7. A pharmaceutical composition comprising a compound of the formula (I) as defined in claim 1 in combination with an inert nontoxic pharmaceutically suitable auxiliary.

8. The pharmaceutical composition of claim 7, further comprising one or more further active compounds selected from the group consisting of lipid metabolism-modifying active compounds, antidiabetics, antihypertensive drugs and antithrombotic drugs.

9. A method for the treatment or prevention of hypertension, coronary heart disease, acute coronary syndrome, angina pectoris, heart failure, myocardial infarction and atrial fibrillation in humans and animals using an effective amount of at least one compound of the formula (I) of claim 1.

10. A method for the treatment or prevention of hypertension, coronary heart disease, acute coronary syndrome, angina pectoris, heart failure, myocardial infarction and atrial fibrillation in humans and animals using an effective amount of the pharmaceutical composition of claim 7.

* * * * *